(12) United States Patent
Wells et al.

(10) Patent No.: US 9,719,068 B2
(45) Date of Patent: Aug. 1, 2017

(54) METHODS AND SYSTEMS FOR CONVERTING PRECURSOR CELLS INTO INTESTINAL TISSUES THROUGH DIRECTED DIFFERENTIATION

(75) Inventors: James M. Wells, Cincinnati, OH (US);
Jason R. Spence, Ann Arbor, MI (US);
Aaron M. Zorn, Cincinnati, OH (US);
Noah F. Shroyer, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 13/695,887

(22) PCT Filed: May 6, 2011

(86) PCT No.: PCT/US2011/035518
§ 371 (c)(1),
(2), (4) Date: Nov. 2, 2012

(87) PCT Pub. No.: WO2011/140441
PCT Pub. Date: Nov. 10, 2011

(65) Prior Publication Data
US 2013/0137130 A1  May 30, 2013

Related U.S. Application Data

(60) Provisional application No. 61/332,178, filed on May 6, 2010.

(51) Int. Cl.
*C12N 5/00* (2006.01)
*C12N 5/071* (2010.01)
*C12N 5/077* (2010.01)

(52) U.S. Cl.
CPC ......... *C12N 5/0679* (2013.01); *C12N 5/0661* (2013.01); *C12N 2501/119* (2013.01); *C12N 2501/155* (2013.01); *C12N 2501/16* (2013.01); *C12N 2501/385* (2013.01); *C12N 2501/415* (2013.01); *C12N 2502/02* (2013.01); *C12N 2502/45* (2013.01)

(58) Field of Classification Search
CPC .................................................. C12N 5/0679
USPC ....................................................... 435/325
See application file for complete search history.

(56) References Cited

U.S. PATENT DOCUMENTS

| | | | |
|---|---|---|---|
| 5,942,435 A * | 8/1999 | Wheeler | 435/325 |
| 7,326,572 B2 | 2/2008 | Fisk | |
| 7,510,876 B2 | 3/2009 | D'Amour | |
| 7,541,185 B2 | 6/2009 | D'Amour | |
| 7,625,753 B2 | 12/2009 | Kelly et al. | |
| 7,704,738 B2 | 4/2010 | D'Amour | |
| 7,985,585 B2 | 7/2011 | D'Amour | |
| 8,216,836 B2 | 7/2012 | D'Amour | |
| 2005/0266554 A1 | 12/2005 | D'Amour | |
| 2009/0011502 A1 | 1/2009 | D'Amour | |
| 2009/0042287 A1 | 2/2009 | D'Amour | |
| 2009/0220959 A1 | 9/2009 | D'Amour | |
| 2009/0253202 A1 | 10/2009 | D'Amour | |
| 2010/0041150 A1 | 2/2010 | Kelly et al. | |
| 2010/0151568 A1 | 6/2010 | D'Amour | |
| 2012/0196312 A1 | 8/2012 | Sato et al. | |

FOREIGN PATENT DOCUMENTS

| | | |
|---|---|---|
| WO | WO 2010/090513 A2 | 8/2010 |
| WO | WO 2010/143747 A1 | 12/2010 |
| WO | WO 2011/139628 A1 | 11/2011 |
| WO | WO 2011/140441 A2 | 11/2011 |
| WO | WO 2015/183920 A2 | 12/2015 |

OTHER PUBLICATIONS

D'Amour et al., cited on IDS Jan. 15, 2013.*
Johannesson et al. (Mar. 2009, PLoS One, vol. 4(3), pp. 1-13).*
Simon-Assmann et al. (2007, Cell Biol. Toxicol., vol. 23, pp. 241-256).*
Bastide et al. (2007, JCB, vol. 178(4), pp. 635-648).*
Brevini et al., 2010, Theriogenology, vol. 74, pp. 544-550.*
Paris et al., 2010, Theriogenology, vol. 74, pp. 516-524.*
Munoz et al., 2008, Theriogenology, vol. 69, pp. 1159-1164.*
Petitte et al., 2004, Mech. of Develop., vol. 121, pp. 1159-1168.*
Lavial et al., 2010, Develop. Growth Diff., vol. 52, pp. 101-114.*
Yamada et al. 2001, Am. J. Physiol. Gastrointest. Liver Pyshiol., vol. 281, pp. G229-G236.*
Chen et al. 2009, Am. J. Physiol. Gastrointest. Liver Pyshiol., vol. 297, pp. G1126-G1137.*
Ameri et al. (ePUB Nov. 3, 2009, Stem Cells, vol. 28(1), pp. 45-56).*
Zorn et al. (ePUB Aug. 12, 2009, Annual Rev. Cell Dev. Biol., vol. 25, pp. 221-251).*

(Continued)

*Primary Examiner* — Thaian N Ton
*Assistant Examiner* — David A Montanari
(74) *Attorney, Agent, or Firm* — Frost Brown Todd LLC

(57) ABSTRACT

The generation of complex organ tissues from human embryonic and pluripotent stem cells (PSCs) remains a major challenge for translational studies. It is shown that PSCs can be directed to differentiate into intestinal tissue in vitro by modulating the combinatorial activities of several signaling pathways in a step-wise fashion, effectively recapitulating in vivo fetal intestinal development. The resulting intestinal "organoids" were three-dimensional structures consisting of a polarized, columnar epithelium surrounded by mesenchyme that included a smooth muscle-like layer. The epithelium was patterned into crypt-like SOX9-positive proliferative zones and villus-like structures with all of the major functional cell types of the intestine. The culture system is used to demonstrate that expression of NEUROG3, a pro-endocrine transcription factor mutated in enteric anendocrinosis is sufficient to promote differentiation towards the enteroendocrine cell lineage. In conclusion, PSC-derived human intestinal tissue should allow for unprecedented studies of human intestinal development, homeostasis and disease.

9 Claims, 26 Drawing Sheets

(56) References Cited

OTHER PUBLICATIONS

Alessi et al. (2006, Annu. Rev. Biochem., vol. 75, pp. 137-63).*
Rohrschneider et al. (2009, Dev. Dyn., vol. 238(4), pp. 789-796).*
Wells et al. (2014, Development, vol. 141, pp. 752-760).*
Spence et al., 2011, Nature, vol. 470, pp. 105-110.*
Andrews, P. et al., "Embryonic stem (ES) cells and embryonal carcinoma (EC) cells: opposite sides of the same coin," *Biochem Soc Trans*, 2005, 33:1526-1530.
Ang., S.L. et al., "The formation and maintenance of the definitive endoderm lineage in the mouse: involvement of HNF3/forkhead proteins," *Development*, 1993, 119:1301-1315.
Bansal, D. et al., "An ex-vivo human intestinal model to study entamoeba histolytica pathogenesis," *PLoS Neglected Tropical Diseases*, Nov. 2009, 3(11): e551.
Beck, F., et al., "Expression of Cdx-2 in the mouse embryo and placenta: possible role in patterning of the extra-embryonic membranes," *Dev Dyn*, 1995, 204:219-227.
Coghlan, M. et al., "Selective small molecule inhibitors of glycogen synthase kinase-3 modulate glycogen metabolism and gene transcription," *Chem Biol*, 2000, 7(10):793-803.
Couzin, J., "Small RNAs make big splash," *Science*, 2002, 298:2296-2297.
D'Amour, K.A. et al., "Efficient differentiation of human embryonic stem cells to definitive endoderm," *Nature Biotechnology*, Dec. 2005, 23(12):1534-1541.
D'Amour, K.A. et al., "Production of pancreatic hormone-expressing endocrine cells from human embryonic stem cells," *Nat Biotechnol*, 2006, 24:1392-1401.
De Santa Barbara, P. et al., "Development and differentiation of the intestinal epithelium," *Cell Mol Life Sci*, 2003, 60(7): 1322-1332.
Dessimoz, J. et al., "FGF signaling is necessary for establishing gut tube domains along the anterior-posterior axis in vivo," *Mech Dev*, 2006, 123:42-55.
Elbashir, S.M. et al., "Functional anatomy of siRNAs for mediating efficient RNAi in *Drosophila melanogaster* embryo lysate," *EMBO J.*, 2001, 20:6877-6888.
Evans, M.J. and Kaufman, M.H., "Establishment in culture of pluripotent cells from mouse embryos," *Nature*, 1981, 292(5819):154-156.
Gracz, A.D. et al., "Sox9-Expression Marks a Subset of CD24-expressing Small Intestine Epithelial Stem Cells that Form Organoids in vitro," *Am J Physiol Gastrointest Liver Physiol*, 2010, 298:G590-600.
Gregorieff, A. and Clevers, H., "Wnt signaling in the intestinal epithelium: from endoderm to cancer," *Genes & Dev.*, 2005, 19:877-890.
Hannon, G.J., "review article RNA interference," *Nature*, 2002, 418:244-251.
Haveri, H., et al., "Transcription factors GATA-4 and GATA-6 in normal and neoplastic human gastrointestinal mucosa," *BMC Gastroenterology*, 2008, 8: 9.
Hutvagner, G. et al., "A microRNA in a Multiple-Turnover RNAi Enzyme Complex," *Science*, 2002, 297:2056-2060.
Jenny, M., et al., "Neurogenin3 is differentially required for endocrine cell fate specification in the intestinal and gastric epithelium," *EMBO J*, 2002, 21:6338-6347.
Kaji, K. et al., 2009, "Virus free induction of pluripotency and subsequent excision of reprogramming factors," *Nature*, 2009, 458:771-775.
Klimanskaya, I. et al., "Human embryonic stem cells derived without feeder cells," *Lancet*, 2005, 365(9471): 1636-1641.
Kroon, E., et al., "Pancreatic endoderm derived from human embryonic stem cells generates glucose-responsive insulin secreting cells in vivo," *Nat Biotechnol*, 2008, 26(4):443-52.
Kubo, A. et al., "Development of definitive endoderm from embryonic stem cells in culture," *Development*, 2004, 131(7):1651-1662.
Lambert, P.F. et al., "Using an immortalized cell line to study the HPV life cycle in organotypic 'raft' cultures," *Methods in molecular medicine*, 2005, 119:141-155.

Lee, C.S. et al., "Neurogenin 3 is essential for the proper specification of gastric enteroendocrine cells and the maintenance of gastric epithelial cell identity," *Genes Dev*, 2002, 16:1488-1497.
Liu, J. et al., "A small-molecule agonist of the Wnt signaling pathway," *Angew Chem Int Ed Engl.*, 2005, 44(13):1987-1990.
Logan, C.Y. and Nusse, R., "The Wnt Signaling Pathway in Development and Disease," *Annual Review of Cell and Developmental Biology*, 2004, 20:781-810.
Lopez-Diaz, L. et al., "Intestinal Neurogenin 3 directs differentiation of a bipotential secretory progenitor to endocrine cell rather than goblet cell fate," *Dev Biol*, 2007, 309:298-305.
Ludwig, T.E., et al, "Derivation of human embryonic stem cells in defined conditions," *Nat Biotechnol*, 2006, 24:185-187.
Ludwig, T.E., et al., "Feeder-independent culture of human embryonic stem cells," *Nat Methods*, 2006, 3:637-646.
Martin, G.R., "Teratocarcinomas and mammalian embryogenesis," *Science*, 1980, 209(4458):768-776.
McLin, V.A. et al., "Repression of Wnt/β-catenin signaling in the anterior endoderm is essential for liver and pancreas development," *Development*, 2007, 134:2207-2217.
McLin, V.A. et al., "The role of the visceral mesoderm in the development of the gastrointestinal tract," *Gastroenterology*, 2009, 136:2074-2091.
McManus, T. and Sharp, P.A., "Gene silencing in mammals by small interfering RNAs," *Nat. Rev. Genet*, 2002, 3:737-747.
Miyabayashi, T. et al., "Wnt/β-catenin/CBP signaling maintains long-term murine embryonic stem cell pluripotency," *Proc Natl Acad Sci USA*, 2007, 104(13):5668-5673.
Neiiendam, J.L. et al., "An NCAM-derived FGF-receptor agonist, the FGL-peptide, induces neurite outgrowth and neuronal survival in primary rat neurons," *J Neurochem*, 2004, 91(4):920-935.
Okita, K. et al., "Generation of Mouse Induced Pluripotent Stem Cells Without Viral Vectors," *Science*, 2008, 322(5903):949-953.
Ootani, A. et al., "Sustained in vitro intestinal epithelial culture within a Wnt-dependent stem cell niche," *Nat Med*, 2009, 15:701-706.
Paddison, P. et al., "Short Hairpin Activated Gene Silencing in Mammalian Cells," *Cancer Cell*, 2002, 2:17-23.
Pai, R. et al., "Deoxycholic acid activates beta-catenin signaling pathway and increases colon cell cancer growth and invasiveness," *Mol Biol Cell*, 2004, 15(5):2156-2163.
Richards, M. et al., "The transcriptome profile of human embryonic stem cells as defined by SAGE," *Stem Cells*, 2004, 22:51-64.
Sancho, E. et al., "Signaling Pathways in Intestinal Development and Cancer," *Annual Review of Cell and Developmental Biology*, 2004, 20:695-723.
Sato, T. et al., "Single Lgr5 stem cells build crypt-villus structures in vitro without a mesenchymal niche," *Nature*, 2009, 459:262-265.
Shan, J. et al., "Identification of a specific inhibitor of the dishevelled PDZ domain," *Biochemistry*, 2005, 44(47):15495-15503.
Spence, J.R. & Wells, J.M., "Translational embryology: Using embryonic principles to generate pancreatic endocrine cells from embryonic stem cells," *Developmental Dynamics*, 2007, 236:3218-3227.
Spence, J.R. et al., "Directed differentiation of human pluripotent stem cells into intestinal tissue in vitro," *Nature*, Feb. 2011, 470:105-109.
Stadtfeld, M. et al., "Induced Pluripotent Stem Cells Generated without Viral Integration," *Science*, 2008, 322(5903):945-949.
Taipale, J. and Beachy, P.A., "The Hedgehog and Wnt signalling pathways in cancer," *Nature*, 2001, 411:349-354.
Takahashi, K. and Yamanaka, S., "Induction of pluripotent stem cells from mouse embryonic and adult fibroblast cultures by defined factors," *Cell*, 2006, 126:663-676.
Takahashi, K. et al., "Induction of pluripotent stem cells from adult human fibroblasts by defined factors," *Cell*, 2007, 131:861-872.
Thomson, J.A. et al., "Embryonic Stem Cell Lines Derived from Human Blastocysts," *Science*, 1998, 282(5391):1145-1147.
Tuschl, T. et al., "Targeted mRNA degradation by double-stranded RNA in vitro," *Genes Dev.*, 1999, 13:3191-3197.
Van Breemen, R.B. and Li, Y., "Caco-2 cell permeability assays to measure drug absorption," *Expert Opin. Drug Metab. Toxicol.*, Aug. 2005, 1(2):175-185.

(56) References Cited

OTHER PUBLICATIONS

Wang, J., et al., "Mutant neurogenin-3 in congenital malabsorptive diarrhea," New England Journal of Medicine, 2006, 355:270-280.
Wells, J. and Melton, D., "Early mouse endoderm is patterned by soluble factors from adjacent germ layers," Development, 2000, 127:1563-1572.
Woltjen, K. et al., "piggyBac transposition reprograms fibroblasts to induced pluripotent stem cells," Nature, 2009, 458:766-770.
Zhang, Q. et al., "Small-molecule synergist of the Wnt/β-catenin signaling pathway," Proc Natl Acad Sci USA, 2007, 104(18):7444-7448.
Zhou, H. et al., "Generation of Induced Pluripotent Stem Cells Using Recombinant Proteins," Cell Stem Cell, 2009, 4(5):381-384.
Zhou, Q., et al., "In vivo reprogramming of adult pancreatic exocrine cells to beta-cells," Nature, 2008, 455: 627-632.
Zorn, A. and Wells, J., "Vertebrate endoderm development and organ formation," Annu Rev Cell Dev Biol, 2009, 25:221-251.
International Preliminary Report on Patentability, mailed in related PCT Application No. US2011/035518, issued Nov. 6, 2012.
International Search Report and Written Opinion dated Dec. 15, 2015 for Application No. PCT/US2015/032626.
International Search Report and Written Opinion dated Jan. 25, 2016 for Application No. PCT/US2015/055956.
Agopian, V.G., et al., "Intestinal Stem Cell Organoid Transplantation Generates Neomucosa in Dogs," Journal of Gastrointestinal Surgery, Jan. 23, 2009, 13(5):971-982, XP055241418, 12 pgs.
Avansino, J.R., et al., "Orthotopic transplantation of intestinal mucosal organiods in rodents," Surgery, Sep. 2006, 140(3):423-434, XP005610494, 12 pgs.
Barker, N., et al., "Lgr5+ve Stem Cells Drive Self-Renewal in the Stomach and Build Long-Lived Gastric Units in Virto," Cell Stem Cell, Jan. 1, 2012, 6(1):25-36, XP055210573, 12 pgs.
Koo, B-K., et al., "Controlled gene expression in primary Lgr5 organoid cultures," Nature Methods, Jan. 1, 2012, 9(1):81-83, XP055225429, 4 pgs.
Lindley, R.M., et al., "Human and Mouse Enteric Nervous System Neurosphere Transplants Regulate the Function of Aganglionic Embryonic Distal Colon," Gastroenterology, Jul. 2008, 135(1):205-216, XP022823118, 18 pgs.
Mahe, M.M., et al., "Establishment of Gastrointestinal Epithelial Organoids," Current Protocols in Mouse Biology 2013, 2013, 3(4):217-240, XP002750112, 24 pgs.
McCracken, K.W., et al., "Generating human intestinal tissue from pluripotent stem cells in vitro," Nature Protocols, Nov. 10, 2011, 6(12):1920-1928, XP055210541, 9 pgs.
McCracken, K.W., et al., "Modelling human development and disease in pluripotent-stem-cell-derived gastric organoids," Nature, Oct. 29, 2014, 516(7531):400-404, XP055210509, 19 pgs.
Noguchi, T-A.K., et al., "Generation of stomach tissue from mouse embryonic stem cells," Nature Cell Biology, Jul. 20, 2015, 17(8):984-993, XP055225165, 19 pgs.
Speer, A.L., et al., "Murine Tissue-Engineered Stomach Demonstrates Epithelial Differentiation," Journal of Surgical Research, Mar. 22, 2011, 171(1):6-14, XP028317226, 9 pgs.
Takaki, M., et al., "In Vitro Formation of Enteric Neural Network Structure in a Gut-Like Organ Differentiated from Mouse Embryonic Stem Cells," Stem Cells, Jun. 9, 2006, 24(6):1414-1422, XP55241404, 9 pgs.
Watson, C.L., et al., "An in vivo model of human small intestine using pluripotent stem cells," Nature Medicine, Oct. 19, 2014, 20(11):1310-1314, XP055241417, 7 pgs.
Wells, J.M., et al., "How to Make an intestine," Development, Feb. 15, 2014, 141(4):752-760, XP055241409, 9 pgs.

\* cited by examiner

ALB/CDX2/PDX1
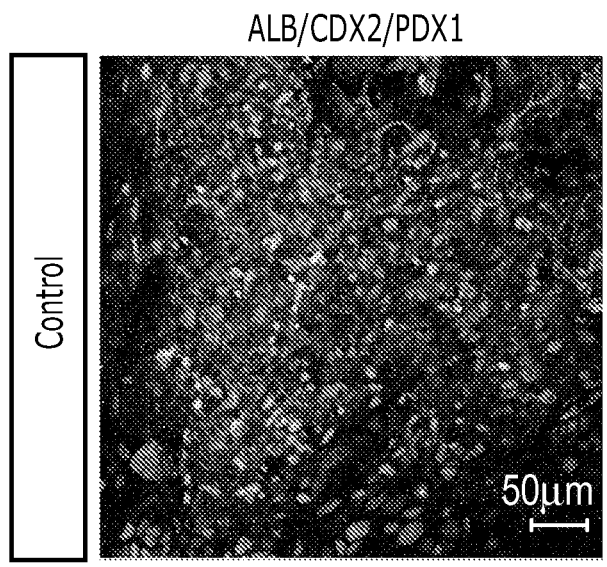
FIGURE 1b | Control
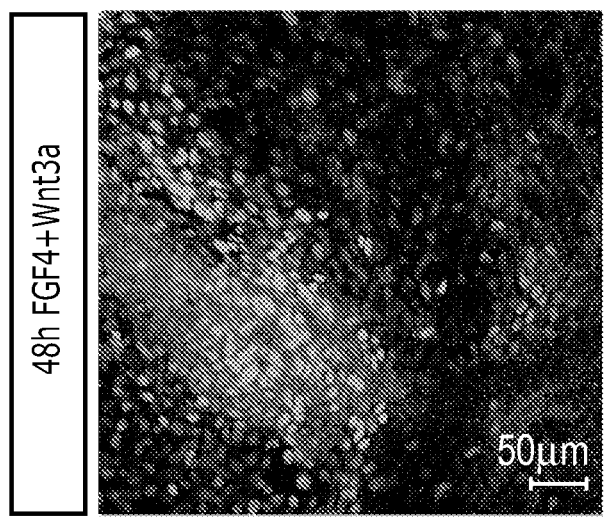
FIGURE 1c | 48h FGF4+Wnt3a
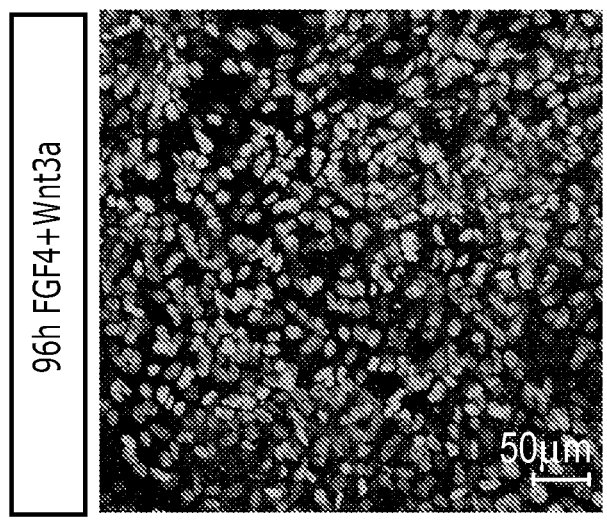
FIGURE 1d | 96h FGF4+Wnt3a

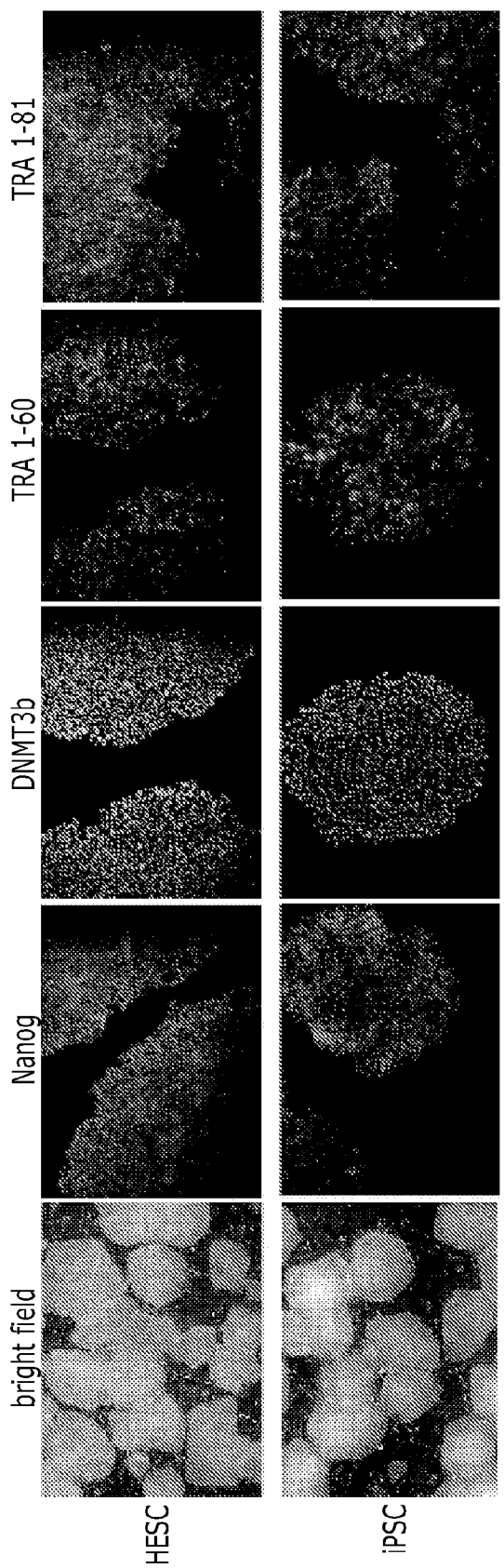
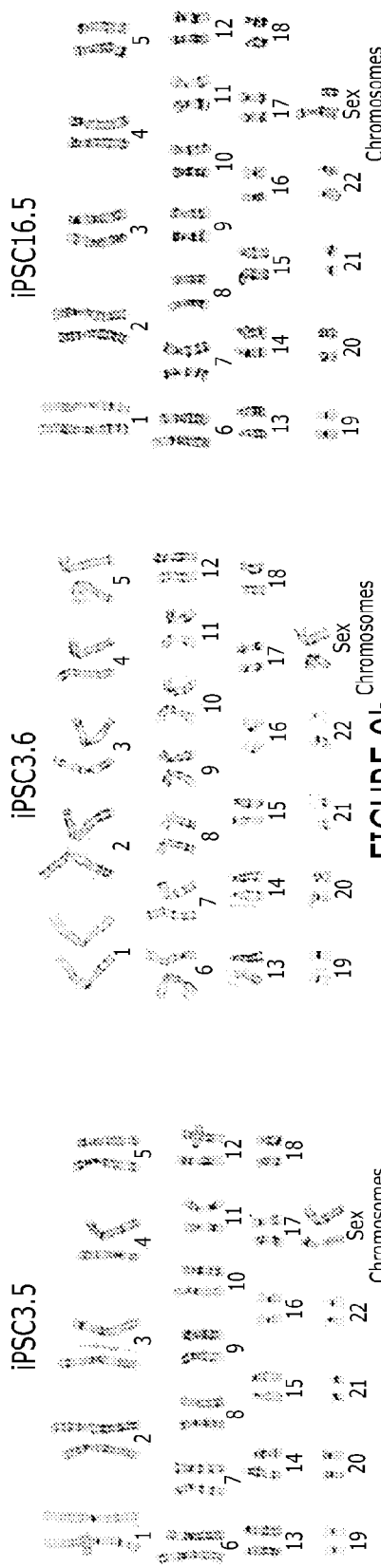
FIGURE 9a
FIGURE 9b

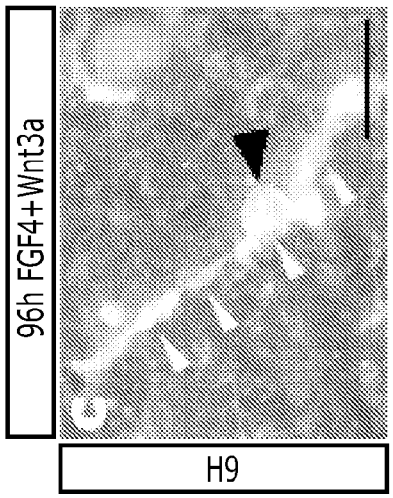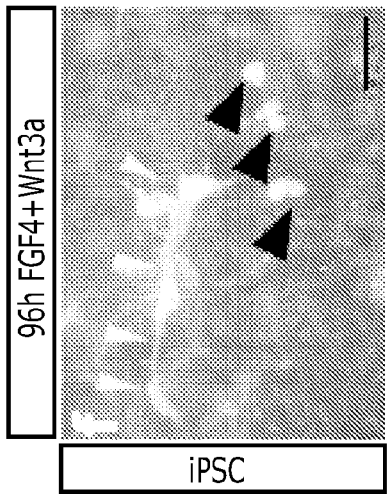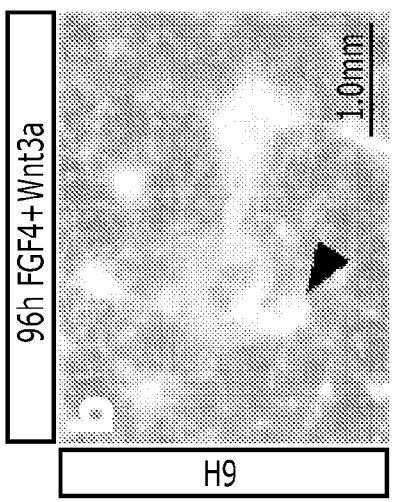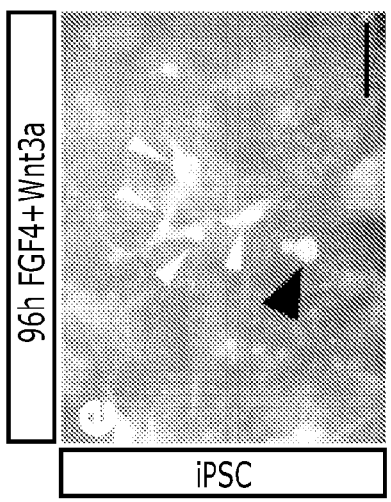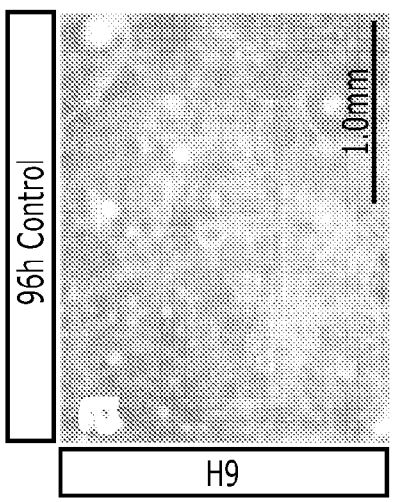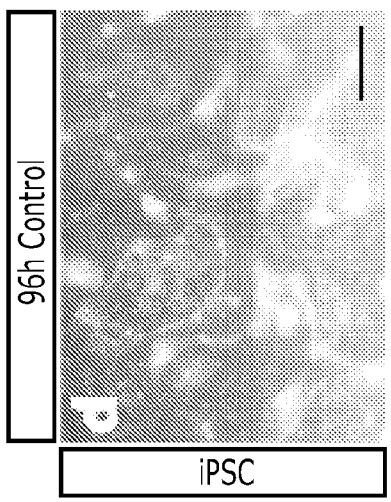
FIGURE 10a  FIGURE 10b  FIGURE 10c
FIGURE 10d  FIGURE 10e  FIGURE 10f

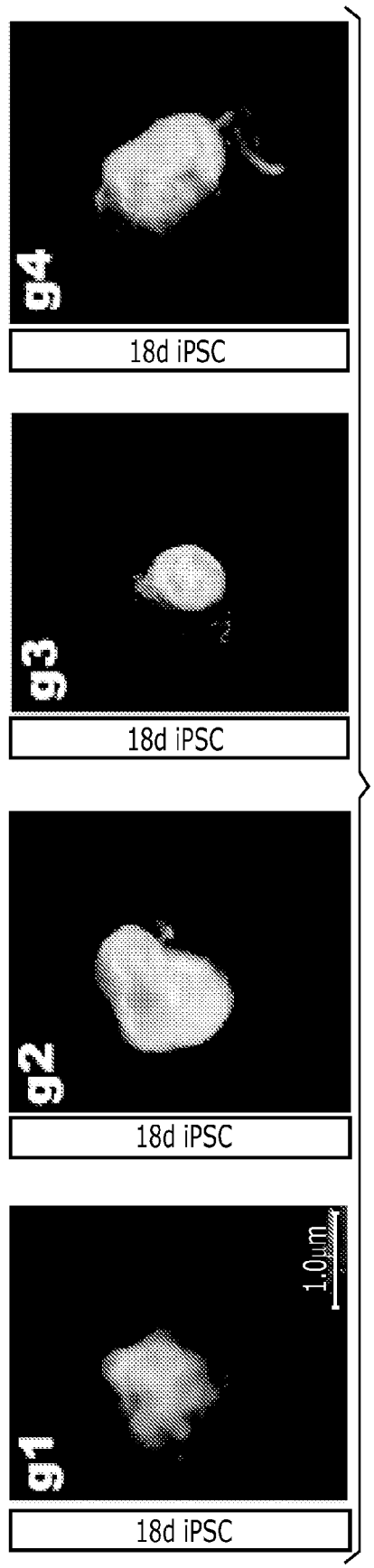
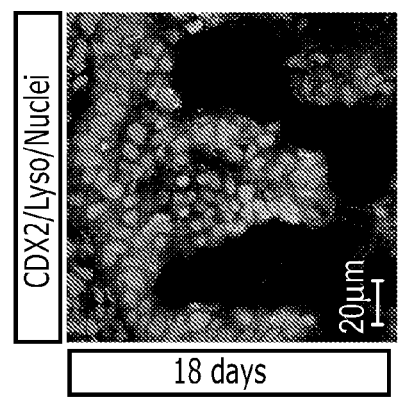
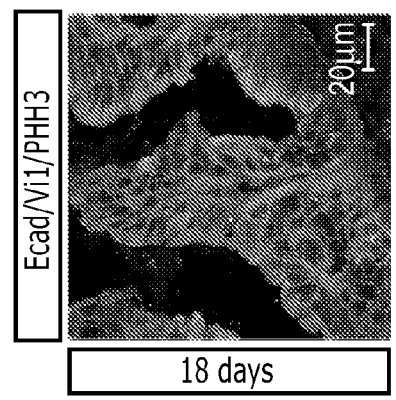
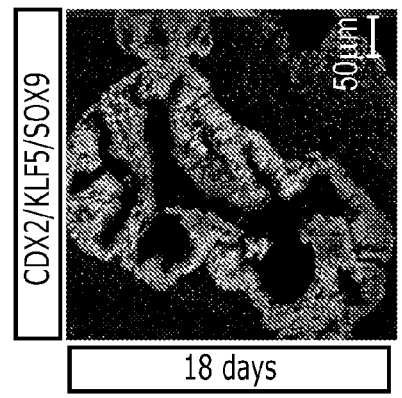
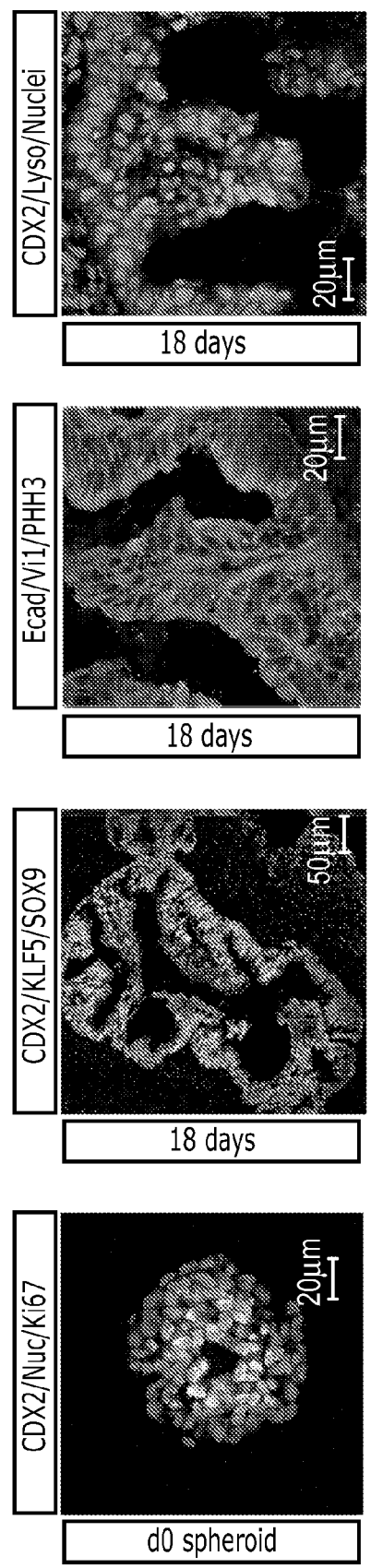

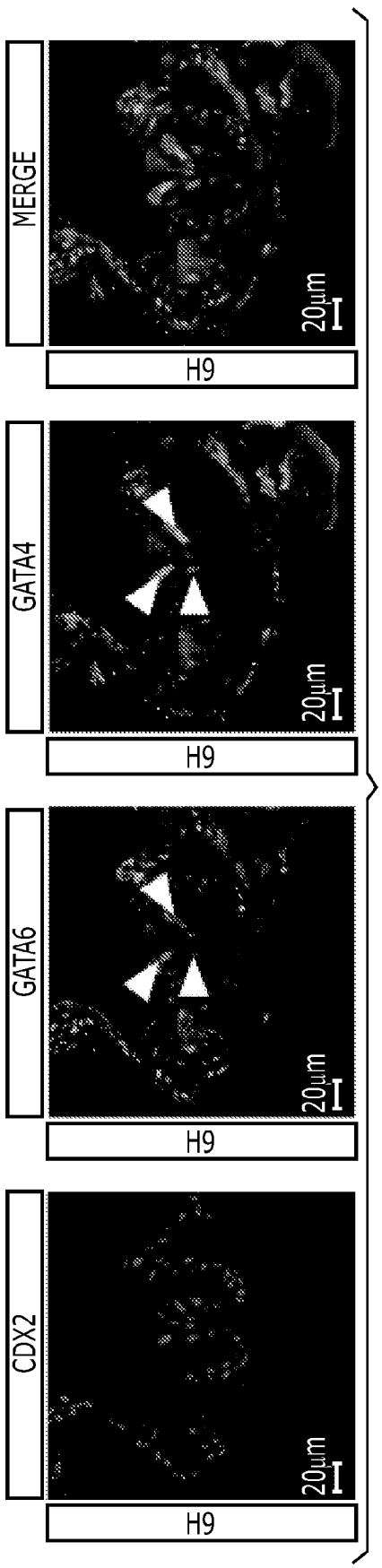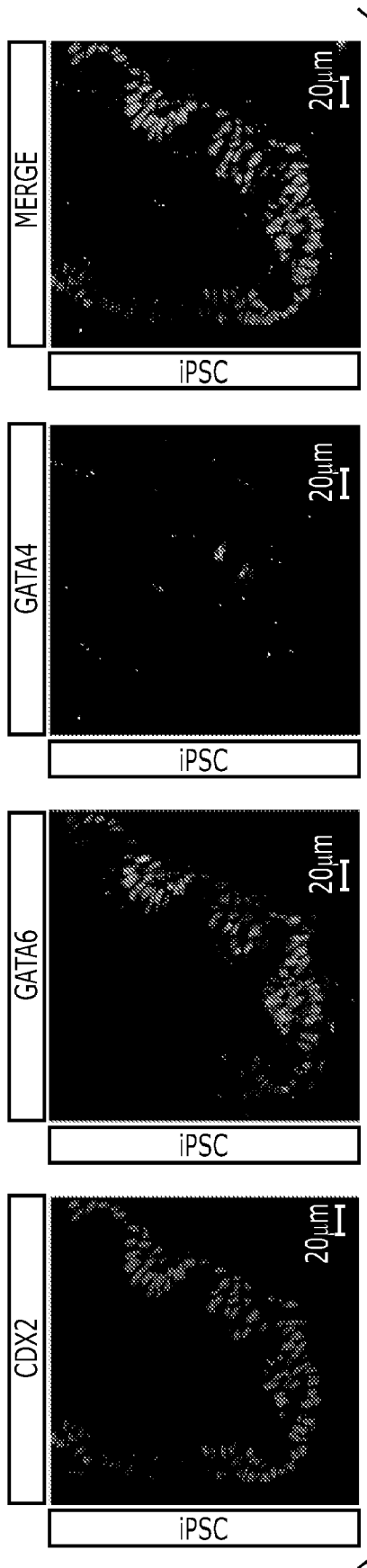
FIGURE 12a
FIGURE 12b

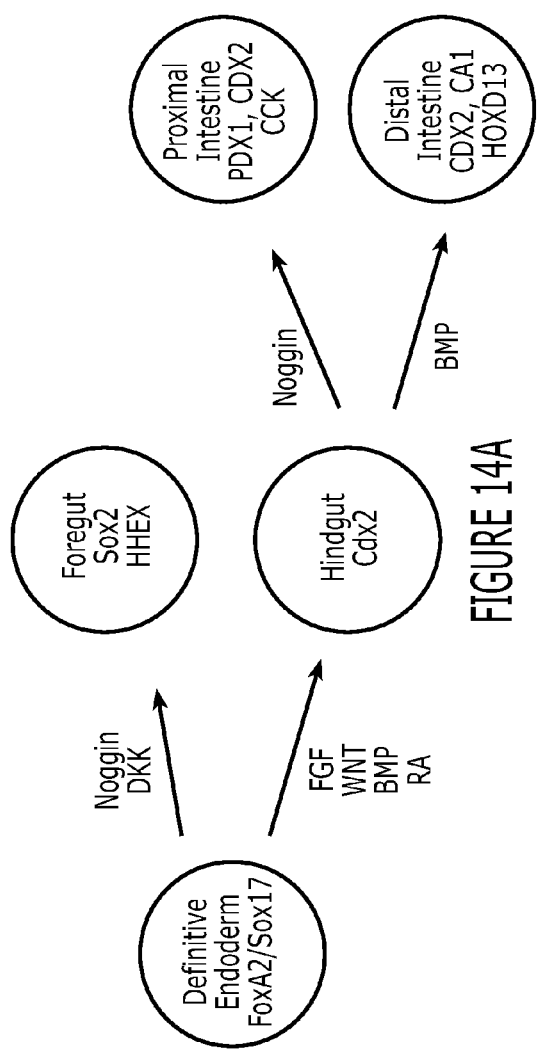
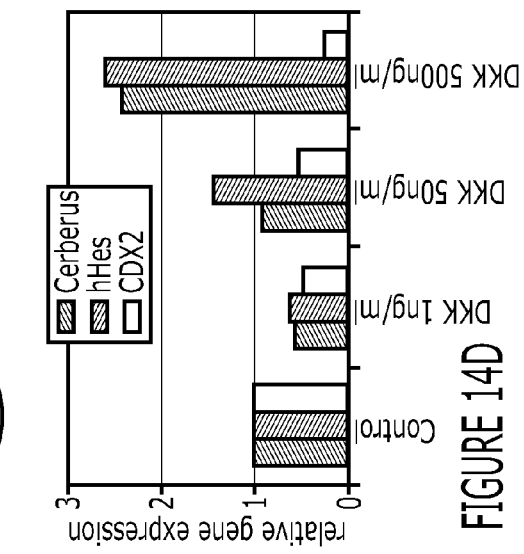
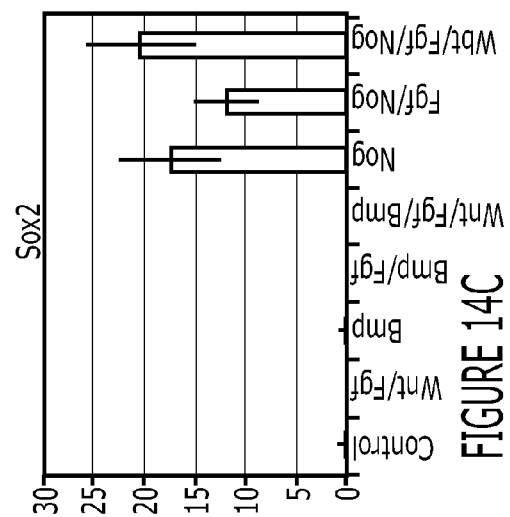
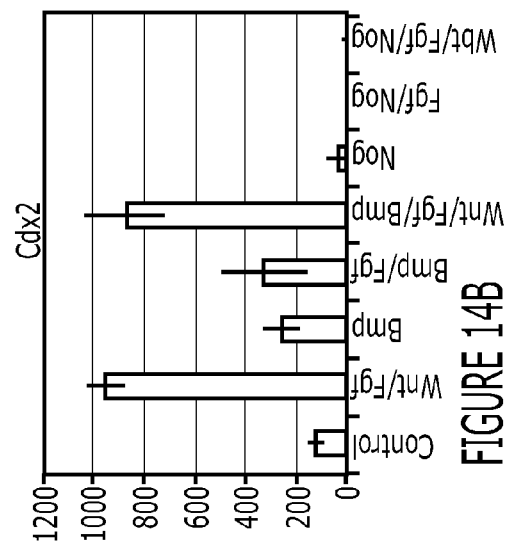
FIGURE 14A
FIGURE 14B
FIGURE 14C
FIGURE 14D

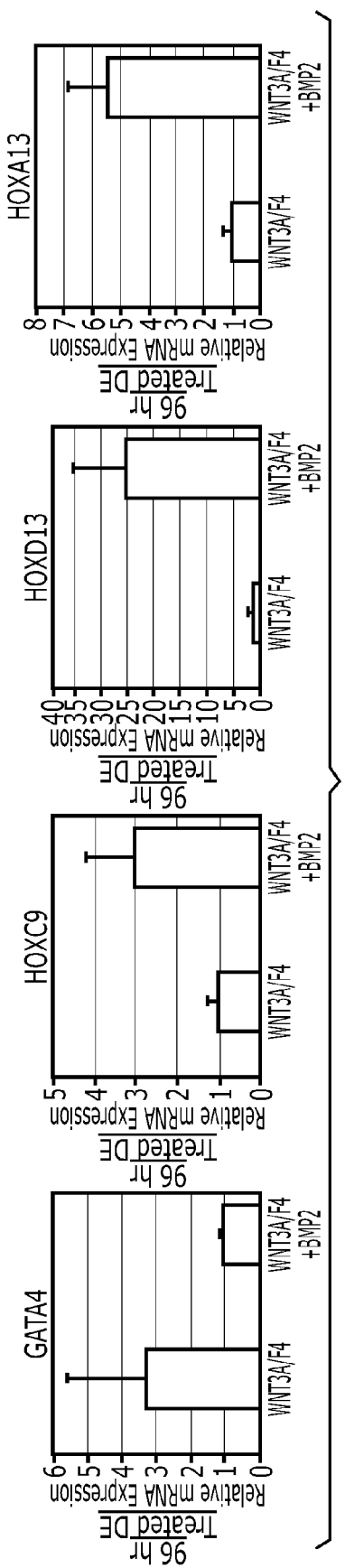
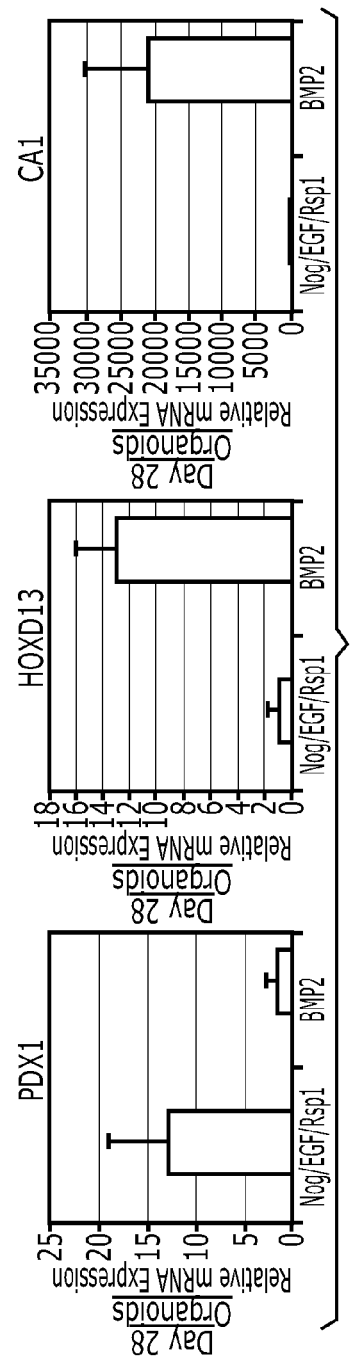
FIGURE 16A
FIGURE 16B

METHODS AND SYSTEMS FOR CONVERTING PRECURSOR CELLS INTO INTESTINAL TISSUES THROUGH DIRECTED DIFFERENTIATION

CROSS-REFERENCE TO RELATED APPLICATIONS

The present application is a U.S. National Stage entry under 35 U.S.C. §371 of International Application No. PCT/US2011/035518, filed on May 6, 2011, designating the United States of America and published in English on Nov. 10, 2011, which in turn claims priority to U.S. Provisional Application No. 61/332,178, filed on May 6, 2010, each of which is hereby incorporated by reference in its entirety.

STATEMENT REGARDING FEDERALLY-SPONSORED RESEARCH

This invention was made with government support under GM072915, DK080823, DK084167, CA142826, DK083202, and HD007463 awarded by the National Institutes of Health. The government has certain rights in the invention.

FIELD OF THE INVENTION

The invention disclosed herein generally relates to methods and systems for converting stem cells into specific tissue(s) or organ(s) through directed differentiation. In particular, the invention disclosed herein relates to methods and systems for promoting definitive endoderm formation from pluripotent stem cells. The invention disclosed herein further relates to methods and systems for promoting intestinal organoids or tissue formations from differentiated definitive endoderm.

BACKGROUND

Stem cells are found in all multi cellular organisms. They are characterized by the ability to renew themselves through mitotic cell division and differentiate into a diverse range of specialized cell types. The two broad types of mammalian stem cells are: embryonic stem cells that are isolated from the inner cell mass of blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin, or intestinal tissues.

Stem cells can now be grown and transformed into specialized cells with characteristics consistent with cells of various tissues such as muscles or nerves through cell culture. Highly plastic adult stem cells from a variety of sources, including umbilical cord blood and bone marrow, are routinely used in medical therapies. Embryonic cell lines and autologous embryonic stem cells generated through therapeutic cloning have also been proposed as promising candidates for future therapies.

The classical definition of a stem cell is typically indicative of two properties: self-renewal, the ability to go through numerous cycles of cell division while maintaining the undifferentiated state, and potency, the capacity to differentiate into specialized cell types. In some embodiments, stem cells are either totipotent or pluripotent, i.e. they are able to give rise to any mature cell type, although multipotent or unipotent progenitor cells are sometimes referred to as stem cells.

Potency specifies the differentiation potential (the potential to differentiate into different cell types) of the stem cell:

Totipotent stem cells (also known as omnipotent stem cells) can differentiate into embryonic and extraembryonic cell types. These cells can construct a complete, viable, organism. The cells are produced from the fusion of an egg and sperm cell. Cells produced by the first few divisions of the fertilized egg are also totipotent.

Pluripotent stem cells (PSCs) are the descendants of totipotent cells and can differentiate into nearly all cells, i.e., cells derived from any of the three germ layers, including endoderm (interior stomach lining, gastrointestinal tract, the lungs), mesoderm (muscle, bone, blood, urogenital), and ectoderm (epidermal tissues and nervous system).

Multipotent stem cells can differentiate into a number of cells, but only those of a closely related family of cells.

Oligopotent stem cells can differentiate into only a few cells, such as lymphoid or myeloid stem cells.

Unipotent cells can produce only one cell type, their own, but have the property of self-renewal which distinguishes them from non-stem cells (e.g., muscle stem cells).

Embryonic and induced pluripotent stem cells have had an unprecedented impact on our ability to study human diseases and to generate replacement tissues that are therapeutically effective in animal models.

In developmental biology, cellular differentiation is the process by which a less specialized cell becomes a more specialized cell type. Most successful efforts to direct the differentiation of human PSCs into therapeutic cell types have been based on studies of embryonic organ development. Examples include the generation of liver hepatocytes and pancreatic endocrine cells, which have shown functional potential in animal models of liver disease and diabetes. Similarly, differentiation of PSCs into intestine may provide therapeutic benefit for diseases such as necrotizing enterocolitis, inflammatory bowel diseases and short gut syndromes.

As discussed above, a pluripotent stem cell has the potential to differentiate into any of the three germ layers: endoderm (interior stomach lining, gastrointestinal tract, the lungs), mesoderm (muscle, bone, blood, urogenital), and ectoderm (epidermal tissues and nervous system). As such, pluripotent stem cells can give rise to any fetal or adult cell type. However, the fate of the particular pluripotent stem cells is controlled by numerous cellular signaling pathway and numerous factors. Further, the pluripotent stem cells alone cannot develop into a fetal or adult animal because they lack the potential to contribute to extraembryonic tissue, such as the placenta.

What is needed in the art are methods and systems for accurately controlling the destination of the pluripotent stem cells in order to create the specific type of tissue or organism of desire.

SUMMARY OF THE INVENTION

In some embodiments, a method of inducing formation of an intestinal tissue is provided, comprising: activating one or more signaling pathways within a precursor cell.

In some embodiments, the one or more signaling pathways are selected from the group consisting of the Wnt signaling pathway, Wnt/APC signaling pathway, FGF signaling pathway, TGF-beta signaling pathway, shh signaling pathway, BMP signaling pathway, Notch signaling pathway, Hedgehog signaling pathway, LKB signaling pathway, and Par polarity signaling pathway; and obtaining an intestinal tissue descended from said precursor cell.

In some embodiments, the method further comprises: providing said precursor cell. In some embodiments, the method further comprises: culturing, after said activating step, said activated precursor cell in vitro to form a 3-dimensional tissue structure.

In some embodiments, the activating and obtaining steps are conducted in vitro.

In some embodiments, the one or more signaling pathways comprise the Wnt signaling pathway and FGF signaling pathway.

In some embodiments, the Wnt signaling pathway is activated by contacting the precursor cell with one or more molecules selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16.

In some embodiments, the FGF signaling pathway is activated by contacting the precursor cell with one or more molecules selected from the group consisting of FGF1, FGF2, FGF3, FGF4, FGF10, FGF11, FGF12, FGF13, FGF14, FGF15, FGF16, FGF17, FGF18, FGF19, FGF20, FGF21, FGF22, and FGF23.

In some embodiments, the activating step comprises contacting said precursor cell with both Wnt3a and FGF4 over a specified activation period.

In some embodiments, the precursor cell is contacted by Wnt3a during a first activation period and by FGF4 during a second activation period. In some embodiments, the first activation period and the second activation period overlap. In some embodiments, the first activation period and said second activation period do not overlap.

In some embodiments, the specified activation period is between 24 and 120 hours.

In some embodiments, the precursor cell is contacted with Wnt3a at a concentration between 50-1500 ng/ml.

In some embodiments, the said precursor cell is elected from the group consisting of an embryonic stem cell, an embryonic germ cell, an induced pluripotent stem cell, a mesoderm cell, a definitive endoderm cell, a posterior endoderm cell, and a hindgut cell.

In some embodiments, the definitive endoderm cell is derived from a pluripotent stem cell.

In some embodiments, the pluripotent stem cell is an embryonic stem cell, an embryonic stem cell, an adult stem cell, or an induced pluripotent stem cell.

In some embodiments, the definitive endoderm cell is derived by contacting the pluripotent stem cell with one or more molecules selected from the group consisting of Activin, the BMP subgroups of the TGF-beta superfamily of growth factors; Nodal, Activin A, Activin B, BMP4, Wnt3a, and a combinations thereof.

In some embodiments, the pluripotent stem cell is a mammalian pluripotent stem cell, including but not limited to human pluripotent stem cell or a mouse pluripotent stem cell.

In some embodiments, the human pluripotent stem cell is selected from the group consisting of a human embryonic stem cell, a human embryonic germ cell, and an induced human pluripotent stem cell.

In some embodiments, an intestinal tissue produced in vitro from one or more precursor cells is provided.

In some embodiments, the one or more precursor cells are selected from the group consisting of an embryonic stem cell, an embryonic germ cell, an induced pluripotent stem cell, a mesoderm cell, a definitive endoderm cell, a posterior endoderm cell, and a hindgut cell.

In some embodiments, a kit comprising an intestinal tissue produced in vitro from one or more precursor cells is provided.

In some embodiments, a method for identifying the absorption effect of intestinal cells or tissues is provided, comprising: contacting intestinal cells or tissues with a compound, wherein said intestinal cells or tissues are produced in vitro from one or more precursor cells; and detecting a level of absorption of said compound by said intestinal cells or tissues.

BRIEF DESCRIPTION OF THE DRAWINGS

Those of skill in the art will understand that the drawings, described below, are for illustrative purposes only. The drawings are not intended to limit the scope of the present teachings in any way.

FIG. 1 illustrates exemplary embodiments of the present invention. FIGS. 1b through 1d illustrate immunofluorescence images showing the same.

FIG. 2 illustrates exemplary embodiments in accordance with the present invention. FIG. 2a includes bright field images of definitive endoderm (DE) treated with FGF4 and Wnt3a. FIG. 2b shows immunofluorescent images of the same DE cultures illustrated in FIG. 2a.

FIG. 3 illustrates exemplary embodiments in accordance with the present invention.

FIG. 4 illustrates exemplary embodiments in accordance with the present invention.

FIG. 5 illustrates exemplary embodiments in accordance with the present invention.

FIG. 6 illustrates exemplary embodiments in accordance with the present invention.

FIG. 7 includes bar charts illustrating exemplary embodiments in accordance with the present invention. The bar charts depict time and concentration dependent induction of CDX2 by FGF4 and Wnt3a.

FIG. 9 illustrates exemplary embodiments in accordance with the present invention. FIG. 9a includes both bright field and immunofluorescent images which illustrate the characterization of induced pluripotent stem cell lines. FIG. 9b includes examples of karyotypic analysis of iPSC lines 3.5, 3.6 and 16.5.

FIG. 10 illustrates exemplary embodiments in accordance with the present invention. FIG. 10 a through 10g are microscopic images showing the morphologic comparison of hESC and iPSC organoid formation.

FIG. 11 illustrates exemplary embodiments in accordance with the present invention. FIGS. 11a through 11f are immunofluorescent images showing the molecular analysis of stages of epithelial growth, maturation and cytodifferentiation.

FIG. 12 illustrates exemplary embodiments in accordance with the present invention. FIGS. 12a and 12b are immunofluorescent images showing GATA factor expression in H9 hESC derived organoids and human iPSC derived organoids, respectively.

FIG. 13 illustrates exemplary embodiments in accordance with the present invention.

FIG. 14 illustrates exemplary embodiments in accordance with the present invention. FIG. 14A is a schematic illustration depicting the signaling network that regulates hindgut and intestinal development. FIGS. 14B through 14D are bar charts depicting the effects of FGF, WNT, and BMP signaling on differentiation of definitive endoderm into foregut and hindgut.

FIG. 15 illustrates exemplary embodiments in accordance with the present invention.

FIG. 16 illustrates exemplary embodiments in accordance with the present invention. FIGS. 16A and 16B are bar charts that depict BMP signaling in regulating formation of proximal and distal intestine formation from human embryonic and induced pluripotent stem cells.

DETAILED DESCRIPTION OF THE INVENTION

Definitions

Figure 1A:
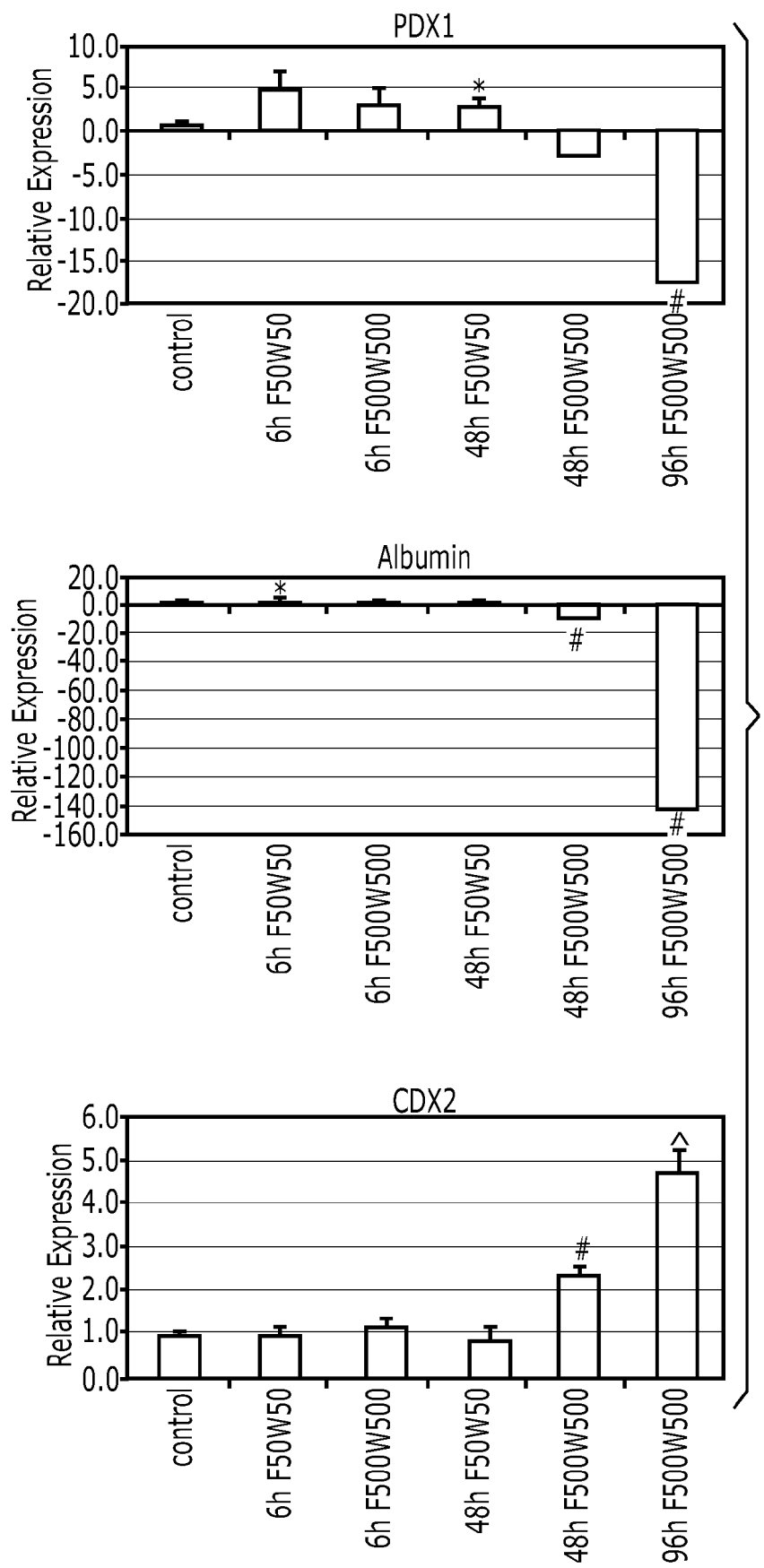
FIG. 1a includes bar charts that illustrate that FGF4 and Wnt3a act synergistically in a temporal and dose-dependent manner to specify stable posterior endoderm fate.

Unless otherwise noted, terms are to be understood according to conventional usage by those of ordinary skill in the relevant art.

As used herein, the term "totipotent stem cells" (also known as omnipotent stem cells) are stem cells that can differentiate into embryonic and extra-embryonic cell types. Such cells can construct a complete, viable, organism. These cells are produced from the fusion of an egg and sperm cell. Cells produced by the first few divisions of the fertilized egg are also totipotent.

As used herein, the term "pluripotent stem cells (PSCs)," also commonly known as PS cells, encompasses any cells that can differentiate into nearly all cells, i.e., cells derived from any of the three germ layers (germinal epithelium), including endoderm (interior stomach lining, gastrointestinal tract, the lungs), mesoderm (muscle, bone, blood, urogenital), and ectoderm (epidermal tissues and nervous system). PSCs can be the descendants of totipotent cells, derived from embryonic stem cells (including embryonic germ cells) or obtained through induction of a non-pluripotent cell, such as an adult somatic cell, by forcing the expression of certain genes.

As used herein, the term "induced pluripotent stem cells (iPSCs)," also commonly abbreviated as iPS cells, refers to a type of pluripotent stem cells artificially derived from a normally non-pluripotent cell, such as an adult somatic cell, by inducing a "forced" expression of certain genes.

As used herein, the term "embryonic stem cells (ESCs)," also commonly abbreviated as ES cells, refers to cells that are pluripotent and derived from the inner cell mass of the blastocyst, an early-stage embryo. For purpose of the present invention, the term "ESCs" is used broadly sometimes to encompass the embryonic germ cells as well.

As used herein, the term "precursor cell" encompasses any cells that can be used in methods described herein, through which one or more precursor cells acquire the ability to renew itself or differentiate into one or more specialized cell types. In some embodiments, a precursor cell is pluripotent or has the capacity to becoming pluripotent. In some embodiments, the precursor cells are subjected to the treatment of external factors (e.g., growth factors) to acquire pluripotency. In some embodiments, a precursor cell can be a totipotent (or omnipotent) stem cell; a pluripotent stem cell (induced or non-induced); a multipotent stem cell; an oligopotent stem cells and a unipotent stem cell. In some embodiments, a precursor cell can be from an embryo, an infant, a child, or an adult. In some embodiments, a precursor cell can be a somatic cell subject to treatment such that pluripotency is conferred via genetic manipulation or protein/peptide treatment.

In developmental biology, cellular differentiation is the process by which a less specialized cell becomes a more specialized cell type. As used herein, the term "directed differentiation" describes a process through which a less specialized cell becomes a particular specialized target cell type. The particularity of the specialized target cell type can be determined by any applicable methods that can be used to define or alter the destiny of the initial cell. Exemplary methods include but are not limited to genetic manipulation, chemical treatment, protein treatment, and nucleic acid treatment.

As used herein, the term "cellular constituents" are individual genes, proteins, mRNA expressing genes, and/or any other variable cellular component or protein activities such as the degree of protein modification (e.g., phosphorylation), for example, that is typically measured in biological experiments (e.g., by microarray or immunohistochemistry) by those skilled in the art. Significant discoveries relating to the complex networks of biochemical processes underlying living systems, common human diseases, and gene discovery and structure determination can now be attributed to the application of cellular constituent abundance data as part of the research process. Cellular constituent abundance data can help to identify biomarkers, discriminate disease subtypes and identify mechanisms of toxicity.

Figure 5A:
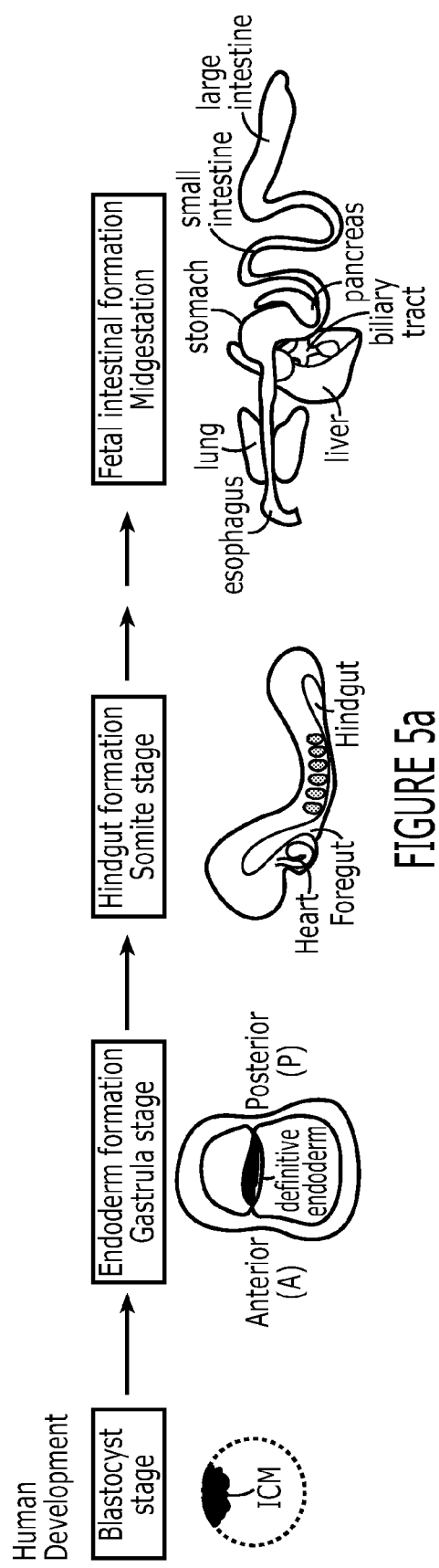
FIGS. 5a and 5b are schematic illustrations of human intestinal development and directed differentiation of PSCs into intestinal tissue, respectively.
Figure 5B:
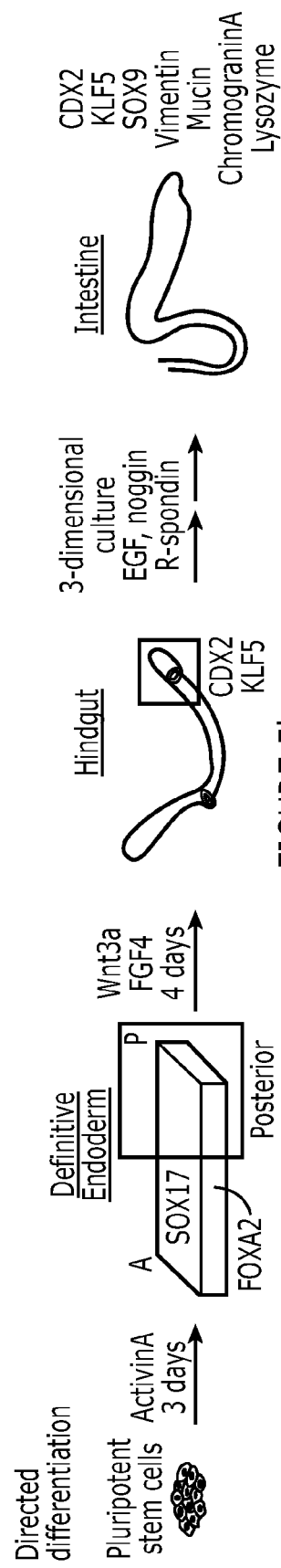

As described herein, methods and systems are established using a temporal series of growth factor manipulations to mimic embryonic intestinal development in culture. In particular, methods and systems are established to direct in vitro the differentiation of PSCs, both human embryonic stem cells (hESC) and induced pluripotent stem cells (iPSC), into intestinal tissue (for example, as depicted in FIGS. 5a and 5b). These factors directed human intestinal development in vitro in stages that approximate fetal gut development: activin-induced definitive endoderm (DE) formation; FGF/Wnt induced posterior endoderm pattering, hindgut specification and morphogenesis; and finally a pro-intestinal culture system that promoted intestinal growth, morphogenesis and cytodifferentiation into functional intestinal cell types including enterocytes, goblet, Paneth and enteroendocrine cells.

Pluripotent Stem Cells Derived from Embryonic Cells

In some embodiments, an important step is to obtain stem cells that are pluripotent or can be induced to become pluripotent. In some embodiments, pluripotent stem sells are derived from embryonic stem cells, which are in turn derived from totipotent cells of the early mammalian embryo and are capable of unlimited, undifferentiated proliferation in vitro. Embryonic stem cells are pluripotent stem cells derived from the inner cell mass of the blastocyst, an early-stage embryo. Methods for deriving embryonic stem cells from blastocytes are well known in the art. For example, three cell lines (H1, H13, and H14) had a normal XY karyotype, and two cell lines (H7 and H9) had a normal XX karyotype. Human embryonic stem cells H9 (H9-hESCs) are used in the exemplary embodiments described in the present application, but it would be understood by one of skill in the art that the methods and systems described herein are applicable to any stem cells.

Additional stem cells that can be used in embodiments in accordance with the present invention include but are not limited to those provided by or described in the database hosted by the National Stem Cell Bank (NSCB), Human Embryonic Stem Cell Research Center at the University of California, San Francisco (UCSF); WISC cell Bank at the Wi Cell Research Institute; the University of Wisconsin Stem Cell and Regenerative Medicine Center (UW-SCRMC); Novocell, Inc. (San Diego, Calif.); Cellartis AB (Goteborg, Sweden); ES Cell International Pte Ltd (Singapore); Technion at the Israel Institute of Technology (Haifa, Israel); and the Stem Cell Database hosted by Princeton University and the University of Pennsylvania. Exemplary embryonic stem cells that can be used in embodiments in accordance with the present invention include but are not limited to SA01 (SA001); SA02 (SA002); ES01 (HES-1); ES02 (HES-2); ES03 (HES-3); ES04 (HES-4); ES05 (HES-5); ES06 (HES-6); BG01 (BGN-01); BG02 (BGN-02); BG03 (BGN-03); TE03 (13); TE04 (14); TE06 (16); UC01 (HSF1); UC06 (HSF6); WA01 (H1); WA07 (H7); WA09 (H9); WA13 (H13); WA14 (H14).

In some embodiments, the stem cells are further modified to incorporate additional properties. Exemplary modified cell lines include but not limited to H1 OCT4-EGFP; H9 Cre-LoxP; H9 hNanog-pGZ; H9 hOct4-pGZ; H9 in GFPhES; and H9 Syn-GFP.

More details on embryonic stem cells can be found in, for example, Thomson et al., 1998, "Embryonic Stem Cell Lines Derived from Human Blastocysts," Science 282 (5391):1145-1147; Andrews et al., 2005, "Embryonic stem (ES) cells and embryonal carcinoma (EC) cells: opposite sides of the same coin," Biochem Soc Trans 33:1526-1530; Martin 1980, "Teratocarcinomas and mammalian embryogenesis,". Science 209 (4458):768-776; Evans and Kaufman, 1981, "Establishment in culture of pluripotent cells from mouse embryos," Nature 292(5819): 154-156; Klimanskaya et al., 2005, "Human embryonic stem cells derived without feeder cells," Lancet 365 (9471): 1636-1641; each of which is hereby incorporated herein in its entirety.

Alternative, pluripotent stem cells can be derived from embryonic germ cells (EGCs), which are the cells that give rise to the gametes of organisms that reproduce sexually. EGCs are derived from primordial germ cells found in the gonadal ridge of a late embryo, have many of the properties of embryonic stem cells. The primordial germ cells in an embryo develop into stem cells that in an adult generate the reproductive gametes (sperm or eggs). In mice and humans it is possible to grow embryonic germ cells in tissue culture under appropriate conditions. Both EGCs and ESCs are pluripotent. For purpose of the present invention, the term "ESCs" is used broadly sometimes to encompass EGCs.

Induced Pluripotent Stem Cells (iPSCs)

In some embodiments, iPSCs are derived by transfection of certain stem cell-associated genes into non-pluripotent cells, such as adult fibroblasts. Transfection is typically achieved through viral vectors, such as retroviruses. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic selection. As used herein, iPSCs include but are not limited to first generation iPSCs, second generation iPSCs in mice, and human induced pluripotent stem cells. In some embodiments, a retroviral system is used to transform human fibroblasts into pluripotent stem cells using four pivotal genes: Oct3/4, Sox2, Klf4, and c-Myc. In alternative embodiments, a lentiviral system is used to transform somatic cells with OCT4, SOX2, NANOG, and LIN28. Genes whose expression are induced in iPSCs include but are not limited to Oct-3/4 (e.g., Pou5fl); certain members of the Sox gene family (e.g., Sox1, Sox2, Sox3, and Sox15); certain members of the Klf family (e.g., Klf1, Klf2, Klf4, and Klf5), certain members of the Myc family (e.g., C-myc, L-myc, and N-myc), Nanog, and LIN28.

In some embodiments, non-viral based technologies are employed to generate iPSCs. In some embodiments, an adenovirus can be used to transport the requisite four genes into the DNA of skin and liver cells of mice, resulting in cells identical to embryonic stem cells. Since the adenovirus does not combine any of its own genes with the targeted host, the danger of creating tumors is eliminated. In some embodiments, reprogramming can be accomplished via plasmid without any virus transfection system at all, although at very low efficiencies. In other embodiments, direct delivery of proteins is used to generate iPSCs, thus eliminating the need for viruses or genetic modification. In some embodiment, generation of mouse iPSCs is possible using a similar methodology: a repeated treatment of the cells with certain proteins channeled into the cells via poly-arginine anchors was sufficient to induce pluripotency. In some embodiments, the expression of pluripotency induction genes can also be increased by treating somatic cells with FGF2 under low oxygen conditions.

More details on embryonic stem cells can be found in, for example, Kaji et al., 2009, "Virus free induction of pluripotency and subsequent excision of reprogramming factors," *Nature* 458:771-775; Woltjen et al., 2009, "piggyBac transposition reprograms fibroblasts to induced pluripotent stem cells," *Nature* 458:766-770; Okita et al., 2008, "Generation of Mouse Induced Pluripotent Stem Cells Without Viral Vectors," *Science* 322(5903):949-953; Stadtfeld et al., 2008, "Induced Pluripotent Stem Cells Generated without Viral Integration," *Science* 322(5903):945-949; and Zhou et al., 2009, "Generation of Induced Pluripotent Stem Cells Using Recombinant Proteins," *Cell Stem Cell* 4(5):381-384; each of which is hereby incorporated herein in its entirety.

In some embodiments, exemplary iPS cell lines include but not limited to iPS-DF19-9; iPS-DF19-9; iPS-DF4-3; iPS-DF6-9; iPS(Foreskin); iPS(IMR90); and iPS(IMR90).

It has been shown that iPSCs were capable of differentiation in a fashion similar to ESCs into fully differentiated tissues. For example, iPSCs were differentiated into neurons, expressing βIII-tubulin, tyrosine hydroxylase, AADC, DAT, ChAT, LMX1B, and MAP2. The presence of catecholamine-associated enzymes may indicate that iPSCs, like hESCs, may be differentiable into dopaminergic neurons. Stem cell-associated genes were shown to be down-regulated after differentiation. It was also shown that iPSCs were differentiated into cardiomyocytes that spontaneously began beating. Cardiomyocytes expressed TnTc, MEF2C, MYL2A, MYHCβ, and NKX2.5. Stem cell-associated genes were down-regulated after differentiation.

Intestinal Organ and Development

No systems were available prior to the present invention for converting embryonic stem cells and/or iPSCs into intestinal tissues. In anatomy, the intestine (or bowel) is the segment of the alimentary canal extending from the stomach to the anus and, in humans and other mammals, consists of two segments, the small intestine and the large intestine. In humans, the small intestine is further subdivided into the duodenum, jejunum and ileum while the large intestine is subdivided into the cecum and colon. The structure of an intestinal organ is described herein using the human organ as an example. It will be understood by one of ordinary skill in the art that the methods and systems described herein are applicable to the intestinal systems of all mammals.

The intestinal tract can be broadly divided into two different parts, the small and large intestine. Grayish-purple in color and about 35 millimeters (1.5 inches) in diameter, the small intestine is the first and longer, measuring 6 to 7 meters (20-23 feet) long average in an adult man. Shorter and relatively stockier, the large intestine is a dark reddish color, measuring roughly 1.5 meters (5 feet) long on average.

The lumen is the cavity where digested food passes through and from where nutrients are absorbed. Both intestines share a general structure with the whole gut, and are composed of several layers.

Going from inside the lumen radially outwards, one passes the mucosa (glandular epithelium and muscularis mucosa), submucosa, muscularis externa (made up of inner circular and outer longitudinal), and lastly serosa. Along the whole length of the gut in the glandular epithelium are goblet cells. These secrete mucus which lubricates the passage of food and protects the gut from digestive enzymes. Villi are vaginations of the mucosa and increase the overall surface area of the intestine while also containing a lacteal, which is connected to the lymph system and aids in the removal of lipids and tissue fluid from the blood supply. Microvilli are present on the epithelium of a villus and further increase the surface area over which absorption can take place. The muscularis mucosa is a layer of smooth muscle that aids in the action of continued peristalsis and catastalsis along the gut. The submucosa contains nerves (e.g., Meissner's plexus), blood vessels and elastic fibre with collagen that stretches with increased capacity but maintains the shape of the intestine. The muscularis externa comprises longitudinal and smooth muscle that again helps with continued peristalsis and the movement of digested material out of and along the gut. In between the two layers of muscle lies Auerbach's plexus. The serosa is made up of loose connective tissue and coated in mucus so as to prevent friction damage from the intestine rubbing against other tissue. Holding all this in place are the mesenteries which suspend the intestine in the abdominal cavity and stop it from being disturbed when a person is physically active.

In some embodiments, PSCs, such as ESCs and iPSCs, undergo directed differentiation in a step-wise manner first into definitive endoderm (DE) then into posterior/hindgut epithelium (e.g., hindgut spheroids), and then into intestinal tissue.

In some embodiments, PSCs, such as ESCs and iPSCs, undergo directed differentiation in a non step-wise manner where molecules (e.g., growth factors, ligands) for promoting DE formation and those for subsequent tissue formation are added at the same time.

Definitive Endoderm

The epithelium of the intestine is derived from a simple sheet of cells called the definitive endoderm (DE). The anterior DE forms the foregut and its associated organs including the liver and pancreas and the posterior DE forms the midgut and hindgut, which forms the small and large intestines and parts of the genitourinary system. Studies using mouse, chick and frog embryos suggest that establishing the anterior-posterior pattern in DE at the gastrula stage is a prerequisite for subsequent foregut and hindgut development. The Wnt and FGF signaling pathways are critical for this process and act to promote posterior endoderm and hindgut fate and suppress anterior endoderm and foregut fate. The simple cuboidal epithelium of the hindgut first develops into a pseudostratified columnar epithelium, then into villi containing a polarized columnar epithelium and a proliferative zone at the base of the villi, which corresponds with the presumptive progenitor domain.

A robust and efficient process is established to direct the differentiation of DE into intestinal tissue in vitro. In some embodiments, directed differentiation is achieved by selectively activating certain signaling pathways in the iPSCs and/or DE cells. In some embodiments, the signaling pathways are those active in intestinal development, including but not limited to the Wnt signaling pathway; Wnt/APC signaling pathway; FGF signaling pathway; TGF-beta signaling pathway; BMP signaling pathway; Notch signaling pathway; Hedgehog signaling pathway; LKB signaling pathway; and Par polarity signaling pathway.

Additional details of pathways relating to intestinal development in general are found in, for example, Sancho et al., 2004, "Signaling Pathways in Intestinal Development and Cancer," *Annual Review of Cell and Developmental Biology* 20:695-723; Logan and Nusse, 2004, "The Wnt Signaling Pathway in Development and Disease," *Annual Review of Cell and Developmental Biology* 20:781-810; Taipalel and Beachyl, 2001, "The Hedgehog and Wnt signalling pathways in cancer," *Nature* 411:349-354; Gregorieff and Clevers, 2005, "Wnt signaling in the intestinal epithelium: from endoderm to cancer," *Genes & Dev.* 19: 877-890; each of which is hereby incorporated by reference herein in its entirety.

More details on the functions of signaling pathways relating to DE development can be found in, for example, Zorn and Wells, 2009, "Vertebrate endoderm development and organ formation," *Annu Rev Cell Dev Biol* 25:221-251; Dessimoz et al., 2006, "FGF signaling is necessary for establishing gut tube domains along the anterior-posterior axis in vivo," *Mech Dev* 123:42-55; McLin et al., 2007, "Repression of Wnt/{beta}-catenin signaling in the anterior endoderm is essential for liver and pancreas development. Development," 134:2207-2217; Wells and Melton, 2000, *Development* 127:1563-1572; de Santa Barbara et al., 2003, "Development and differentiation of the intestinal epithelium," *Cell Mol Life Sci* 60(7): 1322-1332; each of which is hereby incorporated herein in its entirety.

Any methods for producing definitive endoderm from pluripotent cells (e.g., iPSCs or ESCs) are applicable to the methods described herein. In some embodiments, pluripotent cells are derived from a morula. In some embodiments, pluripotent stem cells are stem cells. Stem cells used in these methods can include, but are not limited to, embryonic stem cells. Embryonic stem cells can be derived from the embryonic inner cell mass or from the embryonic gonadal ridges. Embryonic stem cells or germ cells can originate from a variety of animal species including, but not limited to, various mammalian species including humans. In some embodiments, human embryonic stem cells are used to produce definitive endoderm. In some embodiments, human embryonic germ cells are used to produce definitive endoderm. In some embodiments, iPSCs are used to produce definitive endoderm.

In some embodiments, one or more growth factors are used in the differentiation process from pluripotent stem cells to DE cells. The one or more growth factors used in the differentiation process can include growth factors from the TGF-beta superfamily. In such embodiments, the one or more growth factors comprise the Nodal/Activin and/or the BMP subgroups of the TGF-beta superfamily of growth factors. In some embodiments, the one or more growth factors are selected from the group consisting of Nodal, Activin A, Activin B, BMP4, Wnt3a or combinations of any of these growth factors.

In some embodiments, the embryonic stem cells or germ cells and iPSCs are treated with the one or more growth factors for 6 or more hours; 12 or more hours; 18 or more hours; 24 or more hours; 36 or more hours; 48 or more hours; 60 or more hours; 72 or more hours; 84 or more hours; 96 or more hours; 120 or more hours; 150 or more hours; 180 or more hours; or 240 or more hours.

In some embodiments, the embryonic stem cells or germ cells and iPSCs are treated with the one or more growth factors at a concentration of 10 ng/ml or higher; 20 ng/ml or higher; 50 ng/ml or higher; 75 ng/ml or higher; 100 ng/ml or higher; 120 ng/ml or higher; 150 ng/ml or higher; 200 ng/ml or higher; 500 ng/ml or higher; 1,000 ng/ml or higher; 1,200 ng/ml or higher; 1,500 ng/ml or higher; 2,000 ng/ml or higher; 5,000 ng/ml or higher; 7,000 ng/ml or higher; 10,000 ng/ml or higher; or 15,000 ng/ml or higher. In some embodiments, concentration of the growth factor is maintained at a constant level throughout the treatment. In other embodiments, concentration of the growth factor is varied during the course of the treatment. In some embodiments, the growth factor is suspended in media that include fetal bovine serine (FBS) with varying HyClone concentrations. One of skill in the art would understand that the regimen described herein is applicable to any known growth factors, alone or in combination. When two or more growth factors are used, the concentration of each growth factor may be varied independently.

In some embodiments, populations of cells enriched in definitive endoderm cells are used. In some embodiments, the definitive endoderm cells are isolated or substantially purified. In some embodiments, the isolated or substantially purified definitive endoderm cells express the SOX17, FOXA2, and/or the CXRC4 marker to a greater extent than the OCT4, AFP, TM, SPARC and/or SOX7 markers.

Methods for enriching a cell population with definitive endoderm are also contemplated. In some embodiments, definitive endoderm cells can be isolated or substantially purified from a mixed cell population by contacting the cells with a reagent that binds to a molecule that is present on the surface of definitive endoderm cells but which is not present on the surface of other cells in the mixed cell population, and then isolating the cells bound to the reagent. In certain embodiments, the cellular constituent that is present on the surface of definitive endoderm cells is CXCR4.

Still other embodiments of the present invention relate to CXCR4 antibodies, SDF-1 ligands or other ligands for CXCR4 can be used to obtain definitive endoderm cells in an enriched, isolated or substantially purified form. For example, a CXCR4 antibody, an SDF-1 ligand or another ligand for CXCR4 can be used as a reagent in a method, such as affinity-based separation or magnetic-based separation, to enrich, isolate or substantially purify preparations of definitive endoderm cells that bind to the reagent.

In some embodiments of the present invention, definitive endoderm cells and hESCs are treated with one or more growth factors. Such growth factors can include growth factors from the TGF-beta superfamily. In such embodiments, the one or more growth factors comprise the Nodal/Activin and/or the BMP subgroups of the TGF-beta superfamily of growth factors. In some embodiments, the one or more growth factors are selected from the group consisting of Nodal, Activin A, Activin B, BMP4, Wnt3a or combinations of any of these growth factors.

Additional methods for obtaining or creating DE cells that can be used in the present invention include but are not limited to those described in U.S. Pat. No. 7,510,876 to D'Amour et al.; U.S. Pat. No. 7,326,572 to Fisk et al.; Kubol et al., 2004, "Development of definitive endoderm from embryonic stem cells in culture," Development 131:1651-1662; D'Amour et al., 2005, "Efficient differentiation of human embryonic stem cells to definitive endoderm," Nature Biotechnology 23:1534-1541; and Ang et al., 1993, "The formation and maintenance of the definitive endoderm lineage in the mouse: involvement of HNF3/forkhead proteins," *Development* 119:1301-1315; each of which is hereby incorporated by reference herein in its entirety.

Directed Differentiation of Posteriorized DE

In some embodiments, activin-induced definitive endoderm (DE) can further undergo FGF/Wnt induced posterior endoderm pattering, hindgut specification and morphogenesis, and finally a pro-intestinal culture system that promoted intestinal growth, morphogenesis and cytodifferentiation into functional intestinal cell types including enterocytes, goblet, Paneth and enteroendocrine cells. In some embodiments, human PSCs are efficiently directed to differentiate in vitro into intestinal epithelium that includes secretory, endocrine and absorptive cell types. It will be understood that molecules such as growth factors can be added to any stage of the development to promote a particular type of intestinal tissue formation.

In some embodiments, posteriorized endoderm cells of the DE are further developed into one or more specialized cell types.

In some embodiments, soluble FGF and Wnt ligands are used to mimic early hindgut specification in culture to convert, through directed differentiation, DE developed from iPSCs or ESCs into hindgut epithelium that efficiently gives rise to all the major intestinal cell types. In human, directed differentiation of DE is achieved through selective activating certain signaling pathways that are important to intestinal development.

Human intestinal development in vitro occurs in stages that approximate fetal gut development; endoderm formation, posterior endoderm patterning, hindgut morphogenesis, fetal gut development, epithelial morphogenesis, formation of a presumptive progenitor domain, and differentiation into functional cell types of the intestine. For example, in human, genes that encode Wnt signaling proteins include but are not limited to Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16.

It will be understood by one of skill in the art that altering the expression of any Wnt signaling protein in combination with any FGF ligand can give rise to directed differentiation in accordance of the present invention. In some embodiments, the alteration is over-expression of Wnt3, in particular Wnt3a. In some embodiments, the alternation is over-expression of Wnt1.

It will be understood by one of skill in the art that altering the signaling activity of the Wnt signaling pathway in combination with altering the signaling activity of the FGF signaling pathway can give rise to directed differentiation in accordance of the present invention. In some embodiments, the alteration is through the use of small molecule modulators that activate the aforementioned pathways. For example, Small molecule modulators of the Wnt pathway included, but is not limited to Lithium Chloride; 2-amino-4,6-disubstituted pyrimidine (hetero) arylpyrimidines; IQ1; QS11; NSC668036; DCA beta-catenin; 2-amino-4-[3,4-(methylenedioxy)-benzyl-amino]-6-(3-methoxyphenyl) pyrimidine.

In alternative embodiments, cellular constituents associated with the Wnt and/or FGF signaling pathways, for example, natural inhibitors or antagonist of the pathways can be inhibited to result in activation of the Wnt and/or FGF signaling pathways.

In some embodiment, the cellular constituents are inhibited by other cellular constituents or extrinsic molecules. Exemplary natural inhibitors of Wnt signaling include but are not limited to Dkk1, SFRP proteins and FrzB. In some embodiments, the extrinsic molecules includes but are not limited to small molecules such as WAY-316606; SB-216763; or BIO (6-bromoindirubin-3'-oxime).

More details are found, for example, in Liu et al., "A small-molecule agonist of the Wnt signaling pathway," *Angew Chem Int Ed Engl.* 44(13):1987-1990 (2005); Miyabayashi et al., "Wnt/beta-catenin/CBP signaling maintains long-term murine embryonic stem cell pluripotency," *Proc Natl Acad Sci USA.* 104(13):5668-5673 (2007); Zhang et al., "Small-molecule synergist of the Wnt/beta-catenin signaling pathway," *Proc Natl Acad Sci USA.* 104(18):7444-7448 (2007); Neiiendam et al., "An NCAM-derived FGF-receptor agonist, the FGL-peptide, induces neurite outgrowth and neuronal survival in primary rat neurons," *J. Neurochem.* 91(4):920-935 (2004); Shan et al., "Identification of a specific inhibitor of the dishevelled PDZ domain," *Biochemistry* 44(47):15495-15503 (2005); Coghlan et al., "Selective small molecule inhibitors of glycogen synthase kinase-3 modulate glycogen metabolism and gene transcription," *Chem. Biol.* 7(10):793-803 (2000); Coghlan et al., "Selective small molecule inhibitors of glycogen synthase kinase-3 modulate glycogen metabolism and gene transcription," *Chemistry & Biology* 7(10):793-803; and Pai et al., "Deoxycholic acid activates beta-catenin signaling pathway and increases colon cell cancer growth and invasiveness," *Mol Biol Cell.* 15(5):2156-2163 (2004); each of which is hereby incorporated by reference in its entirety.

In some embodiments, siRNA and/or shRNA targeting cellular constituents associated with the Wnt and/or FGF signaling pathways are used to activate these pathways. It would be understood by one of skill in the art that the target cellular constituents include but are not limited to SFRP proteins; GSK3, Dkk1, and FrzB.

More details about RNAi based technologies can be found, for example, in Couzin, 2002, *Science* 298:2296-2297; McManus et al., 2002, *Nat. Rev. Genet.* 3, 737-747; Hannon, G. J., 2002, *Nature* 418, 244-251; Paddison et al., 2002, *Cancer Cell* 2, 17-23; Elbashir et al., 2001. *EMBO J.* 20:6877-6888; Tuschl et al., 1999, *Genes Dev.* 13:3191-3197; Hutvagner et al., *Sciencexpress* 297:2056-2060; each of which is hereby incorporated by reference in its entirety.

Fibroblast growth factors (FGFs) are a family of growth factors involved in angiogenesis, wound healing, and embryonic development. The FGFs are heparin-binding proteins and interactions with cell-surface associated heparan sulfate proteoglycans have been shown to be essential for FGF signal transduction. FGFs are key players in the processes of proliferation and differentiation of wide variety of cells and tissues. In humans, 22 members of the FGF family have been identified, all of which are structurally related signaling molecules. Members FGF1 through FGF10 all bind fibroblast growth factor receptors (FGFRs). FGF1 is also known as acidic, and FGF2 is also known as basic fibroblast growth factor. Members FGF11, FGF12, FGF13, and FGF14, also known as FGF homologous factors 1-4 (FHF1-FHF4), have been shown to have distinct functional differences compared to the FGFs. Although these factors possess remarkably similar sequence homology, they do not bind FGFRs and are involved in intracellular processes unrelated to the FGFs. This group is also known as "iFGF." Members FGF16 through FGF23 are newer and not as well characterized. FGF15 is the mouse ortholog of human FGF19 (hence there is no human FGF15). Human FGF20 was identified based on its homology to *Xenopus* FGF-20 (XFGF-20). In contrast to the local activity of the other FGFs, FGF15/FGF19, FGF21 and FGF23 have more systemic effects.

In some embodiments, it will be understood by one of skill in the art that any of the FGFs can be used in conjunction with a protein from the Wnt signaling pathway. In some embodiments, soluble FGFs include and but are not limited to FGF4, FGF2, and FGF3.

In some embodiment, the cellular constituents of the FGF signaling pathway are inhibited by other cellular constituents or extrinsic molecules. Exemplary natural inhibitors of FGF signaling include but are not limited to the Sprouty family of proteins and the Spred family of proteins. As discussed above, proteins, small molecules, nucleic acids can be used to activating the FGF signaling pathway.

It will be understood by one of skill in the art that the methods and compositions described herein in connection with the Wnt and FGF signaling pathways are provided by way of examples. Similar methods and compositions are applicable to other signaling pathways disclosed herein.

In some embodiments, DE culture is treated with the one or more molecules of a signaling pathway described herein for 6 or more hours; 12 or more hours; 18 or more hours; 24 or more hours; 36 or more hours; 48 or more hours; 60 or more hours; 72 or more hours; 84 or more hours; 96 or more hours; 120 or more hours; 150 or more hours; 180 or more hours; 200 or more hours, 240 or more hours; 270 or more hours; 300 or more hours; 350 or more hours; 400 or more hours; 500 or more hours; 600 or more hours; 700 or more hours; 800 or more hours; 900 or more hours; 1,000 or more hours; 1,200 or more hours; or 1,500 or more hours.

In some embodiments, DE culture is treated with the one or more molecules of a signaling pathway described herein at a concentration of 10 ng/ml or higher; 20 ng/ml or higher; 50 ng/ml or higher; 75 ng/ml or higher; 100 ng/ml or higher; 120 ng/ml or higher; 150 ng/ml or higher; 200 ng/ml or higher; 500 ng/ml or higher; 1,000 ng/ml or higher; 1,200 ng/ml or higher; 1,500 ng/ml or higher; 2,000 ng/ml or higher; 5,000 ng/ml or higher; 7,000 ng/ml or higher; 10,000 ng/ml or higher; or 15,000 ng/ml or higher. In some embodiments, concentration of signaling molecule is maintained at a constant throughout the treatment. In other embodiments, concentration of the molecules of a signaling pathway is varied during the course of the treatment. In some embodiments, a signaling molecule in accordance with the present invention is suspended in media comprising DMEM and fetal bovine serine (FBS). The FBS can be at a concentration of 2% and more; 5% and more; 10% or more; 15% or more; 20% or more; 30% or more; or 50% or more. One of skill in the art would understand that the regiment described herein is applicable to any known molecules of the signaling pathways described herein, alone or in combination, including but not limited to any molecules in the Wnt and FGF signaling pathways.

In embodiments where two or more signaling molecules are used to treat the DE culture, the signaling molecules can be added simultaneously or separately. When two or more molecules are use, the concentration of each may be varied independently.

Differentiation of PSCs into DE culture and subsequently into various intermediate mature intestinal cell types can be determined by the presence of stage-specific cell markers. In some embodiments, expression of representative cellular constituents is used to determine DE formation. The representative cellular constituents include but are not limited to CMKOR1, CXCR4, GPR37, RTN4RL1, SLC5A9, SLC40A1, TRPA1, AGPAT3, APOA2, C20orf56, C21orf129, CALCR, CCL2, CER1, CMKOR1, CRIP1, CXCR4, CXorf1, DIO3, DIO30S, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192.

Additional cellular constituents suitable for detecting DE formation can be found in, for example, in U.S. patent application Ser. No. 11/165,305, filed Jun. 23, 2005; U.S. patent application Ser. No. 11/317,387, filed Dec. 22, 2005; U.S. patent Ser. No. 11/021,618, filed Dec. 23, 2004; U.S. patent application Ser. Nos. 11/021,618, 11/115,868 filed on Apr. 26, 2005; U.S. patent application Ser. No. 11/317,387, filed on Dec. 22, 2005; U.S. patent application Ser. No. 11/474,211, filed on Jun. 23, 2006; U.S. patent application Ser. No. 11/165,305, filed on Jun. 23, 2005; U.S. patent application Ser. No. 11/587,735 filed on Aug. 29, 2008; U.S. patent application Ser. No. 12/039,701, filed on Feb. 28, 2008; U.S. patent application Ser. No. 12/414,482, filed on Mar. 30, 2009; U.S. patent application Ser. No. 12/476,570, filed on Jun. 2, 2009; U.S. patent application Ser. No. 12/093,590 filed on Jul. 21, 2008; U.S. patent application Ser. No. 12/582,600 filed on Oct. 20, 2009; each of which is hereby incorporated by reference herein in its entirety.

In some embodiments, expression of CDX2 is used to reveal tendency of hindgut formation after DE have been incubated with FGF4 and Wnt3a for a period of time, for example, for 12 hours or longer; 18 hours or longer; 24 hours or longer; 36 hours or longer; 48 hours or longer; 60 hours or longer; or 90 hours or longer. In some embodiments, longer periods of incubation are needed to achieve a stable posterior endoderm phenotype as measured by prolonged expressed of CDX2. In such embodiments, the periods of incubation can be for 60 hours or longer; 72 hours or longer; 84 hours or longer; 96 hours or longer; 108 hours or longer; 120 hours or longer; 140 hours or longer; 160 hours or longer; 180 hours or longer; 200 hours or longer; 240 hours or longer; or 300 hours or longer.

Alternatively, in some embodiments, the absence of cellular constituents, such as foregut markers Pdx1 and Albumin, can be used to reveal directed hindgut formation. In some embodiments, intestinal transcription factors CDX2, KLF5 and SOX9 can be used to represent intestinal development. In some embodiments, GATA4 and/or GATA6 protein expression can be used to represent intestinal development. In these embodiments, the periods of incubation can be for 12 hours or longer; 18 hours or longer; 24 hours or longer; 36 hours or longer; 48 hours or longer; 60 hours or longer; or 90 hours or longer. Alternatively, the periods of incubation can be for 60 hours or longer; 72 hours or longer; 84 hours or longer; 96 hours or longer; 108 hours or longer; 120 hours or longer; 140 hours or longer; 160 hours or longer; 180 hours or longer; 200 hours or longer; 240 hours or longer; or 300 hours or longer.

In some embodiments, abundance data of cellular constituents, for example, protein and/or gene expression levels, are determined by immunohistochemistry using primary and/or secondary antibodies targeting molecules in the relevant signaling pathways. In other embodiments, abundance data of cellular constituents, for example, protein and/or gene expression levels, are determined by microarray analyses.

Still alternatively, morphological changes can be used to represent the progress of directed differentiation. In some embodiments, hindgut spheroids are further subject to 3-dimensional culture conditions for further maturation. In other embodiments, a highly convoluted epithelium surrounded by mesenchymal cells can be observed following hindgut spheroids formation. Additionally, intestinal organoids; polarized columnar epithelium; goblet cells; or smooth muscle cells can be observed in 6 days or longer; 7 days or longer; 9 days or longer; 10 days or longer; 12 days or longer; 15 days or longer; 20 days or longer; 25 days or longer; 28 days or longer; 32 days or longer; 36 days or longer; 40 days or longer; 45 days or longer; 50 days or longer; or 60 days or longer.

Directed Differentiation of Pluripotent Stem Cells

In some embodiments, pluripotent stem cells are converted into intestinal cell types via a "one step" process. For example, one or more molecules that can differentiate pluripotent stem cells into DE culture (e.g., ActivinA) are combined with additional molecules that can promote directed differentiation of DE culture (e.g., Wnt3a and FGF4) to directly treat pluripotent stem cells.

Utilities and Kits Embodiments

In some embodiments, intestinal tissue or related cell types described herein can be used to screen drugs for intestinal uptake and mechanisms of transport. For example, this can be done in a high throughput manner to screen for the most readily absorbed drugs, and can augment Phase 1 clinical trials that are done to study drug intestinal uptake and intestinal toxicity. This includes pericellular and intracellular transport mechanisms of small molecules, peptides, metabolites, salts.

In some embodiments, intestinal tissue or related cell types described herein can be used to identify the molecular basis of normal human intestinal development.

In some embodiments, intestinal tissue or related cell types described herein can be used to identify the molecular basis of congenital defects affecting human intestinal development.

In some embodiments, intestinal tissue or related cell types described herein can be used to correct intestinal congenital defects caused by genetic mutations. In particular, mutation affecting human intestinal development can be corrected using iPSC technology and genetically normal Intestinal tissue or related cell types described herein. In some embodiments, intestinal tissue or related cell types described herein can be used to generate replacement tissue. Examples of genetic diseases include but are not limited to Neurog3 mutations and Enteric anendocrinosis, PTF1a mutations and neonatal diabetes, PDX1 mutations that effect enteroendocrine cells of the intestine.

In some embodiments, intestinal tissue or related cell types described herein can be used to generate replacement intestinal tissue for Inflamatory Bowel Disease (IBD), Crohn's Disease, Short Gut syndrome, intestinal cancer patients.

In some embodiments, intestinal tissue or related cell types described herein can be used to study microbiotic interactions with the human host epithelium and host immunity.

In some embodiments, intestinal tissue or related cell types described herein, in particular the enteroendocrine cells can be used to study hormonal regulation of feeding behavior, metabolism, mediated by intestinal endocrine hormones, for example the incretin response.

In some embodiments, intestinal tissue or related cell types described herein, in particular the enteroendocrine cells that produce the hormone GLP-1 can be used to study and improve pancreatic beta-cell mass and function and for treatment of diabetes.

In some embodiments, intestinal tissue or related cell types described herein can be used to replace any damaged or removed intestinal tissue such as that removed from colon cancer.

In some embodiments, intestinal tissue or related cell types described herein can be used to screen for toxicity and efficacy of any drug that acts on the intestine, for example, for diarrhea drugs, drugs that regulate secretion and absorption of the intestinal epithelium.

In some embodiments where intestinal tissue or related cell types described herein are used to determine the absorption level of a compound, the compound will be contacted with the intestinal cells or tissues with a compound; and a level of absorption of the compound by the intestinal cells or tissues detecting can be quantified. In some embodiments, the compound is labeled with a radio-isotope, a fluorescent label and or a primary or secondary visible marker.

In some embodiments, a diagnostic kit or package is developed to include the intestinal tissue or related cell types described herein and based on one or more of the aforementioned utilities.

Additional Embodiments Based on Microarray Analysis

In some embodiments, a reverse-engineering type of approach is taken to achieve directed differentiation of pluripotent stem cells. For example, microarray analyses of human ESCs, iPSCs and DE cultures, in both differentiated and undifferentiated states, are performed to identify cellular constituents that are differentially expressed in these different cell types. In some embodiments, only cellular constituents that are differentially expressed above a pre-determined level are identified as target cellular constituents. In particular, genes that are significantly differentially expressed are identified as targets. In some embodiments, significant differential expression occurs when a cellular constituent in a differentiated state in a particular cell type (e.g., as ESCs, iPSCs and DE) is expressed more than n folds than the expression level of the same cellular constituent in an undifferentiated state in the same cell type. In some embodiments, n is equal or greater than 2; equal or greater than 3; equal or greater than 5; equal or greater than 7; equal or greater than 10; equal or greater than 15; equal or greater than 18; equal or greater than 20; equal or greater than 23; or equal or greater than 28.

In some embodiments, selected cellular constituents from Table 2 are used as the target cellular constituents. For example, one or more cellular constituents that are differentially expressed above a pre-determined level are identified as target cellular constituents. In some embodiments, molecules capable of modulating the abundance levels of the target cellular constituents are used to treat cells at a certain development stage in order to achieve the desired directed differentiation results. In some embodiments, the target cellular constituents comprise 3 or more cellular constituents from Table 2; 5 or more cellular constituents from Table 2; 6 or more cellular constituents from Table 2; 8 or more cellular constituents from Table 2; 10 or more cellular constituents from Table 2; 12 or more cellular constituents from Table 2; 15 or more cellular constituents from Table 2; 18 or more cellular constituents from Table 2; 20 or more cellular constituents from Table 2; or 25 or more cellular constituents from Table 2.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Directing Hindgut Development of PSCs

Maintenance of PSCs.

Human embryonic stem cells and induced pluripotent stem cells were maintained on Matrigel (BD Biosciences) in mTesR1 media. Cells were passaged approximately every 5 days, depending on colony density. To passage PSCs, they were washed with DMEM/F12 media (no serum)(Invitrogen) and incubated in DMEM/F12 with 1 mg/mL dispase (Invitrogen) until colony edges started to detach from the dish. The dish was then washed 3 times with DMEM/F12 media. After the final wash, DMEM/F12 was replaced with mTesR1. Colonies were scraped off of the dish with a cell scraper and gently triturated into small clumps and passaged onto fresh Matrigel-coated plates.

Differentiation of PSCs into Definitive Endoderm (DE).

Differentiation into Definitive Endoderm was carried out as previously described. Briefly, a 3 day ActivinA (R&D systems) differentiation protocol was used. Cells were treated with ActivinA (100 ng/ml) for three consecutive days in RPMI 1640 media (Invitrogen) with increasing concentrations of 0%, 0.2%, 2% HyClone defined FBS (dFBS) (Thermo Scientific).

Differentiation of DE in Permissive Media (Differentiation Protocol for FIG. 1).

After differentiation into definitive endoderm, cells were incubated in DMEM/F12 plus 2% defined fetal bovine serum (dFBS) with either 0, 50, or 500 ng/ml of FGF4 and/or 0, 50, or 500 ng/ml of Wnt3a (R&D Systems) for 6, 48, or 96 hours. Cultures were then grown in permissive media consisting of DMEM plus 10% fetal bovine serum (FBS) for an additional 7 days.

Directing Hindgut Development of PSCs.

Figure 6A:
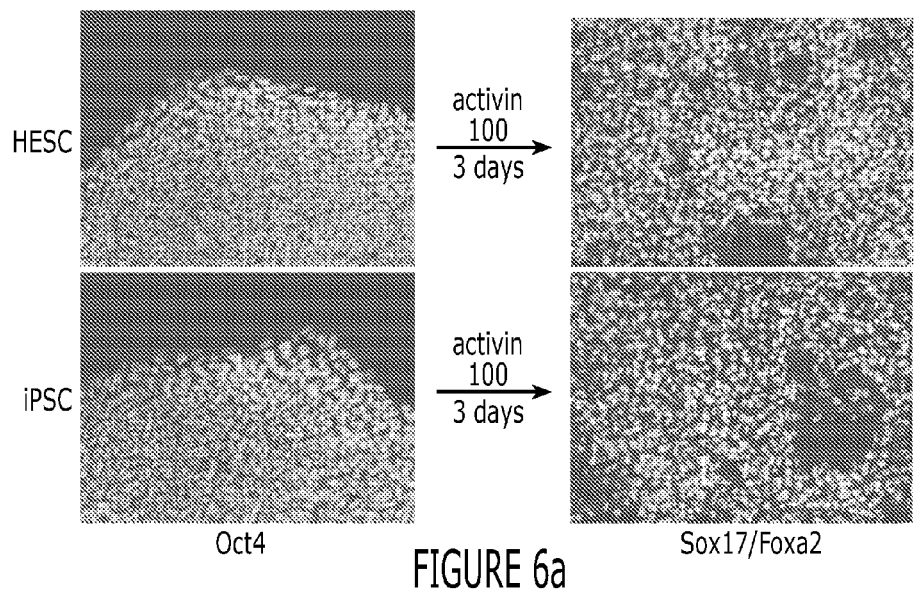
FIG. 6a includes immunofluorescent images depicting characterization of DE formation from hESC and iPSC lines.

As a first step to generating intestinal tissue, nodal-related TGFβ molecule activinA was used to promote differentiation of PSCs into DE as previously published. Activin-mediated differentiation routinely resulted in up to 90% of the cells co-expressing the DE markers SOX17 and FOXA2 (FIG. 6a). A robust activation of the DE transcriptional program (FIG. 6b and Table 2) was observed by using microarray analysis. It was also observed that cultures treated with activinA for only 3-days were competent to develop into both foregut (Albumin+ and Pdx1+) and hindgut (Cdx2) lineages when cultured for seven days in permissive conditions (FIG. 1b, control). In contrast, prolonged activin treatment for 4-5 days (common in many protocols) resulted in DE cultures that were intrinsically anterior in character and not as competent to form posterior lineages.

After the window of time when DE fate was plastic was identified, growth factors that are known to posteriorize endoderm, Wnt3a and FGF4, were used to direct the DE into a hindgut lineage. While neither factor alone was sufficient to robustly promote a posterior fate we determined that high concentrations of both FGF4+Wnt3a (500 ng/ml each) were able to induce robust expression of the hindgut marker CDX2 in the DE after 24-48 hours (FIG. 7). However 48 hours of FGF4+Wnt3a treatment was not sufficient to induce stable posterior, hindgut identity since CDX2 expression was not maintained and anterior fates, as measured by Pdx1 and Albumin expression, persisted following growth factor removal (FIG. 1a, c). In contrast, 96 hours of exposure to FGF4+Wnt3a conferred a stable posterior endoderm phenotype following growth factor removal with maintained CDX2 expression and complete absence of anterior markers (FIGS. 1a and d). Thus prolonged activity of FGF4 and Wnt3a resulted in a robust posteriorization of DE into CDX2+ hindgut endoderm.

Figure 2A:
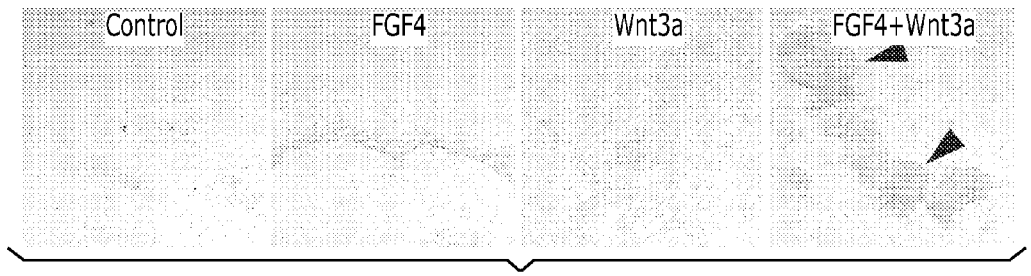
Figure 2B:
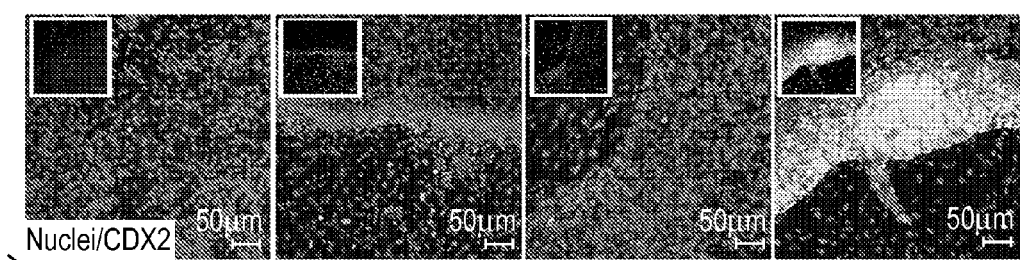
Figure 2C:
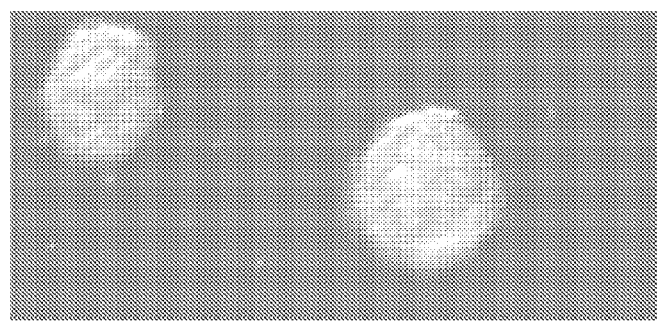
FIG. 2c includes bright field images of hindgut-like spheroids.
Figure 2D:
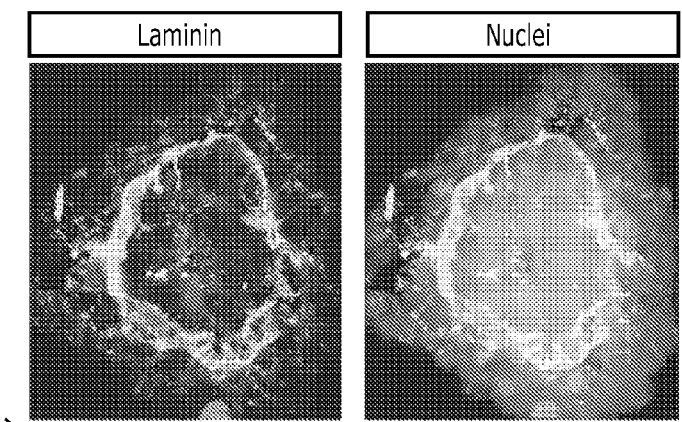
FIGS. 2d through 2f shows immunofluorescent images of CDX2, basal-lateral lamina ("laminin") and E-Cadherin expression in hindgut-like spheroids.
Figure 2E:
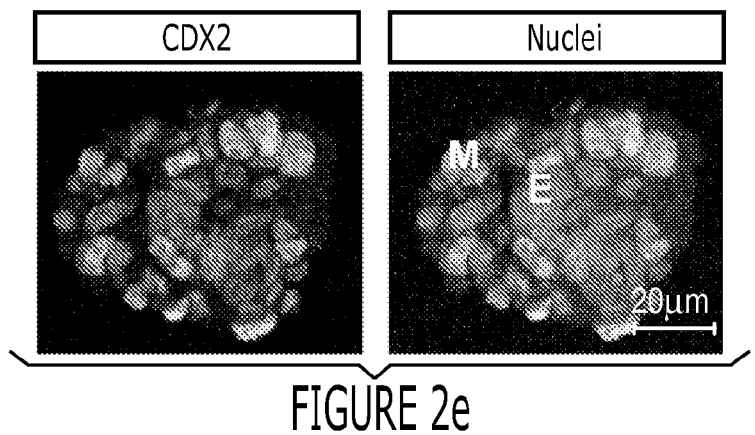
Figure 2F:
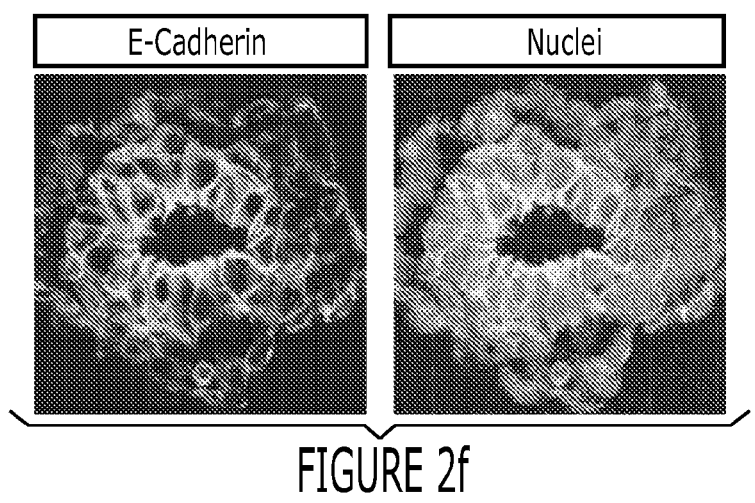
Figure 2G:
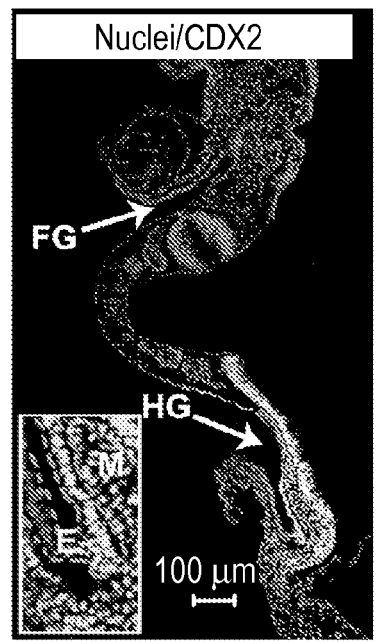
FIG. 2g is an immunofluorescent image of CDX2 expression in an e8.5 mouse embryo (sagittal section).
Figure 2H:
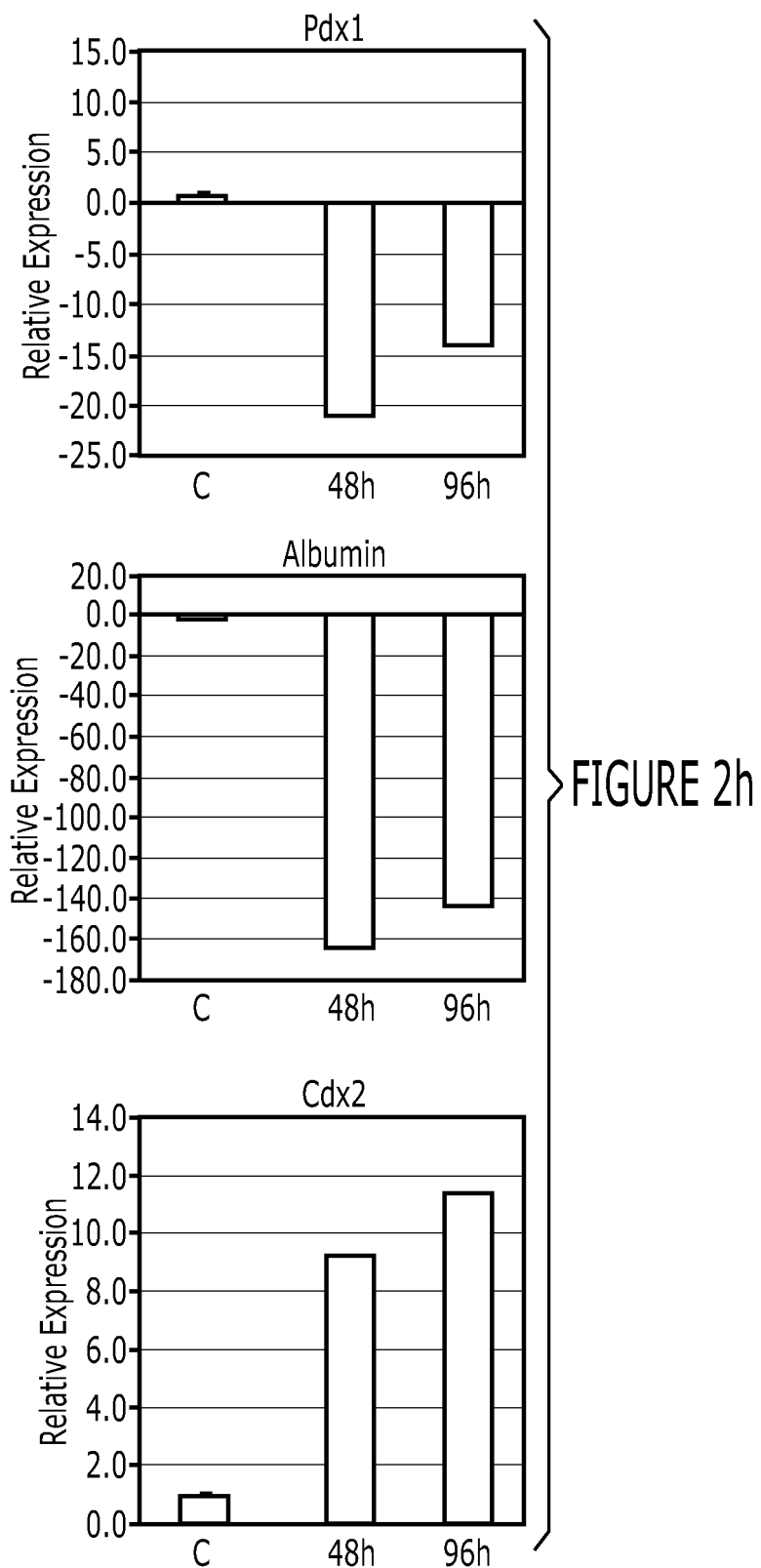
FIG. 2h includes bar charts that illustrate RT-qPCR analysis of hindgut-like spheroids for Pdx1, Albumin and CDX2 expression.

Not only were the molecular features of hindgut formation in vitro similar to hindgut development in vivo, FGF4+Wnt3a treated cultures underwent a morphogenesis similar to embryonic gut tube formation. Between 2 and 5 days of FGF4+Wnt3a treatment, flat cell sheets condensed into CDX2+ epithelial tubes, many of which budded off to form floating hindgut spheroids (FIG. 2a-c, FIG. 10a-10f) (Table 2a). Spheroids (FIG. 2c-f) were similar to e8.5 mouse hindgut (FIG. 2g) containing CDX2+ polarized epithelium (E) surrounded by CDX2+ mesenchyme (M). Spheroids were completely devoid of Alb- and Pdx1-expressing foregut cells (FIG. 2h). This in vitro gut-tube morphogenesis was never observed in control or Wnt3a-only treated cultures and FGF4 treated cultures generated 4-10 fold fewer spheroids (Table 1A), which were weakly CDX2+ and did not undergo further expansion. The similarity of the hindgut spheroids to mouse embryonic hindgut suggests that the morphological differentiation induced by FGF4+Wnt3 is a key event in the specification of the intestinal lineage.

The following tables illustrate the effects of growth factor treatment of hESCs and iPSCs. Generation of hindgut spheroids was tracked for (Table 1A) days 2-5 following growth factor treatment for H9 hESCs or (Table 1B) days 2-4 of growth factor treatment for iPSCs. Definitive endoderm was treated with either 500 ng/ml of FGF4 alone or 500 ng/ml of FGF4+Wnt3a. For both HESCs and iPSCs, hindgut spheroids formed much more robustly under FGF4+Wnt3a conditions. Control cultures or ones treated with Wnt3a alone never formed spheroids. Over the course of 4 days, FGF4+Wnt3a treated H9 endoderm generated an average of 4.5 fold more spheroids than that treated with FGF4 alone. Similarly, FGF4+Wnt3a treated iPSC endoderm generated an average of 7.25 fold more spheroids than that treated with FGF4 alone.

TABLE 1A

Growth factor treatment of hESCs: frequency of spheroid formation from hESC-H9.

| Days of GF treatment (H9 hESCs) | Total # organoids FGF4 treated (# organoids/ wells counted) | Average # organoids per well FGF4 treated | Total # organoids FGF4 + Wnt3a treated (# organoids/wells counted) | Average # organoids per well FGF4 + Wnt3a treated |
|---|---|---|---|---|
| 2 days (48 h) | 0/5 | 0 | 10/10 | 1 |
| 3 days (72 h) | 0/5 | 0 | 150/10 | 15 |

TABLE 1A-continued

Growth factor treatment of hESCs: frequency of spheroid formation from hESC-H9.

| Days of GF treatment (H9 hESCs) | Total # organoids FGF4 treated (# organoids/ wells counted) | Average # organoids per well FGF4 treated | Total # organoids FGF4 + Wnt3a treated (# organoids/wells counted) | Average # organoids per well FGF4 + Wnt3a treated |
|---|---|---|---|---|
| 4 days (96 h) | 44/5 | 8.8 | 322/10 | 32.2 |
| 5 days (120 h) | 19/4 | 4.75 | 100/8 | 12.5 |

TABLE 1B

Growth factor treatment of iPSCs: frequency of spheroid formation from iPSC-3.5.

| Days of GF treatment (iPSCs) | Total # organoids FGF4 treated (# organoids/ wells counted) | Average # organoids per well FGF4 treated | Total # organoids FGF4 + Wnt3a treated (# organoids/wells counted) | Average # organoids per well FGF4 + Wnt3a treated |
|---|---|---|---|---|
| 2 days (48 h) | 0/4 | 0 | 0/10 | 0 |
| 3 days (72 h) | 10/4 | 2.5 | 229/10 | 22.9 |
| 4 days (96 h) | 14/4 | 3.5 | 206/10 | 20.6 |

Frequencies of spheroid formation in response to FGF4 and Wnt3a were studied, as shown in Tables 1A and 1B. Generation of hindgut spheroids was tracked for days 2-5 of growth factor treatment (H9 hESCs, Table 1A) or days 2-4 of growth factor treatment (iPSCs, Table 1B) for endoderm being given either 500 ng/ml FGF4 alone or 500 ng/ml FGF4+Wnt3a. In both cell lines, hindgut spheroids were much more robustly generated in FGF4+Wnt3a conditions. Over the course of 4 days, FGF4+Wnt3a treated H9 endoderm generated an average of 4.5 fold more spheroids than FGF4 treated alone. Similarly, FGF4+Wnt3a treated iPSC endoderm generated an average of 7.25 fold more spheroids than FGF4 treated alone.

Not only were the molecular features of hindgut formation in vitro similar to hindgut development in vivo, FGF4+Wnt3a treated cultures underwent a morphogenesis similar to embryonic gut tube formation. Between 2 and 5 days of FGF4+Wnt3a treatment, flat cell sheets condensed into CDX2+ epithelial tubes, many of which budded off to form floating hindgut spheroids (FIG. 2a-c, FIG. 10a-f) (table 1A). Spheroids (FIG. 2c-f) were similar to e8.5 mouse hindgut (FIG. 2g) containing CDX2+ polarized epithelium (E) surrounded by CDX2+ mesenchyme (M). Spheroids were completely devoid of Alb- and Pdx1-expressing foregut cells (FIG. 2h). This in vitro gut-tube morphogenesis was not observed in control or Wnt3a-only treated cultures and FGF4 treated cultures generated 4-10 fold fewer spheroids (Table 1A), which were weakly CDX2+ and did not undergo further expansion (not shown). The similarity of the hindgut spheroids to mouse embryonic hindgut suggests that the morphological differentiation induced by FGF4+Wnt3 is a key event in the specification of the intestinal lineage.

More details can be found in, for example, D'Amour, K. A., et al. Efficient differentiation of human embryonic stem cells to definitive endoderm. *Nat Biotechnol* 23, 1534-1541 (2005); Beck, F., Erler, T., Russell, A. & James, R. Expression of Cdx-2 in the mouse embryo and placenta: possible role in patterning of the extra-embryonic membranes. *Dev Dyn* 204, 219-227 (1995); Dessimoz, J., Opoka, R., Kordich, J. J., Grapin-Botton, A. & Wells, J. M. FGF signaling is necessary for establishing gut tube domains along the anterior-posterior axis in vivo. *Mech Dev* 123, 42-55 (2006); McLin, V. A., Rankin, S. A. & Zorn, A. M. Repression of Wnt/{beta}-catenin signaling in the anterior endoderm is essential for liver and pancreas development. *Development* 134, 2207-2217 (2007); Wells, J. M. & Melton, D. A. Early mouse endoderm is patterned by soluble factors from adjacent germ layers. *Development* 127, 1563-1572. (2000); each of which is incorporated herein in its entirety.

FIGS. 1a through 1d illustrate exemplary embodiments of the present invention. FGF4 and Wnt3a act synergistically in a temporal and dose-dependent manner to specify stable posterior endoderm fate. ActivinA (100 ng/ml) was used to differentiate H9-HES cells into definitive endoderm (DE). DE was treated with the posteriorizing factors FGF4 (50, 500 ng), Wnt3a (50, 500 ng) or both for 6, 48 or 96 hours. Cells were then cultured in a permissive medium without growth factors for an additional seven days and analyzed for expression of foregut markers (ALB, PDX1) and the hindgut marker (CDX2) by RT-qPCR (a) and immunofluorescence (b-d). FGF4/Wnt-mediated changes in marker expression in (a) is relative to 3-day activin treated DE cultures that were grown for identical lengths of time in the absence of FGF4 or Wnt3a (control). Only high levels of FGF4+Wnt3a for 96 hours gave cultures with stable CDX2 expression that lack foregut marker expression. Error bars denote standard deviation of triplicates. Significance is shown by; *($p<0.05$), ^ ($p<0.001$), # ($p<0.0001$).

FIGS. 2a through 2h illustrate exemplary embodiments in accordance with the present invention in which posterior endoderm is shown developing into 3-dimensional, hindgut-like organoids. Morphogenesis of posterior endoderm into three-dimensional, hindgut-like organoids is depicted. (a) Bright field images of DE that was treated with FGF4+Wnt3a 96 hours formed numerous 3D epithelial structures including tubes and free-floating spheres (black arrows) relative to control DE, Wnt3a or FGF4 cultures (see Table 1A and 1B). (b) CDX2 immunostaining (Green) and nuclear stain (Draq5-blue) on cultures shown in (a). 3D structures in FGF4+Wnt3a treated cultures were largely CDX2 positive. Insets—green channel only showing CDX2 staining (c) Bright field image of hindgut-like spheroids. (d-f) Analysis of CDX2, basal-lateral lamina and E-Cadherin expression demonstrate that spheroids contain an inner layer of polarized, cuboidal, CDX2 positive epithelium surrounded by non-polarized mesenchyme-like CDX2 cells. (g) CDX2 expression in an e8.5 mouse embryo (sagittal section) shows that both hindgut endoderm (E) and adjacent mesenchyme (M) are CDX2 positive (green), similar to hindgut spheroids (Inset shows a magnified view of CDX2 staining in the hindgut endoderm and mesoderm; FIG—foregut, HG—hindgut. (h) RT-qPCR analysis of hindgut-like spheroids did not detect foregut markers (PDX1, Albumin) but detected robust expression of hindgut markers (CDX2). Expression levels shown in (h) is relative to 3-day activin treated DE cultures that were grown for identical lengths of time in the absence of FGF4 or Wnt3a (C=control; 48 h=spheroids generated after 48 hours; 96 h=spheroids generated after 96 hours). Error bars denote standard deviation of triplicates.

Figure 7A:
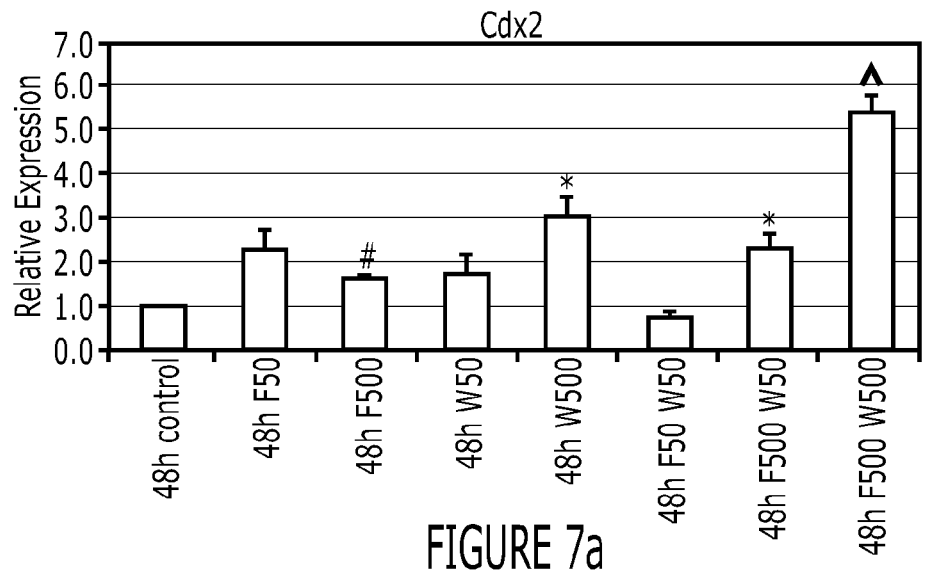
Figure 7B:
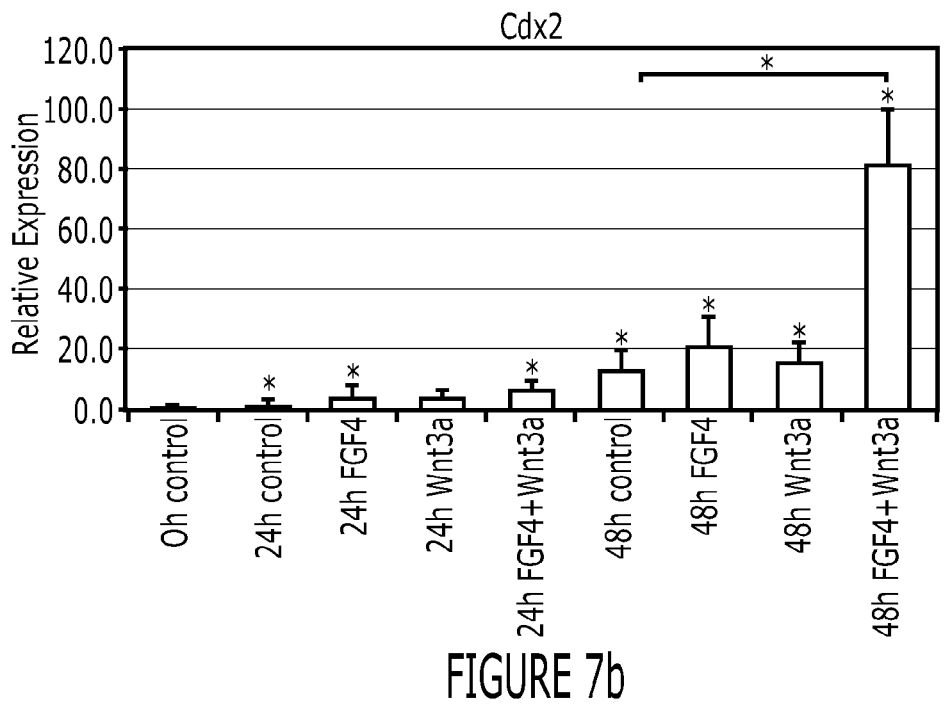

FIGS. 7a and 7b illustrate exemplary embodiments in accordance with the present invention, depicting time and concentration dependent induction of CDX2 by FGF4 and Wnt3a. (a) FGF4 and Wnt3a up-regulate CDX2 in a concentration dependant manner. 3-day ActivinA treated hESCs were treated for 48 hours with Wnt3a at 50 ng/ml or 500 ng/ml or FGF4 at 50 ng/ml or 500 ng/ml, or increasing concentrations of FGF4+Wnt3a. Cells were analyzed after 48 hours of treatment. FGF4 or Wnt3a alone caused modest changes in CDX2 expression at different doses. FGF4+ Wnt3a at the highest dose (500 ng/ml each) induced robust CDX2 expression. CDX2 expression was normalized to the internal control beta-tubulin, and is shown relative to a 48 hour control cultured in the absence of growth factors. (b) FGF4 and Wnt3a up-regulate CDX2 in a time dependant manner. 48 hours of exposure to FGF4+Wnt3a was required for the most robust induction of CDX2. All time points shown are set relative to a 0 hour no growth factor control. 500 ng/ml of FGF4, Wnt3a or FGF4+Wnt3a was used for all time points. Note that 24 hour and 48 controls, in the absence of growth factors, show a significant and spontaneous up-regulation of CDX2. Error bars denote standard deviation of triplicates. Significance is shown by; *($p<0.05$)

Example 2

Directing Hindgut Spheroids into Intestinal Tissue In Vitro

Directed Differentiation into Hindgut and Intestinal Organoids.

After differentiation into definitive endoderm, cells were incubated in 2% dFBS-DMEM/F12 with either 50 or 500 ng/ml FGF4 and/or 50 or 500 ng/ml Wnt3a (R&D Systems) for 2-4 days. After 2 days with treatment of growth factors, 3-dimensional floating spheroids were present in the culture. 3-dimensional spheroids were transferred into an in vitro system previously described to support intestinal growth and differentiation. Briefly, spheroids were embedded in Matrigel (BD Bioscience #356237) containing 500 ng/ml R-Spondin1 (R&D Systems), 100 ng/ml Noggin (R&D Systems) and 50 ng/ml EGF (R&D Systems). After the Matrigel solidified, media (Advanced DMEM/F12 (Invitrogen) supplemented with L-Glutamine, 10 μM Hepes, N2 supplement (R&D Systems), B27 supplement (Invitrogen), and Pen/Strep containing growth factors was overlaid and replaced every 4 days.

Directing Hindgut Spheroids into Intestinal Tissue In Vitro.

Figure 3A:
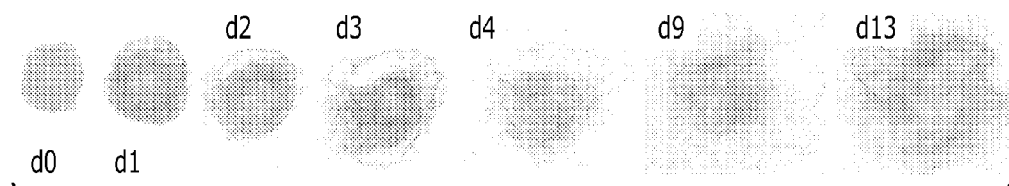
FIG. 3a includes images that illustrate the time course of organoid growth for 13 days.
Figure 3B:
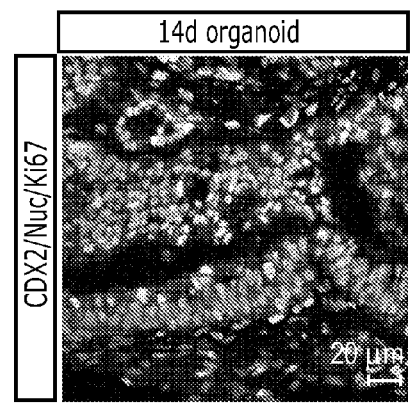
FIGS. 3b through 3e are immunofluorescent images of characteristic intestinal transcription factor expression and cell proliferation in organoids after 14 and 28 days of culture.
Figure 3C:
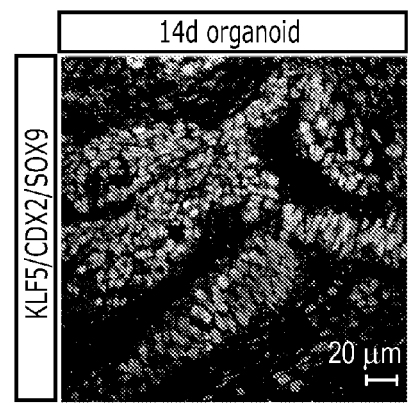
Figure 3D:
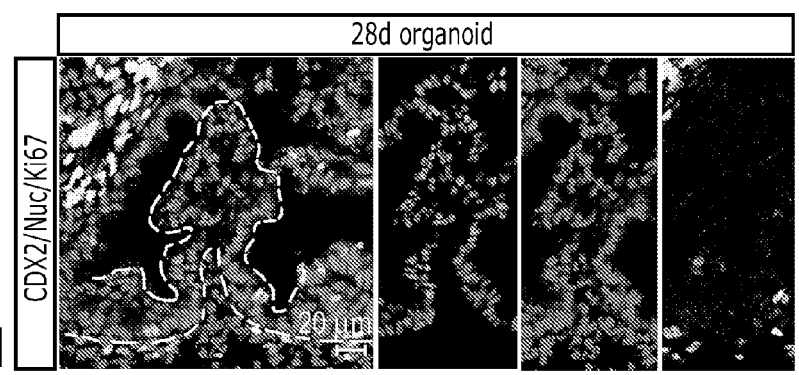
Figure 3E:
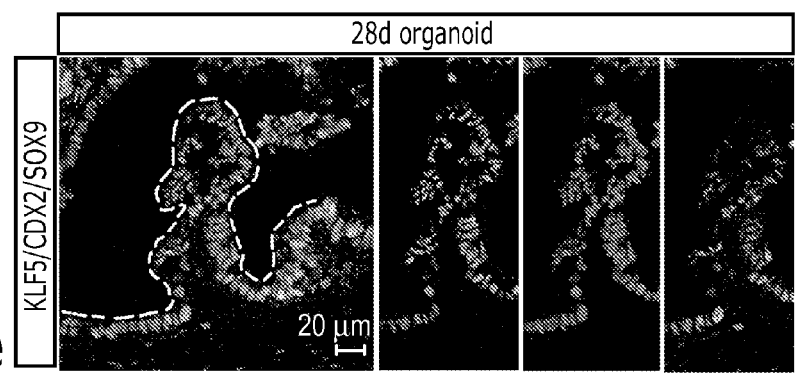
Figures 3F, 3G:
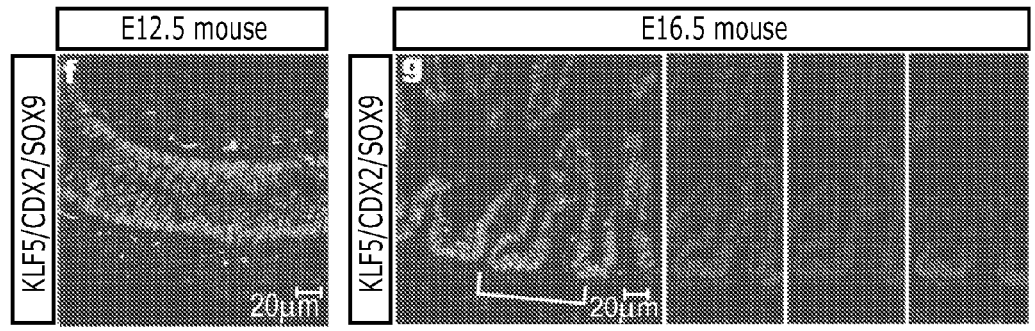
FIGS. 3f and 3g are immunofluorescent images of KLF5, CDX2 and SOX9 expression in mouse fetal intestine at e14.5.
Figure 8:
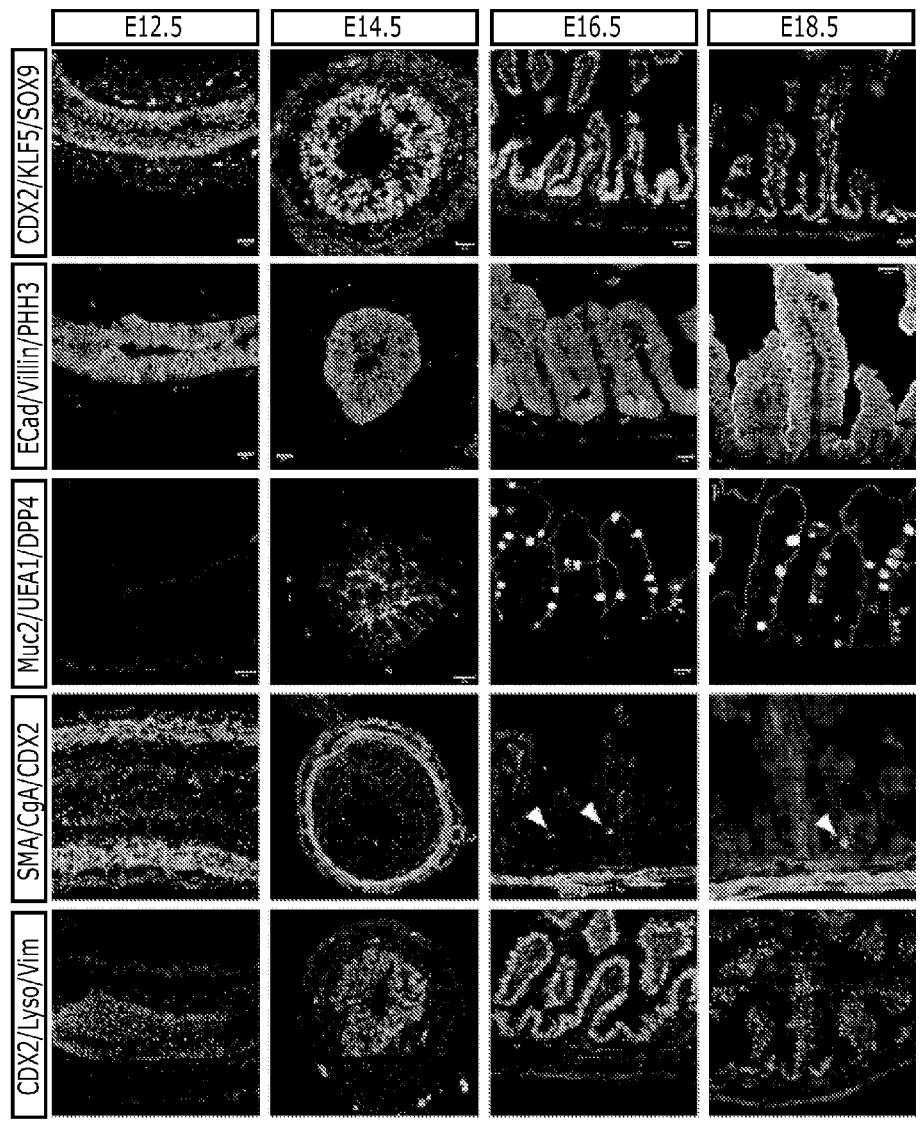
FIG. 8 includes immunofluorescent images illustrating exemplary embodiments in accordance with the present invention. The images depict molecular marker expression during mouse intestinal development at embryonic stages include e12.5, e14.5, e16.5 and e18.5.
Figure 11I:
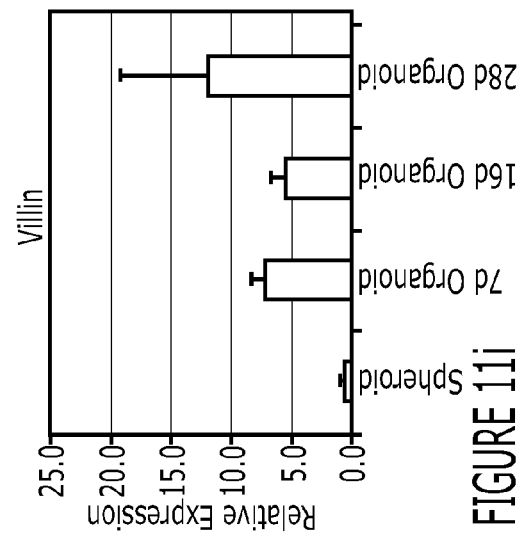
FIGS. 11g through 11m are bar charts of RT-qPCR results illustrating quantitative analysis of intestinal markers SOX9, Villin (enterocytes), Lysozyme (Paneth cells), HOXA13, IFABP (enterocytes) and MMPI (Paneth cells) during intestinal organoid development by RT-qPCR.
Figure 11H:
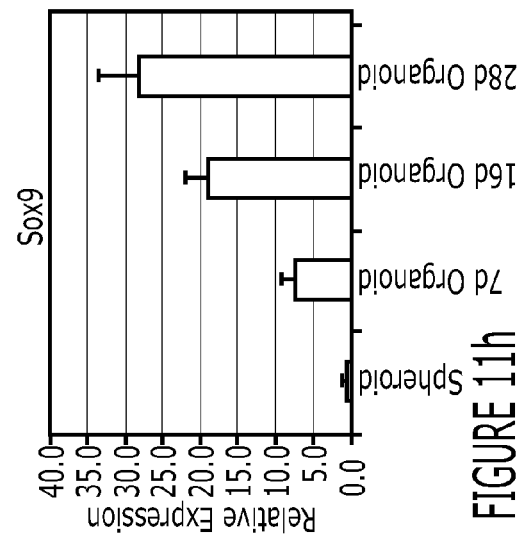
Figure 11F:
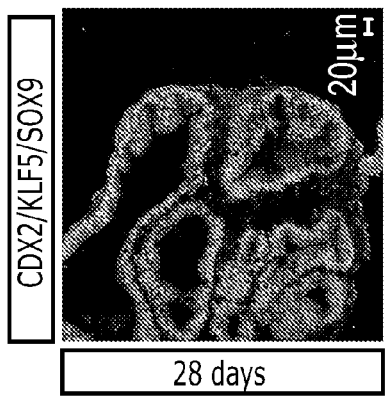
Figure 11E:
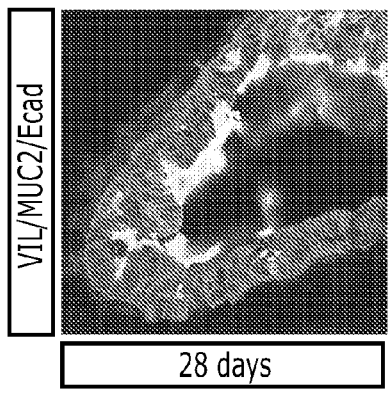
Figure 11G:
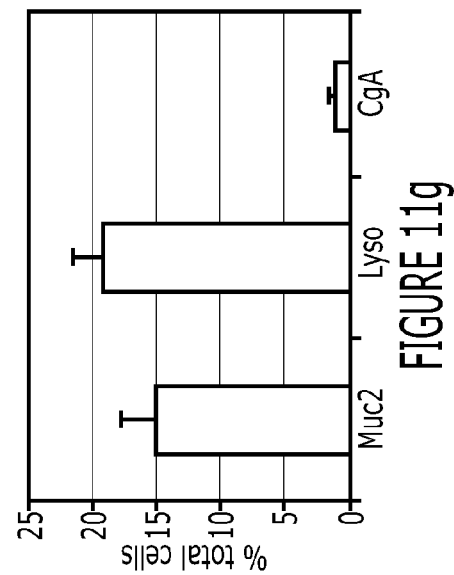
Figure 11L:
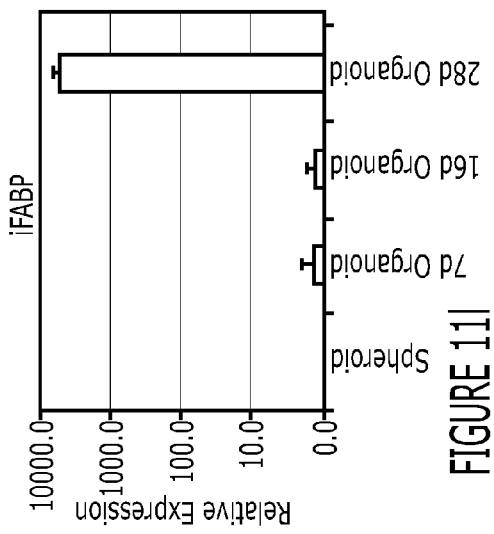
Figure 11K:
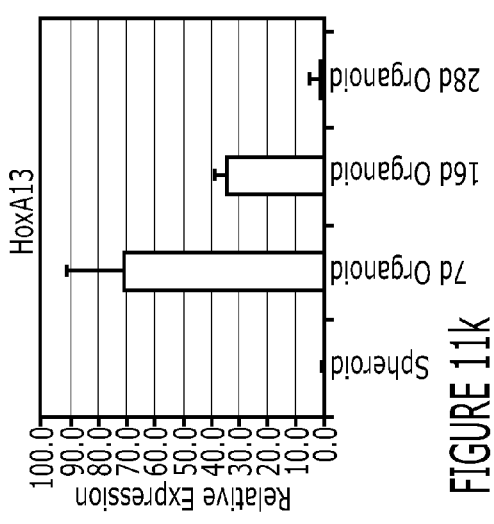
Figure 11M:
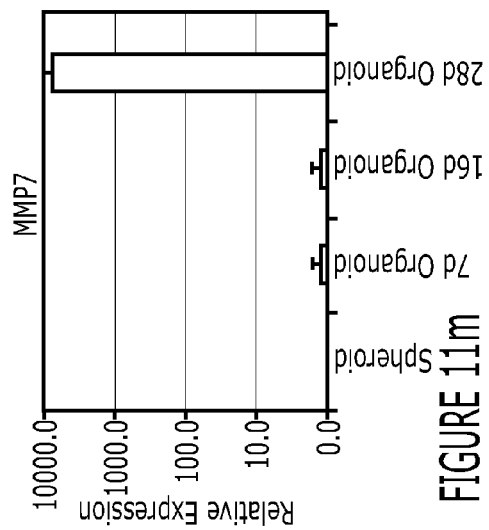
Figure 11J:
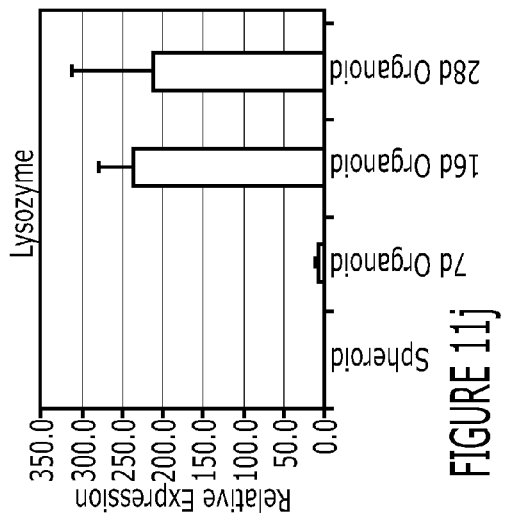

While in vivo engraftment of PSC-derived cell types, such as pancreatic endocrine cells, has been used to promote maturation, maturation in vivo is a poorly defined process and is experimentally intractable. Primitive hindgut spheroids were sjpwm matured into intestine in vitro using the recently described 3-dimensional culture conditions that support growth and renewal of the adult intestinal epithelia. When placed into this culture system, hindgut spheroids developed into intestinal organoids in a staged manner that was strikingly similar to fetal gut development (FIG. 3 and FIG. 8). In the first 14 days the simple cuboidal epithelium of the spheroid expanded and formed a highly convoluted pseudostratified epithelium surrounded by mesenchymal cells (FIG. 3a-c). After 28 days, the epithelium matured into a columnar epithelium with villus-like involutions that protrude into the lumen of the organoid (FIG. 3d, e). Comparable transitions were observed during mouse fetal intestinal development (FIG. 3f, g and FIG. 8). The spheroids expanded up to 40 fold in mass as they formed organoids (data not shown). Moreover, 28-day organoids were split and passaged up to 5 additional times and cultured for over 100 days. The cellular gain during that time was up to 1,000 fold (data not shown), resulting in a total cellular expansion of 40,000 fold per hindgut spheroid.

Figures 3H, 3I:
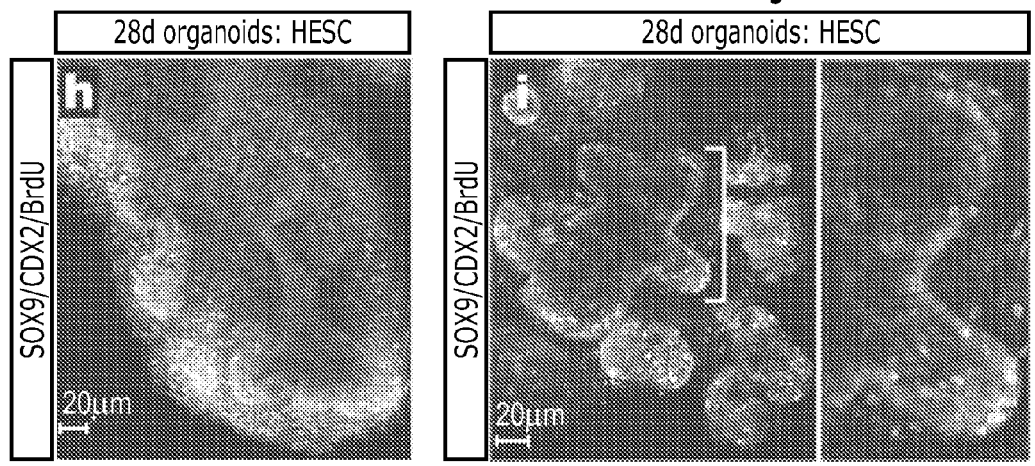
FIGS. 3h and 3i are whole mount immunofluorescent z-stack images of two different organoids for BrdU, CDX3 and SOX9 expression.
Figure 3J:
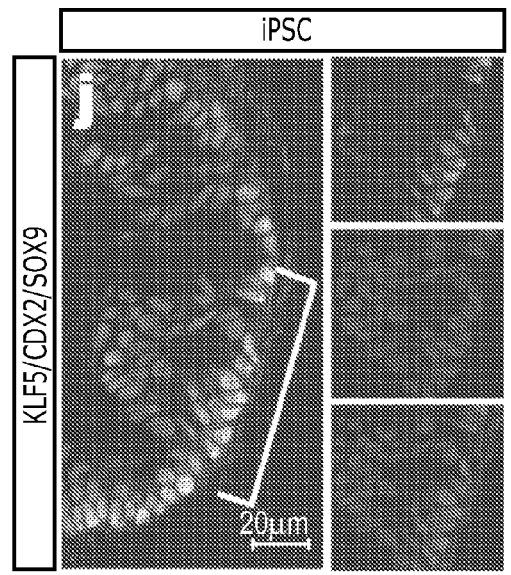
FIG. 3j is an immunofluorescent image of human induced pluripotent stem cells ("iPSCs") in which KLF5, CDX2 and localized SOX9 expression is detected.
Figure 4A:
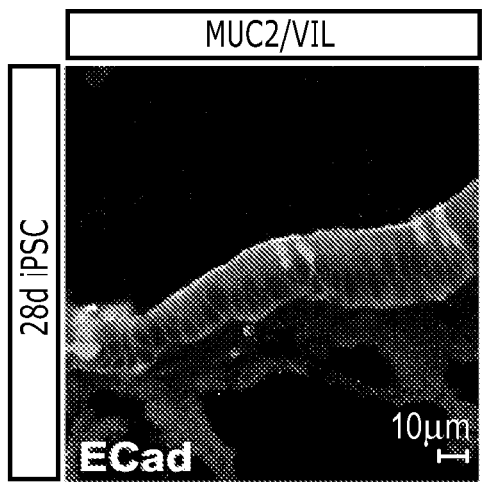
FIGS. 4a through 4c are immunofluorescent images of 28 day iPSC-derived and 38 day H9 HES-derived organoids analyzed for villin (VIL), mucin (MUC2), lysozyme (LYSO) and chromogranin A (CGA).
Figure 4A:
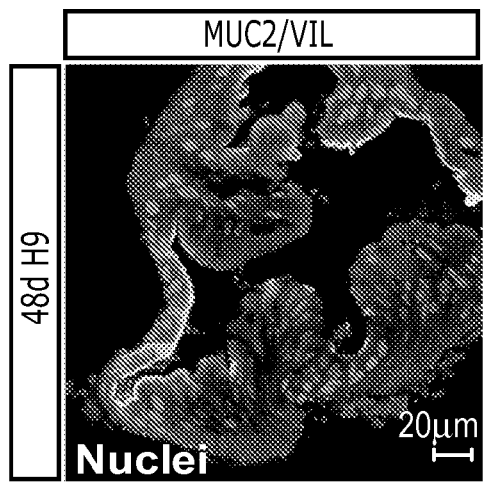
Figure 4B:
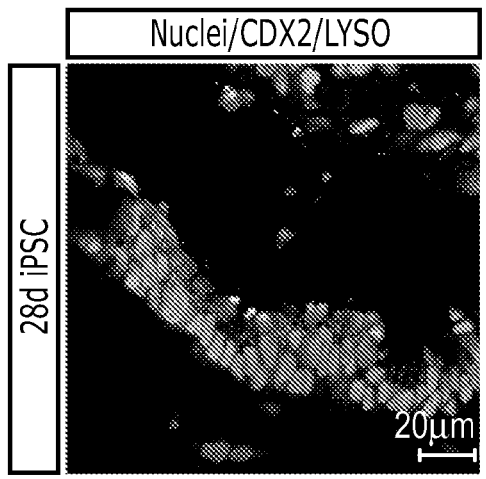
Figure 4B:
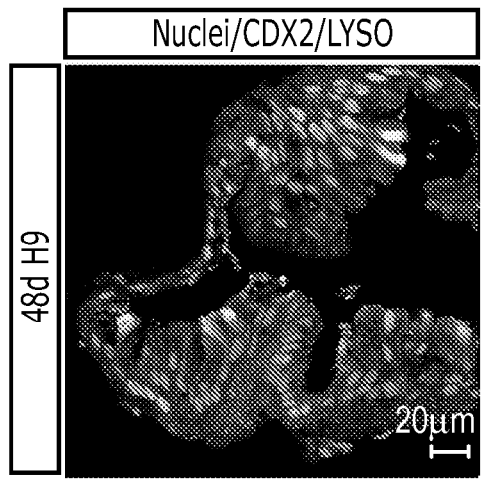
Figure 4C:
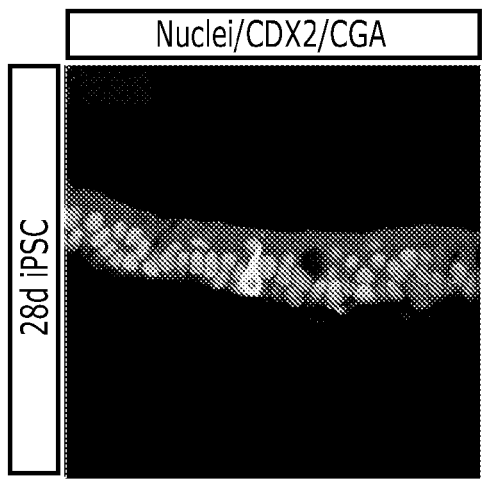
Figure 4C:
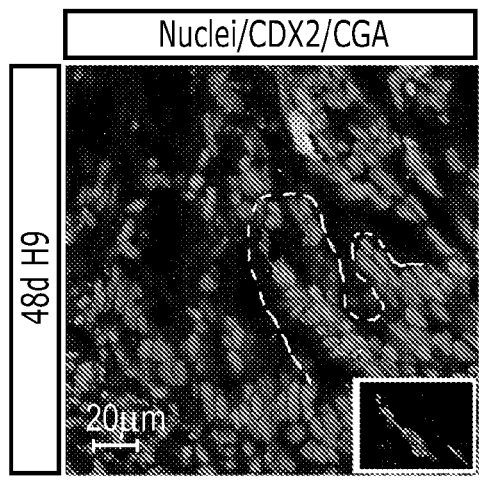
Figure 4D:
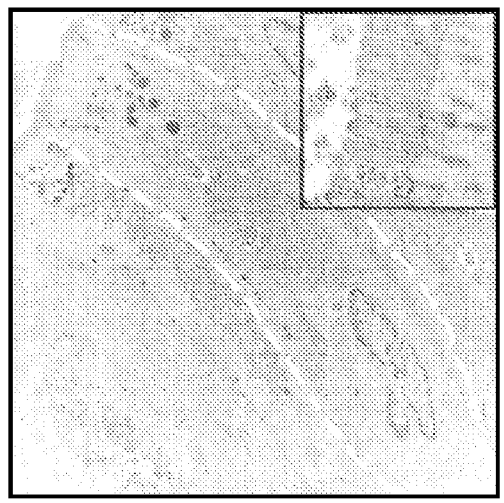
FIG. 4d is an electron micrograph image showing an enterocyte cell with a characteristic brush border with microvilli.
Figure 4E:
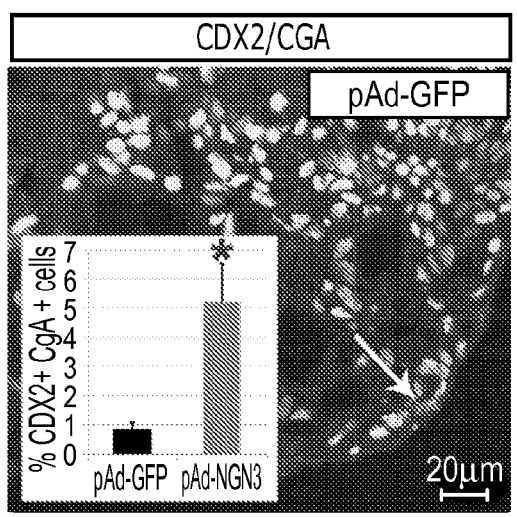
FIGS. 4e and 4f are immunofluorescent images of endocrine cell ineage development through adenoviral-mediated expression of Neurogenin 3 (NEUROG3).
Figure 4F:
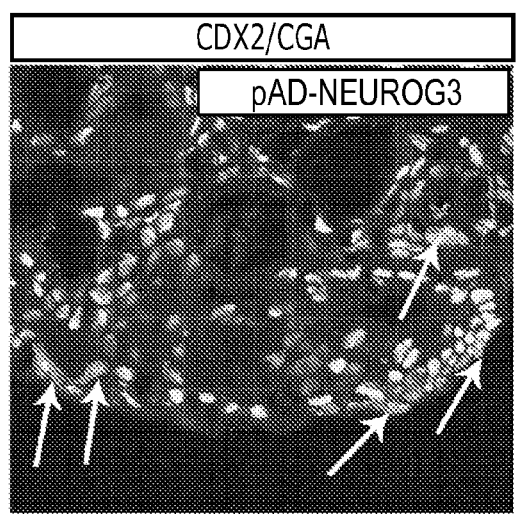

Marker analysis showed that after 14 days in culture, virtually all of the epithelium expressed the intestinal transcription factors CDX2, KLF5 and SOX9 broadly and was highly proliferative (FIG. 3b, c). By 28 days CDX2 and KLF5 remained broadly expressed, while SOX9 became localized to pockets of proliferating cells at the base of the villus-like protrusions (FIG. 3d, e, h, i). Three-dimensional rendering of a series of confocal microscopic images further revealed that the proliferative zone was in a crypt-like structure that penetrated into the underlying mesenchyme (FIG. 3 h, i). The dynamic spatial expression of CDX2, KLF5 and SOX9 in maturing, 14-28 day intestinal organoids was similar to that of the developing fetal mouse intestines between e12.5 and e16.5 (FIG. 3i, j and FIG. 8). In particular, the restriction of SOX9 to the inter-villus proliferative zone is characteristic of the developing progenitor domain, which ultimately gives rise to the intestinal stem cell niche in the crypt of Lieberkühn.

Importantly, this method for directed differentiation into intestine should be broadly applicable to other PSC lines as intestinal tissues were generated from 2 hESC and 6 iPSC lines. The kinetics of differentiation and the formation of a patterned intestinal epithelium were indistinguishable between iPSCs and hESCs (FIG. 3j, FIGS. 6, 9, 10 and Table 1B). Additional data for information on generating and analyzing iPSC lines and for DNA microarray data comparing differentiation between H9 and iPSC lines can be found in Table 2.

Maintenance and directed differentiation of human ESCs and iPSCs into intestinal tissue. Human embryonic stem cells and induced pluripotent stem cells were maintained on Matrigel (BD Biosciences) in mTesR1 media without feeders. Differentiation into Definitive Endoderm was carried out as previously described. Briefly, a 3 day ActivinA (R&D systems) differentiation protocol was used. Cells were treated with ActivinA (100 ng/ml) for three consecutive days in RPMI 1640 media (Invitrogen) with increasing concentrations of 0%, 0.2%, 2% HyClone defined FBS (dFBS) (Thermo Scientific). For hindgut differentiation, DE cells were incubated in 2% dFBS-DMEM/F12 with 500 ng/ml FGF4 and 500 ng/ml Wnt3a (R&D Systems) for 2-4 days. After 2 days with treatment of growth factors, 3-dimensional floating spheroids were present and then transferred into three-dimensional cultures previously shown to promote intestinal growth and differentiation. Briefly, spheroids were embedded in Matrigel (BD Bioscience) containing 500 ng/mL R-Spondin1 (R&D Systems), 100 ng/ml Noggin (R&D Systems) and 50 ng/ml EGF (R&D Systems). After the Matrigel solidified, media (Advanced DMEM/F12 (Invitrogen) supplemented with L-Glutamine, 10 μm Hepes, N2 supplement (R&D Systems), B27 supplement (Invitrogen), and Pen/Strep containing growth factors was overlaid and replaced every 4 days.

More details can be found in, for example, Gracz, A. D., Ramalingam, S. & Magness, S. T. Sox9-Expression Marks a Subset of CD24-expressing Small Intestine Epithelial Stem Cells that Form Organoids in vitro. *Am J Physiol Gastrointest Liver Physiol* 298, G590-600 (2010); Sato, T., et al. Single Lgr5 stem cells build crypt-villus structures in vitro without a mesenchymal niche. *Nature* 459, 262-265 (2009); Kroon, E., et al. Pancreatic endoderm derived from human embryonic stem cells generates glucose-responsive insulin-secreting cells in vivo. *Nat Biotechnol* (2008); Ludwig, T. E., et al. Feeder-independent culture of human embryonic stem cells. *Nat Methods* 3, 637-646 (2006); Ludwig, T. E., et al. Derivation of human embryonic stem cells in defined conditions. *Nat Biotechnol* 24, 185-187

(2006); D'Amour, K. A., et al. Efficient differentiation of human embryonic stem cells to definitive endoderm. *Nat Biotechnol* 23, 1534-1541 (2005); each of which is incorporated herein in its entirety.

FIGS. 3a through 3j illustrate exemplary embodiments in accordance with the present invention, showing the formation of intestine-like organoids from hESCs and hiPSCs. a, Time course of organoid growth for 13 days. (a) Organoids underwent epithelial growth and budding, forming highly convoluted epithelial structures by day 9. (b-e) Analysis of characteristic intestinal transcription factor expression (KLF5, CDX2, SOX9) and cell proliferation on serial sections of organoids after 14 and 28 days of culture (serial sections are b and c, d and e). (f) and (g) Expression of KLF5, CDX2, and SOX9 in mouse fetal intestine at e14.5 (f) and e16.5 (g) is similar to developing intestinal organoids. (h) and (i), whole mount immunofluorescence z-stacks of two different organoids for BrDU, CDX2, and SOX9 showing proliferative zones in crypt-like structures associated with the mesenchyme. (j) human iPSCs derived from keratinocytes form intestinal organoids in an identical manner to hESCs as measured by KLF5, CDX2, and localized SOX9 expression. The insets to the right in (d), (e), (g) and (j) show separated color channels.

Figure 6B:
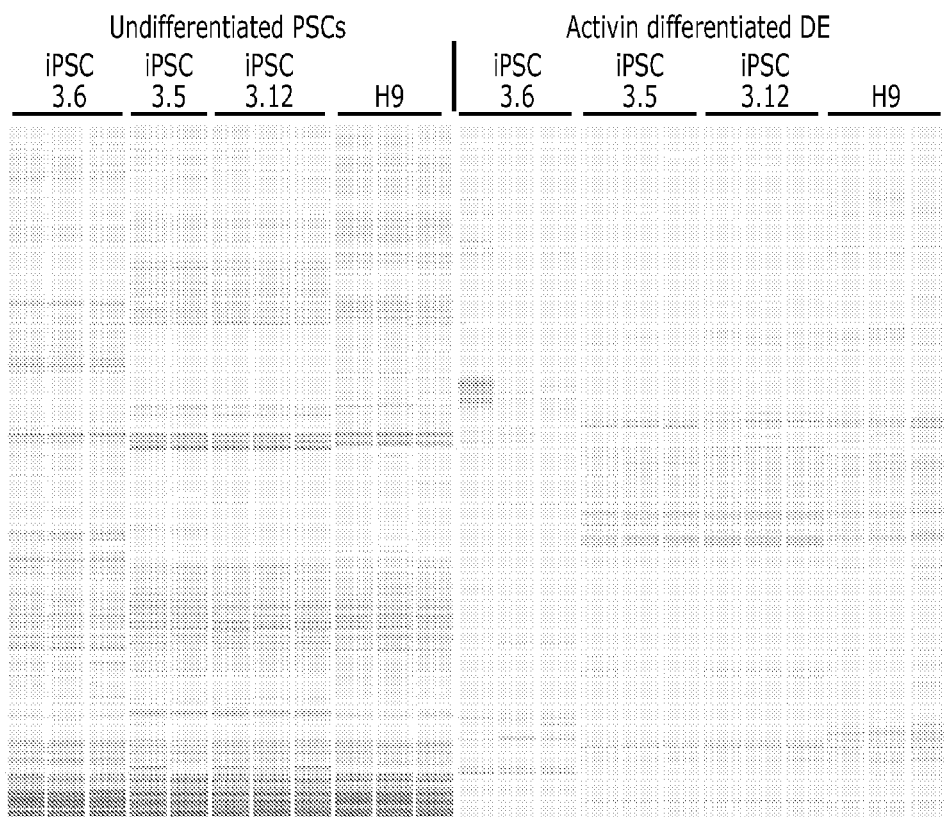
FIG. 6b is a microarray analysis of the transcriptional profile of DE induction in hESC-H9 and iPSC lines before and after DE formation.

FIGS. 6a and 6b illustrate exemplary embodiments in accordance with the present invention, depicting characterization of DE formation from hESC and iPSC lines by immuno-fluorescence (IF) and Microarray analysis. (a) Undifferentiated hESCs stained with the pluripotency marker OCT4 (green) were treated for 3 days with ActivinA. This DE induction protocol routinely results in 80-90% SOX17 (green)/FOXA2 (red) double positive cells in both hESCs and iPSCs. (b) Transcriptional profile of DE induction. hESC-H9 and iPSC lines 3.5, 3.6 and 3.12 were analyzed before and after DE formation (activin differentiation) by Affymetrix DNA microarray analysis. Clustering analysis of transcripts that were differentially regulated during DE formation indicated that iPSC lines 3.5 and 3.12 differentiate in manner that is highly similar to hESC-H9 cells (see Tables 1A and 1B for gene list and fold expression changes). iPSC line 3.6 had a more divergent transcriptional profile and was therefore not used for subsequent experiments.

FIG. 8 illustrates exemplary embodiments in accordance with the present invention, depicting molecular marker expression during mouse intestinal development. Embryonic stages include e12.5, e14.5, e16.5 and e18.5. Transcription factors detected were CDX2, KLF5, and SOX9. Epithelial markers used were E-cadherin (Ecad), Villin and DPP4. Vimentin (Vim) and Smooth Muscle Actin (SMA) were used as mesenchymal markers. Differentiation markers used were Lysozyme (Lyso) for paneth cells, Mucin (Muc2) and UEA-1 for goblet cells, Chromogranin A (CgA) for enteroendocrine cells. Phosphohistone H3 (PHH3) shows mitotic cells.

FIGS. 9a and 9b illustrate exemplary embodiments in accordance with the present invention, showing the characterization of induced pluripotent stem cell lines. All cell lines were compared to either hESC-H9 or hESC-H1 for morphology, pluripotency marker expression and karyotype. (a) Example of hESC and iPSC morphology and expression of pluripotency markers NANOG, DNMT3b, TRA 1-60 and TRA 1-81. (b) Examples of karyotypic analysis of iPSC lines 3.5, 3.6 and 16.5.

FIGS. 10a through 10g4 illustrate exemplary embodiments in accordance with the present invention, showing the morphologic comparison of hESC and iPSC organoid formation. (a)-(f) Hindgut spheroid formation from H9 human ESCs (a)-(c) or iPSCs (d)-(f) that were differentiated into endoderm and cultured without growth factors, see (a) and (d); or with 500 ng/mL FGF4+Wnt3a, see (b), (c), (e), and (f), for 96 hours. Control cultures contained little evidence of three dimensional structures (a,d) whereas FGF4+Wnt3a treated cultures contained tube like structures (yellow arrowheads; (c), (e), (f)) and free floating spheroids (black arrowheads; (b), (c), (e), (f)). (g) Examples of four different iPSC spheroids that were expanded in matrigel for 18 days (g1)-(g4). As with hESC-derived organoids, iPSC organoids contain an internal epithelium surrounded by mesenchyme.

Example 3

Cytodifferentiation of PSCs into Mature Intestinal Cell Types

Between 18 and 28 days in vitro, it was observed that cytodifferentiation of the stratified epithelium into a columnar epithelium containing brush borders and all of the major cell lineages of the gut as determined by immunofluorescence and RT-qPCR (FIG. 4 and FIG. 11). By 28 days of culture Villin (FIG. 4a, a') and DPPIV were localized to the apical surface of the polarized columnar epithelium and transmission electron microscopy revealed a brush border of apical microvilli indistinguishable from those found in mature intestine (FIG. 4d and FIG. 5). Cell counting revealed that the epithelium contained approximately 15% MUC2+ goblet cells (FIG. 4a, a'), which secrete mucin into the lumen of the organoid (FIG. 11e), 18% lysozyme positive cells that are indicative of Paneth cells (FIG. 4b, b') and about 1% chromogranin A-expressing enteroendocrine cells (FIG. 4 c, c'; and FIG. 11). RT-qPCR confirmed presence of additional markers of differentiated enterocytes (iFABP) and Paneth cells (MMPI). The analysis of GATA4 and GATA6 and HOX factors suggested that individual organoids are a mix of proximal (GATA4+/GATA6+) and distal (GATA4–/GATA6+)(HOXA13-expressing) intestine (FIG. 12).

The molecular basis of congenital malformations in humans is often inferred from studies in model organisms. For example, *Neurogenin* 3 (NEUROG3) was investigated as a candidate gene responsible for congenital loss of intestinal enteroendocrine cells in humans because of its known role in enteroendocrine cell development in mouse. Since it has not yet been possible to directly determine if NEUROG3 regulates cytodifferentiation during human intestinal development, a NEUROG3-GFP fusion protein or a GFP-only control was expressed in 28 day human organoids using Adenoviral-mediated transduction. After six days, Ad-NEUROG3 infected organoids contained 5-fold more chromograninA+ endocrine cells than control organoids (Ad-EGFP) (FIG. 4e, f), demonstrating that NEUROG3 expression was sufficient to promote an enteroendocrine cell fate. The fact that cells that maintained NEUROG3-GFP expression did not differentiate into chromograninA+ endocrine cells is consistent with need to down regulate NEUROG3 prior to terminal differentiation.

More details can be found in, for example, Haveri, H., et al. Transcription factors GATA-4 and GATA-6 in normal and neoplastic human gastrointestinal mucosa. *BMC Gastroenterology* 8, 9 (2008); Wang, J., et al. Mutant neurogenin-3 in congenital malabsorptive diarrhea.[see comment]. *New England Journal of Medicine* 355, 270-280 (2006); Jenny, M., et al. Neurogenin3 is differentially required for endocrine cell fate specification in the intestinal and gastric epithelium. *Embo J* 21, 6338-6347 (2002); Lee et al., Neurogenin 3 is essential for the proper specification of gastric enteroendocrine cells and the maintenance of gastric epithelial cell identity. *Genes Dev* 16, 1488-1497 (2002); Lopez-Diaz, L., et al. Intestinal Neurogenin 3 directs differentiation of a bipotential secretory progenitor to endocrine cell rather than goblet cell fate. *Dev Biol* 309, 298-305 (2007); Ootani, A., et al. Sustained in vitro intestinal epithelial culture within a Wnt-dependent stem cell niche. *Nat Med* 15, 701-706 (2009); Zhou, Q., Brown, J., Kanarek, A., Rajagopal, J. & Melton, D. A. In vivo reprogramming of adult pancreatic exocrine cells to beta-cells. *Nature* 455, 627-632 (2008); each of which is incorporated herein in its entirety.

FIGS. 4a through 4f illustrate exemplary embodiments in accordance with the present invention, showing the formation of all major intestinal cell types and directed differentiation of the endocrine lineage with Neurogenin 3 (NEUROG3). 28 day iPSC-derived or 48 day H9 HES-derived organoids were analyzed for villin (VIL) (a) and (a'), the goblet cell marker mucin (MUC2); (b) and (b'), the paneth cell marker lysozyme (LYSO); or (c) and (c'), the endocrine cell marker chromogranin A (CGA). (d) Electron micrograph showing an enterocyte cell with a characteristic brush border with microvilli (inset). (e) and (f) Promoting endocrine cell lineage development using adenoviral-mediated expression of Neurogenin 3 (NEUROG3). pAd-NEUROG3 causes a 5-fold increase in the percent of CGA+ cells compared to a control adenovirus (pAd-GFP). Error bars denote standard error mean. Significance is shown by;* ($p=0.005$)

Figure 5C:
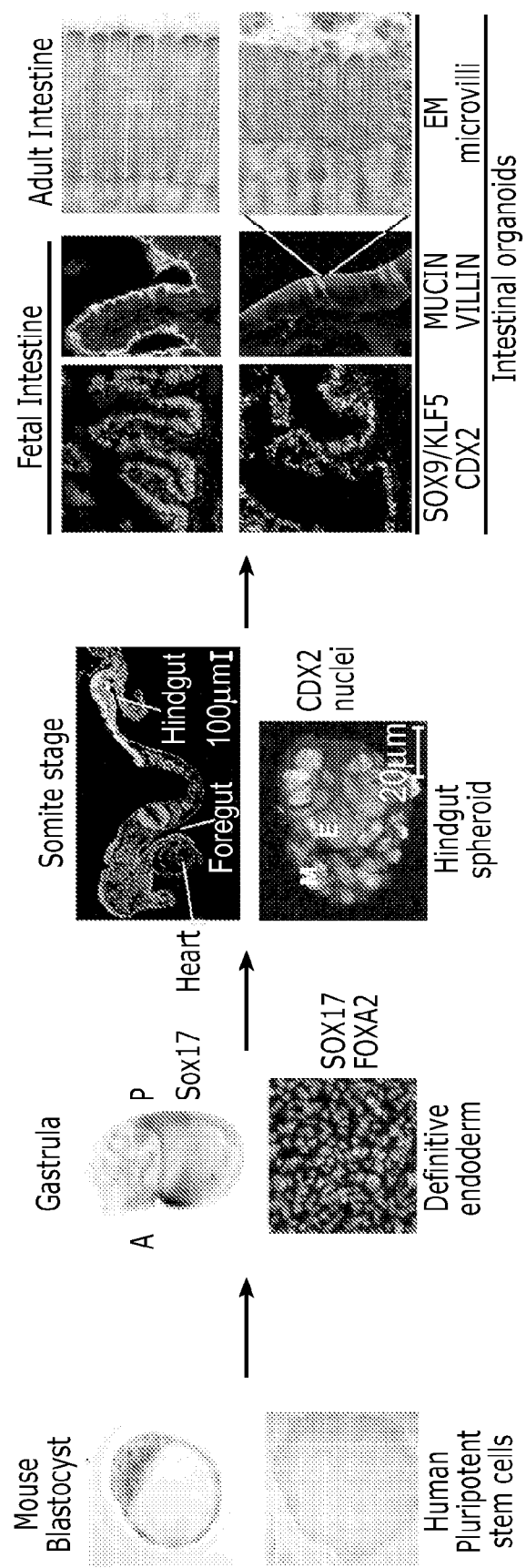
FIG. 5c includes microscopic and immunofluorescent images of mouse embryonic intestinal development (top) and human intestinal organoid development (bottom) in a side-by-side comparison.

FIGS. 5a-5c illustrate exemplary embodiments, showing a model comparing embryonic intestinal development versus directed differentiation of human PSCs into intestinal tissue in vitro. (a) Schematic of human intestinal development. At the blastocyst stage, the inner cell mass (ICM) gives rise to the entire embryo. The ICM is also the source of embryonic stem cells. At the gastrula stage, the embryo contains the three germ layers including the embryonic/definitive endoderm (yellow). The definitive endoderm forms a primitive gut tube, with the hindgut forming in the posterior region of the embryo. The hindgut undergoes intestinal morphogenesis forming the small and large intestines. (b) Schematic of directed differentiation of PSCs into intestinal tissue. PSCs cultured for 3 days in ActivinA form definitive endoderm (DE) co-expressing SOX17 and FOXA2. DE cultured for 4 days in FGF4 and Wnt3a (500 ng/ml each) form three-dimensional hindgut spheroids expressing the posterior marker CDX2. Spheroids formed intestinal organoids when grown in three dimensional conditions that favor expansion and differentiation of intestinal precursors (matrigel with 500 ng/ml R-Spondin1, 100 ng/ml Noggin and 50 ng/ml EGF. (c) Side-by-side comparison of mouse embryonic intestinal development (top) and human intestinal organoid development (bottom). PSCs underwent staged differentiation in a manner that was highly reminiscent of embryonic intestinal development and formed intestinal tissue. Stages of development in c are the same as schematically shown in (a) and (b).

FIGS. 11a through 11m illustrate exemplary embodiments in accordance with the present invention, showing the molecular analysis of stages of epithelial growth, maturation and cytodifferentiation. (a) 96 hours after FGF4+Wnt3a exposure, hindgut spheroids contained a highly proliferative cuboidal epithelium that expressed CDX2. (b)-(d) 18 day iPSC-derived organoids contained a pseudostratified epithelium that broadly expressed CDX2, KLF5 and SOX9 (b), had weak apical villin staining (c), and had begun expressing markers of cytodifferentiation including lysozyme (Lyso) (d). (e) and (f) At 28 days, organoids secreted mucin into the lumen (e-green), broadly expressed CDX2 and KLF5 and showed restricted expression of SOX9 (f). (g) The number of cells that expressed cytodifferentiation markers ChromograninA (ChA), lysozyme (Lyso) or Mucin (Muc2) was quantified and represented as a percent of total CDX2+ epithelial cells in 28d hESC organoids. (h)-(m) Quantitative analysis of intestinal markers SOX9, Villin (enterocytes), Lysozyme (Paneth cells), HOXA13, IFABP (enterocytes) and MMPI (Paneth cells) during intestinal organoid development by RT-qPCR. Error bars denote standard deviation of triplicates.

FIGS. 12a and 12b illustrate exemplary embodiments in accordance with the present invention, showing GATA factor expression. (a) H9 hESC derived organoids show that most Cdx2 (blue) positive nuclei express Gata6 (red), whereas only a few nuclei express Gata4 (green, white arrowheads). Gata4/6 double positive cells (white arrowheads) are indicative of proximal intestine, where as Gata6+/Gata4− cells are indicative of distal intestine. (b) human iPSC derived organoids show that almost all Cdx2 positive cells (blue) are Gata6 positive (red). In this example, the organoid did not express Gata4 (green) in this section of tissue, indicating that this intestinal tissue is distal intestine.

Example 4

Mesenchymal Differentiation into Smooth Muscle

Figure 13C:
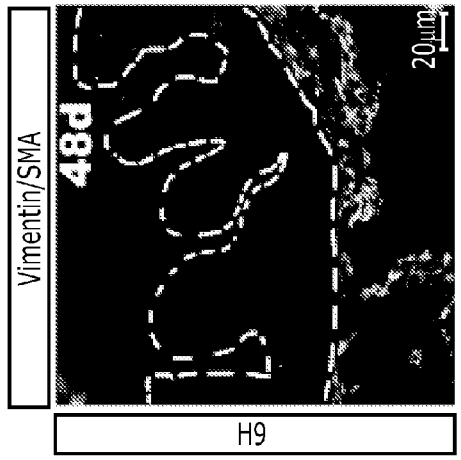
FIGS. 13a through 13f are immunofluorescent images showing mesenchymal development, in particular expression of the pan-mesenchymal markers Collagen IV (ColIV, red) and Vimentin (Vim, green) and the mesenchymal differentiation marker smooth muscle actin (SMA) during organoid development.

During intestinal development, epithelial and mesenchymal differentiation is regulated via a series of reciprocal signaling events. In PSC-derived cultures, the gut mesenchyme, which likely arises from the few mesoderm cells found in DE cultures, underwent stereotypic differentiation similar to developing mesenchyme in vivo. In the early stages of culture the mesenchyme underwent extensive proliferation (FIG. 3) and formed a homogeneous vimentin+/collagenIV+ layer around the epithelium (FIG. 13) similar to an e12.5 embryonic intestine (FIG. 8). By 18 days there was evidence of regional expression collagen IV, vimentin, or smooth muscle actin (SMA) in different mesenchymal layers (FIGS. 13d and 13f. By 28 days SMA+ cells had further expanded around the epithelium and by 48 days became one of several thin layers of cells adjacent to the epithelium (FIG. 13c). The fact that intestinal mesenchyme differentiation coincided with overlying epithelium suggests that epithelial-mesenchymal crosstalk may be important in the development of PSC-derived intestinal organoids.

In conclusion, this is the first report demonstrating that human PSCs can be efficiently directed to differentiate in vitro into intestinal tissue that includes multiple secretory and absorptive cell types. These findings establish an accessible and genetically tractable system to investigate the molecular basis of human congenital gut defects in vitro and to generate intestinal tissue for transplantation. Moreover human intestinal cultures are a potentially powerful tool for mechanistic studies of drug transport and absorption.

More details can be found in, for example, Zorn, A. M. & Wells, J. M. Vertebrate Endoderm Development and Organ Formation. *Annu Rev Cell Dev Biol* 25, 1-31 (2009); McLin, V. A., Henning, S. J. & Jamrich, M. The role of the visceral mesoderm in the development of the gastrointestinal tract. *Gastroenterology* 136, 2074-2091 (2009); Spence, J. R. & Wells, J. M. Translational embryology: Using embryonic principles to generate pancreatic endocrine cells from embryonic stem cells. *Developmental Dynamics* 236, 3218-3227. (2007); each of which is incorporated herein in its entirety.

Figure 13F:
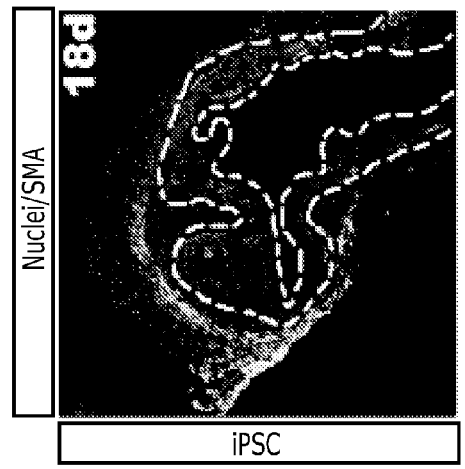
Figure 13B:
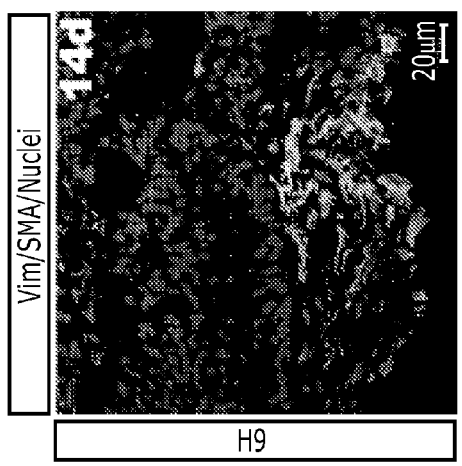
Figure 13E:
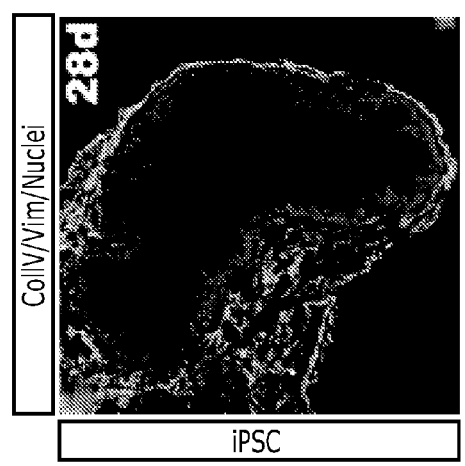
Figure 13A:
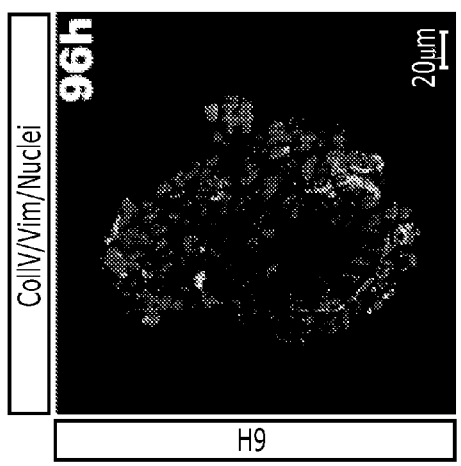
Figure 13D:
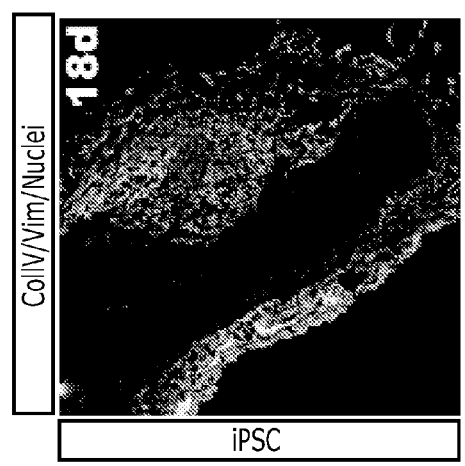

FIGS. 13a and 13f illustrate exemplary embodiments in accordance with the present invention, showing mesenchymal development. (a)-(f) Expression of the pan-mesenchymal markers Collagen IV (ColIV, red) and Vimentin (Vim, green) and the mesenchymal differentiation marker smooth muscle actin (SMA) during organoid development. a, 96 hour H9 spheroid showed Collagen IV staining (red) in the basal layer under the epithelium and weak expression of vimentin (green). b and d, By 14 to 18 days Vimentin and Collagen IV was broadly expressed in the mesenchyme surrounding the organoid epithelium. (b), (c), (f) Smooth muscle actin (SMA) was broadly expressed in 14 day organoids (b) but was restricted to a ring of cells in the 18 day organoid (f). SMA progressively became restricted to a thin layer of mesenchyme surrounding the epithelium at 48 days (c). Nuclei are stained with Draq5 and pseudo-colored blue where indicated.

Example 5

Generation and Characterization of Human iPSC Lines

For preparation of primary keratinocytes from human foreskins, tissues were cultured in dispase to remove the dermis from the epidermis, then trypsinized and cultured in serum-free low calcium medium (Epilife medium, Cascade Biologics, Portland, Oreg.) and antibiotics. For generating iPSC lines, human keratinocytes were transduced with recombinant retroviruses expressing Oct4, Sox2, Klf4 and c-Myc and plated onto mouse embryonic fibroblast (MEF) feeders in the presence of the HDAC inhibitor valproic acid. After 2-4 weeks, iPSC colonies were picked and expanded into cell lines. The iPSC lines were expanded and passaged and analyzed for hESC-like morphology, expression of pluripotency markers (SSEA3 and Tra1-81), and karyotype. iPSC lines were maintained on MEFs or in feeder-free, defined conditions.

Example 6

Generation and Characterization of Induced Pluripotent Stem Cell Lines

Normal human skin keratinocytes (NHSK) were obtained from donors with informed consent (CCHMC IRB protocol CR1_2008-1331). NHSKs were isolated from punch biopsies following trypsinization and subsequent culture on irradiated NIH3T3 feeder cells in F media. For iPSC generation, NHSKs were transduced on two consecutive days with a 1:1:1:1 mix of recombinant RD114-pseudotyped retroviruses expressing Oct4, Sox2, Klf4 and cMyc in the presence of 8 µg/mL polybrene. Twenty-four hours after the second transduction the virus mix was replaced with fresh F media and cells were incubated for an additional three days. Cells were then trypsinized and seeded into 6 well dishes containing $1.875 \times 10^5$ irradiated mouse fibroblasts per well and Epilife medium. On the following day, media was replaced with DMEM/F12 50:50 media supplemented with 20% knockout serum replacement, 1 mM L-glutamine, 0.1 mM β-mercaptoethanol, 1× non-essential amino acids, 4 ng/mL basic fibroblast growth factor, and 0.5 mM valproic acid. Morphologically identifiable iPSC colonies arose after 2-3 weeks and were picked manually, expanded and analyzed for expression of human pluripotent stem cell markers Nanog, DNMT3b, Tra1-60 and Tra1-81. Early passage iPSC lines were adapted to feeder-free culture conditions consisting of maintenance in mTeSR1 (Stem Cell Technologies) in culture dishes coated with matrigel (BD Biosciences) and lines were karyotyped.

More details can be found in, for example, Lambert, P. F., et al. Using an immortalized cell line to study the HPV life cycle in organotypic "raft" cultures. *Methods in molecular medicine* 119, 141-155 (2005); Takahashi et al. Induction of pluripotent stem cells from adult human fibroblasts by defined factors. Cell 131, 861-872 (2007); Takahashi, K. & Yamanaka, S. Induction of pluripotent stem cells from mouse embryonic and adult fibroblast cultures by defined factors. *Cell* 126, 663-676 (2006); D'Amour et al., Production of pancreatic hormone-expressing endocrine cells from human embryonic stem cells. *Nat Biotechnol* 24, 1392-1401 (2006); Richards et al., The transcriptome profile of human embryonic stem cells as defined by SAGE. *Stem Cells* 22, 51-64 (2004); Thomson, J. A., et al. Embryonic stem cell lines derived from human blastocysts. *Science* 282, 1145-1147 (1998); each of which is incorporated herein in its entirety.

Example 7

Microarray Analysis of Human ESCs, iPSCs and DE Cultures

For microarray analysis, RNA was isolated from undifferentiated and 3-day activin treated hESC and iPSC cultures and used create target DNA for hybridization to Affymetrix Human 1.0 Gene ST Arrays using standard procedures (Affymetrix, Santa Clara, Calif.). Independent biological triplicates were performed for each cell line and condition. Affymetrix microarray Cel files were subjected to Robust Multichip Average (RMA) normalization in GeneSpring 10.1. Probe sets were first filtered for those that are overexpressed or underexpressed and then subjected to statistical analysis for differential expression by 3 fold or more between undifferentiated and differentiated cultures with $p<0.05$ using the Students T-test. This procedure generated a list of 530 probe sets, as shown in Table 2. Log 2 gene expression ratios were then subjected to hierachical clustering using the standard correlation distance metric as implemented in GeneSpring.

TABLE 2

Variations of Transcript levels (2-fold or more) during DE formation in hESC-H9 and iPSC lines 3.12, 3.5, and 3.6

| GENE SYMBOL | DIFF'D-H9] VS [UNDIFF'D-H9] (folds) | [DIFF'D-IPSC3.12] VS [UNDIFF'D-IPSC3.12] (folds) | [Diff'd-iPSC3.4] vs [Undiff'd-iPSC3.4] (folds) | GENE DESCRIPTION |
|---|---|---|---|---|
| CER1 | 137.61 | 67.98 | 66.76 | cerberus 1, cysteine knot superfamily, homolog (*Xenopus laevis*) |
| HAS2 | 32.29 | 15.27 | 13.43 | hyaluronan synthase 2 |
| PRDM1 | 30.35 | 24.92 | 21.56 | PR domain containing 1, with ZNF domain |

TABLE 2-continued

Variations of Transcript levels (2-fold or more) during DE formation in hESC-H9 and iPSC lines 3.12, 3.5, and 3.6

| GENE SYMBOL | DIFF'D-H9] VS [UNDIFF'D-H9] (folds) | [DIFF'D-IPSC3.12] VS [UNDIFF'D-IPSC3.12] (folds) | [Diff'd-iPSC3.4] vs [Undiff'd-iPSC3.4] (folds) | GENE DESCRIPTION |
|---|---|---|---|---|
| SEMA3E | 30.17 | 21.66 | 19.36 | sema domain, immunoglobulin domain (Ig), short basic domain, secreted, (semaphorin) 3E |
| MFAP4 | 28.35 | 29.08 | 35.47 | microfibrillar-associated protein 4 |
| EOMES | 28.31 | 19.85 | 27.72 | eomesodermin homolog (Xenopus laevis) |
| CYP26A1 | 28.12 | 41.18 | 47.21 | cytochrome P450, family 26, subfamily A, polypeptide 1 |
| SLC40A1 | 27.82 | 33.13 | 34.77 | solute carrier family 40 (iron-regulated transporter), member 1 |
| CXCR4 | 24.73 | 23.19 | 19.91 | chemokine (C—X—C motif) receptor 4 |
| FGF17 | 17.92 | 15.78 | 19.00 | fibroblast growth factor 17 |
| TRPA1 | 17.40 | 25.46 | 23.50 | transient receptor potential cation channel, subfamily A, member 1 |
| ANKRD1 | 17.20 | 11.45 | 8.97 | ankyrin repeat domain 1 (cardiac muscle) |
| LOC100132916 | 15.91 | 12.59 | 9.65 | similar to hCG1811192 |
| PCDH10 | 15.88 | 18.81 | 23.07 | protocadherin 10 |
| RHOBTB3 | 15.76 | 12.01 | 8.61 | Rho-related BTB domain containing 3 |
| LGR5 | 15.44 | 12.18 | 12.88 | leucine-rich repeat-containing G protein-coupled receptor 5 |
| CD48 | 14.69 | 18.02 | 15.22 | |
| ST8SIA4 | 14.68 | 10.83 | 9.75 | ST8 alpha-N-acetyl-neuraminide alpha-2,8-sialyltransferase 4 |
| COL5A2 | 14.57 | 13.25 | 15.28 | collagen, type V, alpha 2 |
| COLEC12 | 13.69 | 11.08 | 12.98 | collectin sub-family member 12 |
| FLRT3 | 12.96 | 15.64 | 11.19 | fibronectin leucine rich transmembrane protein 3 |
| CHL1 | 12.67 | 2.89 | 3.63 | cell adhesion molecule with homology to L1CAM (close homolog of L1) |
| ELOVL2 | 12.67 | 6.73 | 6.61 | elongation of very long chain fatty acids (FEN1/Elo2, SUR4/Elo3, yeast)-like 2 |
| CCL2 | 12.64 | 18.30 | 14.69 | chemokine (C-C motif) ligand 2 |
| MIXL1 | 12.51 | 7.17 | 8.06 | Mix1 homeobox-like 1 (Xenopus laevis) |
| MGST2 | 11.94 | 15.71 | 13.68 | microsomal glutathione S-transferase 2 |
| EHHADH | 11.32 | 9.12 | 8.12 | enoyl-Coenzyme A, hydratase/3-hydroxyacyl Coenzyme A dehydrogenase |
| PLXNA2 | 11.05 | 9.37 | 9.50 | plexin A2 |
| DIO3 | 10.97 | 9.31 | 7.22 | deiodinase, iodothyronine, type III |
| KLF8 | 10.94 | 6.17 | 5.97 | Kruppel-like factor 8 |
| PEG10 | 10.92 | 3.35 | 3.97 | paternally expressed 10 |
| TDRD7 | 10.91 | 9.40 | 9.32 | tudor domain containing 7 |
| MANEA | 10.90 | 8.67 | 8.97 | mannosidase, endo-alpha |
| UPK1B | 10.83 | 5.46 | 5.74 | uroplakin 1B |
| ROR2 | 10.22 | 8.35 | 8.35 | receptor tyrosine kinase-like orphan receptor 2 |
| CCKBR | 9.79 | 12.68 | 9.37 | cholecystokinin B receptor |
| DKK1 | 9.66 | 6.27 | 7.27 | dickkopf homolog 1 (Xenopus laevis) |
| SERPINB9 | 9.32 | 10.27 | 10.52 | serpin peptidase inhibitor, clade B (ovalbumin), member 9 |
| OR5P2 | 9.18 | 5.08 | 6.24 | olfactory receptor, family 5, subfamily P, member 2 |
| OVCH2 | 9.06 | 6.77 | 7.92 | ovochymase 2 |
| FRZB | 8.79 | 5.92 | 5.20 | frizzled-related protein |
| SAMD3 | 8.40 | 8.88 | 7.82 | sterile alpha motif domain containing 3 |
| HHEX | 8.37 | 15.27 | 10.62 | hematopoietically expressed homeobox |
| PPAPDC1A | 8.00 | 4.50 | 3.94 | phosphatidic acid phosphatase type 2 domain containing 1A |
| MYL7 | 7.96 | 6.41 | 7.32 | myosin, light chain 7, regulatory |
| PLSCR4 | 7.87 | 7.11 | 8.62 | phospholipid scramblase 4 |
| ITGA5 | 7.82 | 4.31 | 4.38 | integrin, alpha 5 (fibronectin receptor, alpha polypeptide) |
| ENC1 | 7.76 | 3.37 | 3.08 | ectodermal-neural cortex (with BTB-like domain) |
| TNC | 7.73 | 6.30 | 9.01 | tenascin C (hexabrachion) |
| C5 | 7.59 | 14.18 | 14.56 | complement component 5 |
| SOX17 | 7.34 | 7.29 | 7.58 | SRY (sex determining region Y)-box 17 |

TABLE 2-continued

Variations of Transcript levels (2-fold or more) during DE formation in hESC-H9 and iPSC lines 3.12, 3.5, and 3.6

| GENE SYMBOL | DIFF'D-H9] VS [UNDIFF'D-H9] (folds) | [DIFF'D-IPSC3.12] VS [UNDIFF'D-IPSC3.12] (folds) | [Diff'd-iPSC3.4] vs [Undiff'd-iPSC3.4] (folds) | GENE DESCRIPTION |
|---|---|---|---|---|
| RLBP1L2 | 7.31 | 6.87 | 6.65 | retinaldehyde binding protein 1-like 2 |
| VAMP8 | 7.30 | 3.74 | 4.09 | vesicle-associated membrane protein 8 (endobrevin) |
| PLCE1 | 7.11 | 7.55 | 6.70 | phospholipase C, epsilon 1 |
| NTN4 | 7.09 | 6.11 | 5.15 | netrin 4 |
| PROS1 | 7.01 | 4.02 | 4.07 | protein S (alpha) |
| LRIG3 | 6.97 | 9.55 | 9.18 | leucine-rich repeats and immunoglobulin-like domains 3 |
| CDH2 | 6.89 | 8.08 | 7.38 | cadherin 2, type 1, N-cadherin (neuronal) |
| CFLAR | 6.84 | 6.90 | 6.63 | CASP8 and FADD-like apoptosis regulator |
| ARHGAP24 | 6.74 | 5.33 | 5.92 | Rho GTPase activating protein 24 |
| C6ORF60 | 6.67 | 7.85 | 6.40 | chromosome 6 open reading frame 60 |
| MCC | 6.48 | 3.48 | 3.37 | mutated in colorectal cancers |
| GPR177 | 6.42 | 5.21 | 4.84 | G protein-coupled receptor 177 |
| CPE | 6.36 | 7.33 | 6.89 | carboxypeptidase E |
| C9ORF19 | 6.14 | 5.15 | 5.52 | chromosome 9 open reading frame 19 |
| PLSCR1 | 5.99 | 4.35 | 3.70 | phospholipid scramblase 1 |
| BMP2 | 5.95 | 7.43 | 6.96 | bone morphogenetic protein 2 |
| OR5P3 | 5.80 | 3.50 | 4.65 | olfactory receptor, family 5, subfamily P, member 3 |
| FN1 | 5.77 | 3.80 | 3.73 | fibronectin 1 |
| TBC1D9 | 5.72 | 5.94 | 5.11 | TBC1 domain family, member 9 (with GRAM domain) |
| VWF | 5.69 | 5.27 | 5.12 | von Willebrand factor |
| NODAL | 5.66 | 5.77 | 5.00 | nodal homolog (mouse) |
| GSC | 5.57 | 5.37 | 5.22 | goosecoid homeobox |
| SMAD6 | 5.53 | 2.54 | 2.97 | SMAD family member 6 |
| S100Z | 5.52 | 4.68 | 4.36 | S100 calcium binding protein Z |
| ARHGAP29 | 5.52 | 4.47 | 4.19 | Rho GTPase activating protein 29 |
| LHX1 | 5.51 | 4.72 | 4.60 | LIM homeobox 1 |
| ARSE | 5.42 | 5.47 | 5.25 | arylsulfatase E (chondrodysplasia punctata 1) |
| CNGA4 | 5.39 | 4.06 | 4.78 | cyclic nucleotide gated channel alpha 4 |
| AHNAK | 5.34 | 4.93 | 4.71 | |
| SEPP1 | 5.28 | 5.27 | 4.42 | selenoprotein P, plasma, 1 |
| PROS1 | 5.23 | 3.60 | 3.95 | protein S (alpha) |
| CALCR | 5.20 | 3.44 | 3.13 | calcitonin receptor |
| IER3 | 5.14 | 6.06 | 5.38 | immediate early response 3 |
| MAN1A1 | 5.12 | 4.60 | 4.23 | mannosidase, alpha, class 1A, member 1 |
| KCNG1 | 5.09 | 3.70 | 4.11 | potassium voltage-gated channel, subfamily G, member 1 |
| BNIP3 | 5.08 | 3.56 | 3.35 | BCL2/adenovirus E1B 19 kDa interacting protein 3 |
| H2AFY2 | 5.05 | 7.17 | 6.81 | H2A histone family, member Y2 |
| FAM122C | 5.03 | 4.61 | 4.20 | family with sequence similarity 122C |
| FMN2 | 5.03 | 3.77 | 4.77 | formin 2 |
| PPFIBP2 | 5.03 | 4.02 | 4.10 | PTPRF interacting protein, binding protein 2 (liprin beta 2) |
| ARRDC3 | 4.99 | 4.14 | 3.33 | arrestin domain containing 3 |
| GATM | 4.99 | 4.95 | 3.94 | glycine amidinotransferase (L-arginine:glycine amidinotransferase) |
| C21ORF129 | 4.97 | 10.33 | 8.83 | chromosome 21 open reading frame 129 |
| KRT8 | 4.96 | 2.41 | 2.50 | keratin 8 |
| ADAM19 | 4.96 | 4.37 | 4.36 | ADAM metallopeptidase domain 19 (meltrin beta) |
| BTG2 | 4.90 | 3.29 | 3.20 | BTG family, member 2 |
| ARRB1 | 4.90 | 2.66 | 3.03 | arrestin, beta 1 |
| AGL | 4.90 | 3.65 | 3.09 | amylo-1,6-glucosidase, 4-alpha-glucanotransferase (glycogen debranching enzyme, glycogen storage disease type III) |
| IFLTD1 | 4.86 | 2.44 | 2.79 | intermediate filament tail domain containing 1 |
| TIPARP | 4.84 | 4.13 | 3.77 | TCDD-inducible poly(ADP-ribose) polymerase |
| NFKBIA | 4.83 | 4.56 | 4.41 | nuclear factor of kappa light polypeptide gene enhancer in B-cells inhibitor, alpha |

TABLE 2-continued

Variations of Transcript levels (2-fold or more) during DE formation in hESC-H9 and iPSC lines 3.12, 3.5, and 3.6

| GENE SYMBOL | DIFF'D-H9] VS [UNDIFF'D-H9] (folds) | [DIFF'D-IPSC3.12] VS [UNDIFF'D-IPSC3.12] (folds) | [Diff'd-iPSC3.4] vs [Undiff'd-iPSC3.4] (folds) | GENE DESCRIPTION |
|---|---|---|---|---|
| RNF19A | 4.79 | 5.77 | 4.63 | ring finger protein 19A |
| PDZK1 | 4.77 | 3.94 | 3.57 | PDZ domain containing 1 |
| RNF152 | 4.77 | 4.66 | 4.52 | ring finger protein 152 |
| RPRM | 4.76 | 4.83 | 4.58 | reprimo, TP53 dependent G2 arrest mediator candidate |
| TGFB1 | 4.74 | 2.98 | 3.54 | transforming growth factor, beta 1 |
| CAMK2D | 4.64 | 4.00 | 3.77 | calcium/calmodulin-dependent protein kinase (CaM kinase) II delta |
| ARL4D | 4.62 | 4.07 | 3.95 | ADP-ribosylation factor-like 4D |
| ARHGAP28 | 4.60 | 3.54 | 3.27 | Rho GTPase activating protein 28 |
| C8ORF49 | 4.59 | 4.09 | 3.45 | chromosome 8 open reading frame 49 |
| MATN3 | 4.57 | 4.36 | 5.19 | matrilin 3 |
| DUSP10 | 4.54 | 4.45 | 4.76 | dual specificity phosphatase 10 |
| PTPRM | 4.51 | 5.04 | 5.21 | protein tyrosine phosphatase, receptor type, M |
| RNF125 | 4.49 | 3.53 | 3.28 | ring finger protein 125 |
| ACOX3 | 4.48 | 5.42 | 5.45 | acyl-Coenzyme A oxidase 3, pristanoyl |
| SLC22A3 | 4.40 | 4.27 | 5.11 | solute carrier family 22 (extraneuronal monoamine transporter), member 3 |
| IER3 | 4.39 | 4.79 | 4.34 | immediate early response 3 |
| NR0B1 | 4.39 | 11.17 | 9.41 | nuclear receptor subfamily 0, group B, member 1 |
| S1PR3|C9ORF47 | 4.39 | 3.21 | 4.05 | sphingosine-1-phosphate receptor 3| chromosome 9 open reading frame 47 |
| IER3 | 4.39 | 4.80 | 4.34 | immediate early response 3 |
| C8ORF79 | 4.32 | 3.02 | 2.86 | chromosome 8 open reading frame 79 |
| EPSTI1 | 4.32 | 4.91 | 4.62 | epithelial stromal interaction 1 (breast) |
| KRT19 | 4.27 | 2.48 | 2.56 | keratin 19 |
| USP53 | 4.26 | 3.53 | 3.00 | ubiquitin specific peptidase 53 |
| GPSM2 | 4.21 | 5.06 | 4.09 | G-protein signaling modulator 2 (AGS3-like, *C. elegans*) |
| PRSS35 | 4.19 | 5.55 | 5.36 | protease, serine, 35 |
| RELN | 4.13 | 3.02 | 3.30 | reelin |
| RBM24 | 4.12 | 4.75 | 3.60 | RNA binding motif protein 24 |
| RASGEF1B | 4.05 | 3.15 | 3.59 | RasGEF domain family, member 1B |
| MERTK | 4.01 | 3.13 | 3.67 | c-mer proto-oncogene tyrosine kinase |
| OTX2 | 4.01 | 5.22 | 5.32 | orthodenticle homeobox 2 |
| MAML3 | 4.00 | 3.41 | 3.52 | mastermind-like 3 (*Drosophila*) |
| PDE10A | 3.98 | 4.60 | 4.58 | phosphodiesterase 10A |
| PLCXD3 | 3.98 | 3.34 | 2.49 | phosphatidylinositol-specific phospholipase C, X domain containing 3 |
| GREM2 | 3.97 | 3.14 | 3.50 | gremlin 2, cysteine knot superfamily, homolog (*Xenopus laevis*) |
| MYO3A | 3.93 | 4.17 | 4.62 | myosin IIIA |
| NEK7 | 3.92 | 3.53 | 3.02 | NIMA (never in mitosis gene a)-related kinase 7 |
| LEPREL1 | 3.92 | 6.42 | 6.24 | leprecan-like 1 |
| MOBP | 3.92 | 2.68 | 2.52 | myelin-associated oligodendrocyte basic protein |
| KCNH8 | 3.87 | 4.09 | 3.76 | potassium voltage-gated channel, subfamily H (eag-related), member 8 |
| FAM20A | 3.84 | 4.69 | 5.21 | family with sequence similarity 20, member A |
| MID2 | 3.83 | 2.46 | 2.43 | midline 2 |
| SETD7 | 3.82 | 3.65 | 3.68 | SET domain containing (lysine methyltransferase) 7 |
| MYCT1 | 3.79 | 6.63 | 6.07 | myc target 1 |
| KIAA0825 | 3.75 | 4.30 | 4.73 | |
| FLRT2 | 3.74 | 2.88 | 3.40 | fibronectin leucine rich transmembrane protein 2 |
| PREX1 | 3.73 | 2.87 | 3.03 | phosphatidylinositol 3,4,5-trisphosphate-dependent RAC exchanger 1 |
| ASAM | 3.73 | 3.68 | 3.58 | adipocyte-specific adhesion molecule |
| CYP1B1 | 3.71 | 2.20 | 2.15 | cytochrome P450, family 1, subfamily B, polypeptide 1 |
| YPEL5 | 3.70 | 2.91 | 2.95 | yippee-like 5 (*Drosophila*) |
| SEMA5A | 3.69 | 5.53 | 5.37 | sema domain, seven thrombospondin repeats (type 1 and type 1-like), transmembrane domain (TM) and |

TABLE 2-continued

Variations of Transcript levels (2-fold or more) during DE formation in hESC-H9 and iPSC lines 3.12, 3.5, and 3.6

| GENE SYMBOL | DIFF'D-H9 VS [UNDIFF'D-H9] (folds) | [DIFF'D-IPSC3.12] VS [UNDIFF'D-IPSC3.12] (folds) | [Diff'd-iPSC3.4] vs [Undiff'd-iPSC3.4] (folds) | GENE DESCRIPTION |
|---|---|---|---|---|
| | | | | short cytoplasmic domain, (semaphorin) 5A |
| LEFTY2 | 3.68 | 8.55 | 6.11 | left-right determination factor 2 |
| C9ORF52 | 3.62 | 3.58 | 3.12 | chromosome 9 open reading frame 52 |
| SLITRK2\|LOC100129095 | 3.62 | 3.66 | 3.73 | SLIT and NTRK-like family, member 2\|similar to CXorf2 protein |
| SERPINE2 | 3.61 | 3.78 | 3.80 | serpin peptidase inhibitor, clade E (nexin, plasminogen activator inhibitor type 1), member 2 |
| B3GNT5 | 3.57 | 2.85 | 2.91 | UDP-GlcNAc:betaGal beta-1,3-N-acetylglucosaminyltransferase 5 |
| SLCO2A1 | 3.57 | 2.32 | 2.14 | solute carrier organic anion transporter family, member 2A1 |
| SLC35F3 | 3.55 | 3.21 | 3.38 | solute carrier family 35, member F3 |
| SOX5 | 3.55 | 4.09 | 3.99 | SRY (sex determining region Y)-box 5 |
| NUDT4P1 | 3.54 | 2.88 | 2.42 | nudix (nucleoside diphosphate linked moiety X)-type motif 4 pseudogene 1 |
| ANGPT2 | 3.54 | 5.23 | 3.90 | angiopoietin 2 |
| CAP2 | 3.53 | 2.97 | 3.00 | CAP, adenylate cyclase-associated protein, 2 (yeast) |
| NETO2 | 3.50 | 2.25 | 2.21 | neuropilin (NRP) and tolloid (TLL)-like 2 |
| TRY6\|PRSS2\|PRSS1\|PRSS3\|LOC100134294 | 3.50 | 3.12 | 3.59 | trypsinogen C\|protease, serine, 2 (trypsin 2)\|protease, serine, 1 (trypsin 1)\|protease, serine, 3\|hypothetical protein LOC100134294 |
| ANGPT1 | 3.49 | 3.56 | 3.37 | angiopoietin 1 |
| VANGL1 | 3.48 | 2.94 | 2.79 | vang-like 1 (van gogh, Drosophila) |
| CDA | 3.48 | 4.14 | 3.63 | cytidine deaminase |
| MCF2L2 | 3.46 | 3.33 | 3.11 | MCF.2 cell line derived transforming sequence-like 2 |
| C9ORF95 | 3.44 | 2.28 | 2.13 | chromosome 9 open reading frame 95 |
| GATA4 | 3.42 | 2.89 | 2.77 | GATA binding protein 4 |
| MAGI3 | 3.39 | 3.20 | 3.13 | membrane associated guanylate kinase, WW and PDZ domain containing 3 |
| WNT3 | 3.39 | 2.97 | 3.36 | wingless-type MMTV integration site family, member 3 |
| APOBEC3G\|APOBEC3F | 3.36 | 2.79 | 2.90 | apolipoprotein B mRNA editing enzyme, catalytic polypeptide-like 3G\|apolipoprotein B mRNA editing enzyme, catalytic polypeptide-like 3F |
| FOXA2 | 3.36 | 3.08 | 3.93 | forkhead box A2 |
| BRDT | 3.34 | 2.82 | 2.33 | bromodomain, testis-specific |
| TCAG7.1177 | 3.33 | 2.60 | 3.10 | opposite strand transcription unit to STAG3 |
| LOC389523\|LOC729438\|LOC730322 | 3.33 | 2.59 | 3.10 | similar to opposite strand transcription unit to Stag3 |
| ZSWIM5 | 3.32 | 2.79 | 2.75 | zinc finger, SWIM-type containing 5 |
| COCH | 3.32 | 2.08 | 2.53 | coagulation factor C homolog, cochlin (Limulus polyphemus) |
| EPHA4 | 3.31 | 4.54 | 4.66 | EPH receptor A4 |
| C1ORF61 | 3.30 | 3.51 | 3.49 | chromosome 1 open reading frame 61 |
| KEL | 3.29 | 4.02 | 4.07 | Kell blood group, metallo-endopeptidase |
| PPM1K | 3.29 | 3.71 | 3.74 | protein phosphatase 1K (PP2C domain containing) |
| SORCS1 | 3.29 | 3.64 | 4.01 | sortilin-related VPS10 domain containing receptor 1 |
| SLC46A3 | 3.28 | 2.01 | 2.00 | solute carrier family 46, member 3 |
| BHLHB2 | 3.23 | 2.26 | 2.43 | basic helix-loop-helix domain containing, class B, 2 |
| BMPR2 | 3.23 | 3.64 | 3.57 | bone morphogenetic protein receptor, type II (serine/threonine kinase) |
| CAMKK2 | 3.21 | 2.94 | 3.14 | calcium/calmodulin-dependent protein kinase kinase 2, beta |
| DAB2 | 3.21 | 2.38 | 2.30 | disabled homolog 2, mitogen-responsive phosphoprotein (Drosophila) |

TABLE 2-continued

Variations of Transcript levels (2-fold or more) during DE formation in hESC-H9 and iPSC lines 3.12, 3.5, and 3.6

| GENE SYMBOL | DIFF'D-H9] VS [UNDIFF'D-H9] (folds) | [DIFF'D-IPSC3.12] VS [UNDIFF'D-IPSC3.12] (folds) | [Diff'd-iPSC3.4] vs [Undiff'd-iPSC3.4] (folds) | GENE DESCRIPTION |
|---|---|---|---|---|
| ELMO1 | 3.20 | 5.68 | 4.76 | engulfment and cell motility 1 |
| SEMA6D | 3.20 | 6.82 | 6.05 | sema domain, transmembrane domain (TM), and cytoplasmic domain, (semaphorin) 6D |
| CXCR7 | 3.20 | 3.18 | 3.21 | chemokine (C—X—C motif) receptor 7 |
| P4HA1 | 3.20 | 2.63 | 2.45 | procollagen-proline, 2-oxoglutarate 4-dioxygenase (proline 4-hydroxylase), alpha polypeptide I |
| YAF2 | 3.17 | 2.48 | 2.87 | YY1 associated factor 2 |
| TMOD1 | 3.16 | 2.61 | 2.62 | tropomodulin 1 |
| RALB | 3.16 | 2.41 | 2.11 | v-ral simian leukemia viral oncogene homolog B (ras related; GTP binding protein) |
| FBN2 | 3.13 | 3.58 | 4.30 | fibrillin 2 (congenital contractural arachnodactyly) |
| KIAA1161 | 3.10 | 2.84 | 3.74 | |
| LTB4DH | 3.10 | 3.08 | 2.77 | leukotriene B4 12-hydroxydehydrogenase |
| DUSP4 | 3.10 | 3.14 | 2.43 | dual specificity phosphatase 4 |
| GPR39 | 3.09 | 5.74 | 6.56 | G protein-coupled receptor 39 |
| CNTN4 | 3.08 | 2.58 | 2.54 | contactin 4 |
| FRRS1 | 3.06 | 2.21 | 2.07 | ferric-chelate reductase 1 |
| PGM1 | 3.03 | 2.67 | 2.67 | phosphoglucomutase 1 |
| PDK1 | 3.03 | 4.84 | 5.36 | pyruvate dehydrogenase kinase, isozyme 1 |
| SOAT1 | 3.03 | 3.19 | 2.88 | sterol O-acyltransferase (acyl-Coenzyme A: cholesterol acyltransferase) 1 |
| CCDC92 | 3.00 | 2.79 | 2.97 | coiled-coil domain containing 92 |
| ZNF792 | 3.00 | 2.44 | 2.22 | zinc finger protein 792 |
| SLC35A3 | 3.00 | 3.55 | 2.83 | solute carrier family 35 (UDP-N-acetylglucosamine (UDP-GlcNAc) transporter), member A3 |
| SMAD7 | 3.00 | 2.23 | 2.07 | SMAD family member 7 |
| CEP55 | 2.99 | 2.02 | 2.08 | centrosomal protein 55 kDa |
| DDAH2 | 2.99 | 2.14 | 2.44 | dimethylarginine dimethylaminohydrolase 2 |
| DDAH2 | 2.98 | 2.15 | 2.44 | dimethylarginine dimethylaminohydrolase 2 |
| APOC1 | 2.97 | 2.73 | 2.14 | apolipoprotein C-I |
| TMEM133 | 2.95 | 3.63 | 3.12 | transmembrane protein 133 |
| HNF1B | 2.95 | 2.25 | 2.64 | HNF1 homeobox B |
| FLJ32810 | 2.94 | 3.55 | 2.92 | |
| RAP1GDS1 | 2.91 | 2.27 | 2.38 | RAP1, GTP-GDP dissociation stimulator 1 |
| DDAH2 | 2.90 | 2.08 | 2.29 | dimethylarginine dimethylaminohydrolase 2 |
| C5ORF36 | 2.90 | 2.59 | 2.45 | chromosome 5 open reading frame 36 |
| GCNT1 | 2.89 | 4.78 | 5.38 | glucosaminyl (N-acetyl) transferase 1, core 2 (beta-1,6-N-acetylglucosaminyltransferase) |
| APOBEC3D | 2.89 | 2.21 | 2.03 | apolipoprotein B mRNA editing enzyme, catalytic polypeptide-like 3D |
| NPPB | 2.88 | 3.62 | 3.57 | natriuretic peptide precursor B |
| MLYCD | 2.87 | 2.89 | 2.78 | malonyl-CoA decarboxylase |
| AADAT | 2.86 | 2.49 | 2.25 | aminoadipate aminotransferase |
| STMN2 | 2.85 | 5.88 | 5.04 | stathmin-like 2 |
| SULF2 | 2.85 | 3.19 | 2.99 | sulfatase 2 |
| ANKRD6 | 2.84 | 3.01 | 3.06 | ankyrin repeat domain 6 |
| TBX3 | 2.84 | 2.18 | 2.16 | T-box 3 (ulnar mammary syndrome) |
| APOA2 | 2.83 | 3.62 | 3.42 | apolipoprotein A-II |
| PPFIBP1 | 2.83 | 2.60 | 2.45 | PTPRF interacting protein, binding protein 1 (liprin beta 1) |
| ALDH1A1 | 2.82 | 2.46 | 2.18 | aldehyde dehydrogenase 1 family, member A1 |
| LIFR | 2.82 | 2.31 | 2.51 | leukemia inhibitory factor receptor alpha |
| ID1 | 2.81 | 2.49 | 2.73 | inhibitor of DNA binding 1, dominant negative helix-loop-helix protein |

TABLE 2-continued

Variations of Transcript levels (2-fold or more) during DE formation in hESC-H9 and iPSC lines 3.12, 3.5, and 3.6

| GENE SYMBOL | DIFF'D-H9] VS [UNDIFF'D-H9] (folds) | [DIFF'D-IPSC3.12] VS [UNDIFF'D-IPSC3.12] (folds) | [Diff'd-iPSC3.4] vs [Undiff'd-iPSC3.4] (folds) | GENE DESCRIPTION |
|---|---|---|---|---|
| MTUS1 | 2.81 | 2.72 | 2.99 | mitochondrial tumor suppressor 1 |
| MYL4 | 2.80 | 2.45 | 2.05 | myosin, light chain 4, alkali; atrial, embryonic |
| YPEL2 | 2.80 | 2.68 | 2.30 | yippee-like 2 (Drosophila) |
| FZD5 | 2.80 | 6.24 | 5.60 | frizzled homolog 5 (Drosophila) |
| TNNC1 | 2.80 | 2.31 | 2.03 | troponin C type 1 (slow) |
| TMPRSS11E\|TMPRSS11E2 | 2.79 | 3.23 | 3.04 | transmembrane protease, serine 11E\|transmembrane protease, serine 11E2 |
| CCDC75 | 2.78 | 2.47 | 2.15 | coiled-coil domain containing 75 |
| EGF | 2.78 | 4.20 | 3.94 | epidermal growth factor (beta-urogastrone) |
| KIT | 2.78 | 4.03 | 3.60 | v-kit Hardy-Zuckerman 4 feline sarcoma viral oncogene homolog |
| TMPRSS11E\|TMPRSS11E2 | 2.76 | 3.23 | 2.97 | transmembrane protease, serine 11E\|transmembrane protease, serine 11E2 |
| KCNG1 | 2.72 | 2.33 | 2.68 | potassium voltage-gated channel, subfamily G, member 1 |
| CUGBP2 | 2.72 | 2.54 | 2.11 | CUG triplet repeat, RNA binding protein 2 |
| CDH10 | 2.71 | 3.23 | 4.02 | cadherin 10, type 2 (T2-cadherin) |
| LEFTY1 | 2.70 | 4.86 | 5.04 | left-right determination factor 1 |
| C20ORF95 | 2.68 | 3.26 | 3.35 | chromosome 20 open reading frame 95 |
| ACSS3 | 2.67 | 2.12 | 2.10 | acyl-CoA synthetase short-chain family member 3 |
| FAM126B | 2.67 | 2.27 | 2.00 | family with sequence similarity 126, member B |
| PERP | 2.66 | 2.40 | 2.73 | |
| GATA6 | 2.65 | 3.93 | 4.05 | GATA binding protein 6 |
| ANKS1B | 2.64 | 2.39 | 2.26 | ankyrin repeat and sterile alpha motif domain containing 1B |
| CA2 | 2.61 | 2.48 | 2.36 | carbonic anhydrase II |
| TMEM135 | 2.58 | 2.71 | 2.72 | transmembrane protein 135 |
| CCDC3 | 2.58 | 2.68 | 2.84 | coiled-coil domain containing 3 |
| JAKMIP1 | 2.57 | 2.02 | 2.07 | janus kinase and microtubule interacting protein 1 |
| APOBEC3C\|APOBEC3D | 2.55 | 2.40 | 2.44 | apolipoprotein B mRNA editing enzyme, catalytic polypeptide-like 3C\|apolipoprotein B mRNA editing enzyme, catalytic polypeptide-like 3D |
| FZD8 | 2.54 | 3.57 | 3.26 | frizzled homolog 8 (Drosophila) |
| SYNJ1 | 2.54 | 2.43 | 2.33 | synaptojanin 1 |
| GATA3 | 2.54 | 2.04 | 2.15 | GATA binding protein 3 |
| QPCT | 2.53 | 3.59 | 3.29 | glutaminyl-peptide cyclotransferase (glutaminyl cyclase) |
| C8ORF79 | 2.52 | 2.17 | 2.90 | chromosome 8 open reading frame 79 |
| ZNF702 | 2.52 | 2.41 | 2.01 | zinc finger protein 702 |
| EDNRA | 2.52 | 2.69 | 2.27 | endothelin receptor type A |
| MAGED1 | 2.51 | 2.89 | 2.99 | melanoma antigen family D, 1 |
| DTWD2 | 2.50 | 2.53 | 2.32 | DTW domain containing 2 |
| KITLG | 2.48 | 2.12 | 2.82 | KIT ligand |
| APOBEC3F\|APOBEC3G | 2.48 | 2.48 | 2.29 | apolipoprotein B mRNA editing enzyme, catalytic polypeptide-like 3F\|apolipoprotein B mRNA editing enzyme, catalytic polypeptide-like 3G |
| ETS2 | 2.47 | 2.17 | 2.05 | v-ets erythroblastosis virus E26 oncogene homolog 2 (avian) |
| GNAL | 2.46 | 3.70 | 3.72 | guanine nucleotide binding protein (G protein), alpha activating activity polypeptide, olfactory type |
| ZNF518B | 2.45 | 3.00 | 2.39 | zinc finger protein 518B |
| HGSNAT | 2.45 | 2.95 | 2.90 | heparan-alpha-glucosaminide N-acetyltransferase |
| B4GALT4 | 2.42 | 2.12 | 2.05 | UDP-Gal:betaGlcNAc beta 1,4-galactosyltransferase, polypeptide 4 |
| ATP8A1 | 2.42 | 2.91 | 2.77 | ATPase, aminophospholipid transporter (APLT), class I, type 8A, member 1 |
| SYT10 | 2.41 | 2.13 | 2.26 | synaptotagmin X |
| EFNA5 | 2.41 | 2.62 | 2.83 | ephrin-A5 |

TABLE 2-continued

Variations of Transcript levels (2-fold or more) during DE formation in hESC-H9 and iPSC lines 3.12, 3.5, and 3.6

| GENE SYMBOL | DIFF'D-H9] VS [UNDIFF'D-H9] (folds) | [DIFF'D-IPSC3.12] VS [UNDIFF'D-IPSC3.12] (folds) | [Diff'd-iPSC3.4] vs [Undiff'd-iPSC3.4] (folds) | GENE DESCRIPTION |
|---|---|---|---|---|
| SMARCD3 | 2.40 | 2.70 | 2.39 | SWI/SNF related, matrix associated, actin dependent regulator of chromatin, subfamily d, member 3 |
| WDR44 | 2.40 | 2.48 | 2.26 | WD repeat domain 44 |
| EPHA2 | 2.39 | 2.03 | 2.12 | EPH receptor A2 |
| BCAR3 | 2.38 | 2.41 | 2.31 | breast cancer anti-estrogen resistance 3 |
| UNC50 | 2.36 | 3.44 | 3.34 | unc-50 homolog (*C. elegans*) |
| LY6E | 2.36 | 2.35 | 2.14 | lymphocyte antigen 6 complex, locus E |
| SLC5A9 | 2.34 | 7.86 | 6.18 | solute carrier family 5 (sodium/glucose cotransporter), member 9 |
| COL4A1 | 2.33 | 2.20 | 2.15 | collagen, type IV, alpha 1 |
| KIAA0825 | 2.32 | 2.72 | 2.49 | |
| NSUN3 | 2.32 | 2.41 | 2.15 | NOL1/NOP2/Sun domain family, member 3 |
| HEBP2 | 2.32 | 2.58 | 2.45 | heme binding protein 2 |
| COL6A1 | 2.32 | 2.20 | 2.52 | collagen, type VI, alpha 1 |
| PMEPA1 | 2.31 | 2.35 | 2.24 | prostate transmembrane protein, androgen induced 1 |
| STC1 | 2.30 | 2.94 | 3.30 | stanniocalcin 1 |
| MBNL3 | 2.29 | 2.65 | 2.47 | muscleblind-like 3 (*Drosophila*) |
| FST | 2.29 | 2.59 | 2.99 | follistatin |
| TNRC18\|LOC27320 | 2.28 | 2.09 | 2.17 | trinucleotide repeat containing 18\|hypothetical protein LOC27320 |
| LRRC3 | 2.25 | 2.18 | 2.53 | leucine rich repeat containing 3 |
| INPP4A | 2.25 | 2.50 | 2.55 | inositol polyphosphate-4-phosphatase, type I, 107 kDa |
| RRAGB | 2.25 | 2.26 | 2.21 | Ras-related GTP binding B |
| SLC9A9 | 2.25 | 2.70 | 3.10 | solute carrier family 9 (sodium/hydrogen exchanger), member 9 |
| TMEM123 | 2.25 | 2.26 | 2.27 | transmembrane protein 123 |
| GPR151 | 2.24 | 5.25 | 4.07 | G protein-coupled receptor 151 |
| NR3C1 | 2.24 | 2.58 | 2.64 | nuclear receptor subfamily 3, group C, member 1 (glucocorticoid receptor) |
| FAM89A | 2.22 | 2.14 | 2.32 | family with sequence similarity 89, member A |
| SHISA3 | 2.21 | 3.03 | 2.52 | shisa homolog 3 (*Xenopus laevis*) |
| GLT1D1 | 2.21 | 2.71 | 2.37 | glycosyltransferase 1 domain containing 1 |
| NRIP1 | 2.21 | 2.18 | 2.02 | nuclear receptor interacting protein 1 |
| WNT8A | 2.21 | 3.19 | 2.99 | wingless-type MMTV integration site family, member 8A |
| AKAP13 | 2.20 | 2.05 | 2.08 | A kinase (PRKA) anchor protein 13 |
| GPR37 | 2.20 | 2.36 | 2.53 | G protein-coupled receptor 37 (endothelin receptor type B-like) |
| COL4A6 | 2.19 | 2.76 | 3.25 | collagen, type IV, alpha 6 |
| DMN | 2.19 | 2.05 | 2.34 | desmuslin |
| PHF10 | 2.17 | 2.02 | 2.05 | PHD finger protein 10 |
| CCDC46 | 2.17 | 2.06 | 2.09 | coiled-coil domain containing 46 |
| TBX20 | 2.15 | 2.06 | 2.21 | T-box 20 |
| RCAN3 | 2.15 | 2.42 | 2.48 | RCAN family member 3 |
| ATP2B4 | 2.15 | 2.96 | 2.97 | ATPase, Ca++ transporting, plasma membrane 4 |
| FBXO34 | 2.15 | 2.05 | 2.19 | F-box protein 34 |
| C1ORF97 | 2.15 | 2.13 | 2.08 | chromosome 1 open reading frame 97 |
| MAPK10 | 2.14 | 2.59 | 2.41 | mitogen-activated protein kinase 10 |
| CCNG2 | 2.13 | 2.17 | 2.08 | cyclin G2 |
| CYP27A1 | 2.12 | 3.89 | 3.49 | cytochrome P450, family 27, subfamily A, polypeptide 1 |
| FUT8 | 2.12 | 3.09 | 2.80 | fucosyltransferase 8 (alpha (1,6) fucosyltransferase) |
| CTBS | 2.11 | 2.58 | 2.41 | chitobiase, di-N-acetyl- |
| ODZ4 | 2.10 | 2.46 | 2.76 | odz, odd Oz/ten-m homolog 4 (*Drosophila*) |
| TRAF5 | 2.10 | 2.09 | 2.02 | TNF receptor-associated factor 5 |
| FZD4 | 2.09 | 2.40 | 2.63 | frizzled homolog 4 (*Drosophila*) |
| PCDH7 | 2.09 | 3.85 | 4.19 | protocadherin 7 |
| IL18R1 | 2.09 | 2.89 | 2.88 | interleukin 18 receptor 1 |
| PLXNA4 | 2.06 | 2.09 | 2.27 | plexin A4 |

TABLE 2-continued

Variations of Transcript levels (2-fold or more) during DE formation in hESC-H9 and iPSC lines 3.12, 3.5, and 3.6

| GENE SYMBOL | DIFF'D-H9] VS [UNDIFF'D-H9] (folds) | [DIFF'D-IPSC3.12] VS [UNDIFF'D-IPSC3.12] (folds) | [Diff'd-iPSC3.4] vs [Undiff'd-iPSC3.4] (folds) | GENE DESCRIPTION |
|---|---|---|---|---|
| KCNK12 | 2.06 | 2.44 | 2.20 | potassium channel, subfamily K, member 12 |
| GPM6A | 2.04 | 5.17 | 5.20 | glycoprotein M6A |
| MAGED2 | 2.04 | 2.12 | 2.28 | melanoma antigen family D, 2 |
| PDGFC | 2.04 | 2.14 | 2.30 | platelet derived growth factor C |
| IFI16 | 2.03 | 4.18 | 3.33 | interferon, gamma-inducible protein 16 |
| ABCC4 | 2.03 | 3.31 | 2.93 | ATP-binding cassette, sub-family C (CFTR/MRP), member 4 |
| C4ORF35 | 2.02 | 2.19 | 2.01 | chromosome 4 open reading frame 35 |
| ELMOD2 | 2.01 | 2.42 | 2.07 | ELMO/CED-12 domain containing 2 |
| SH3RF1 | 2.01 | 2.35 | 2.34 | SH3 domain containing ring finger 1 |

Example 8

Tissue Processing, Immunohistochemistry and Microscopy

Tissues were fixed for 1 hour to overnight in 4% paraformaldehyde or 3% glutaraldehyde for transmission electron microscopy (TEM). Cultured PSCs and DE cells were stained directly. Hindgut and intestinal organoids were, embedded in paraffin, epoxy resin LX-112 (Ladd Research, Burlington, Vt.), or frozen in OCT. Sections were cut 6-10 micrometers for standard microscopy and 0.1 micrometers for TEM. TEM sections were stained with uranyl acetate. Parrafin sections were deparaffinized, subjected to antigen retrieval, blocked in the appropriate serum (5% serum in 1×PBS+0.5% triton-X) for 30 minutes, and incubated with primary antibody overnight at 4 degrees Celsius. Slides were washed and incubated in secondary antibody in blocking buffer for 2 hours at room temperature. For a list of antibodies used and dilutions, see Table 3A and 3B. Slides were washed and mounted using Fluormount-G. Confocal images were captured on a Zeiss LSM510 and Z-stacks were analyzed and assembled using AxioVision software. A Hitachi H7600 transmission electron microscope was used to capture images.

TABLE 3A

Primary Antibodies.

| PRIMARY ANTIBODY | SOURCE | DILUTION |
|---|---|---|
| Mouse anti-Phosphohistone H3 | Abcam | 1:500 |
| Rat anti-BrdU | Abcam | 1:500-1:1000 |
| Rabbit anti-Ki67 | Dako | 1:500 |
| Goat anti-Sox17 | R&D Systems | 1:500 |
| Mouse anti-FoxA2 | Novus Biologicals | 1:500 |
| Goat anti-Villin | Santa Cruz | 1:200-1:500 |
| Mouse anti-Cdx2 | BioGenex | 1:500 |
| Rabbit anti-ChromograninA | ImmunoStar | 1:1000 |
| Rabbit anti-Mucin (MUC2) | Santa Cruz | 1:200 |
| Rabbit anti-Lysozyme | Zymed Laboratories | 1:1000 |
| Rat anti-Klf5 | Dr. Ichiro Manabe | 1:2000 |
| Rabbit anti-Sox9 | Millipore | 1:1000 |
| Rabbit anti-Albumin | Sigma | 1:1000 |
| Rabbit anti-Laminin | Abcam | 1:500 |
| Mouse anti-E-Cadherin | BD Biosciences | 1:500 |
| Mouse anti-Smooth Muscle Actin | Millipore | 1:500 |
| Mouse anti-Neurogenin 3 | DSHB | 1:100 |

TABLE 3A-continued

Primary Antibodies.

| PRIMARY ANTIBODY | SOURCE | DILUTION |
|---|---|---|
| Goat anti-Vimentin | Santa Cruz | 1:1000 |
| Goat anti-Pdx1 | Abcam | 1:5000 |
| Goat anti-Dpp4 | R&D Systems | 1:500 |
| Rabbit anti-Phosphohistone H3 | Cell Signaling | 1:500 |
| Goat anti-Gata4 | Santa Cruz | 1:200 |
| Rabbit anti-Gata6 | Santa Cruz | 1:200 |
| Rabbit anti-Nanog | Cosmo Bio. Co. | 1:2500 |
| Chicken anti-DNMT3b | Millipore | 1:1000 |
| Mouse anti-Tra 1-60 | Millipore | 1:500 |
| Mouse anti-Tra 1-81 | Millipore | 1:500 |

TABLE 3B

Secondary Antibodies.

| SECONDARY ANTIBODY | SOURCE | DILUTION |
|---|---|---|
| Goat anti-guinea pig Cy5 | Jackson Immuno | 1:500 |
| Goat anti-rabbit Cy5 | Jackson Immuno | 1:500 |
| Goat anti-rabbit Cy3 | Jackson Immuno | 1:500 |
| Goat anti-mouse Cy3 | Jackson Immuno | 1:500 |
| Goat anti-mouse 488 | Invitrogen | 1:500 |
| Goat anti-rabbit 488 | Invitrogen | 1:500 |
| Donkey anti-guinea pig Cy5 | Jackson Immuno | 1:500 |
| Donkey anti-rabbit Cy5 | Jackson Immuno | 1:500 |
| Donkey anti-rabbit Cy3 | Jackson Immuno | 1:500 |
| Donkey anti-mouse Cy3 | Jackson Immuno | 1:500 |
| Donkey anti-rabbit 488 | Invitrogen | 1:500 |
| Donkey anti-mouse 488 | Invitrogen | 1:500 |

Example 9

Adenovirus Production and Transduction

Adenoviral plasmids were obtained from Addgene and particles were generated according to the manufacturers protocol (Invitrogen—ViraPower Adenoviral Gateway Expression System) as previously described. 28 day organoids were removed from Matrigel and manually bisected with a scalpal. One half of each organoid was then incubated in Ad-GFP or Ad-Neurog3 viral supernatant and media at a 1:1 ratio for approximately 4 hours. Organoids were then re-embedded in Matrigel and incubated overnight with viral supernatant and media at a 1:1 ratio. The next day, fresh organoid media was placed on the cultures and was changed as described until the end of the experiment.

Adenoviral-Mediated Expression of NEUROG3.

Adenoviral plasmids were obtained from Addgene and particles were generated as previously described. Transduction was done on 28 day organoids that were removed from Matrigel, manually bisected then incubated in Ad-GFP or Ad-Neurog3 viral supernatant and media at a 1:1 ratio for approximately 4 hours. Organoids were then re-embedded in Matrigel and incubated overnight with viral supernatant and media at a 1:1 ratio, then transferred to fresh media until the end of the experiment.

More details can be found, for example, in Zhou et al., "In vivo reprogramming of adult pancreatic exocrine cells to beta-cells," Nature 455, 627-632 (2008); which is incorporated herein in its entirety.

Example 10

RNA Isolation, Reverse Transcription and Quantitative PCR (qPCR)

RNA was isolated using the Nucleospin II RNA isolation kit (Clonetech). Reverse Transcription was carried out using the SuperScriptIII Supermix (Invitrogen) according to manufacturers protocol. Finally, qPCR was carried out using Quantitect SybrGreen MasterMix (Qiagen) on a Chromo4 Real-Time PCR (BioRad). PCR primers sequences were typically obtained from qPrimerD epot (http://primerdepot<dot>nci<dot>nih<dot>gov/). Exemplary primers (SEQ ID NO.: 1-16 used can be found in the following Table 4.

TABLE 4

Exemplary primers used.

| GENES | FORWARD PRIMERS | REVERSE PRIMERS |
| --- | --- | --- |
| Beta-Tubulin | GATACCTCACCGTGGCTGCT (SEQ ID NO.: 1) | AGAGGAAAGGGGCAGTTGAGT (SEQ ID NO.: 2) |
| Pdx1 | CGTCCGCTTGTTCTCCTC (SEQ ID NO.: 3) | CCTTTCCCATGGATGAAGTC (SEQ ID NO.: 4) |
| Albumin | AACGCCAGTAAGTGACAGAGTC (SEQ ID NO.: 5) | AGGTCTCCTTATCGTCAGCCT (SEQ ID NO.: 6) |
| Cdx2 | GGGCTCTCTGAGAGGCAGGT (SEQ ID NO.: 7) | GGTGACGGTGGGGTTTAGCA (SEQ ID NO.: 8) |
| Sox9 | GTACCCGCACTTGCACAAC (SEQ ID NO.: 9) | GTGGTCCTTCTTGTGCTGC (SEQ ID NO.: 10) |
| Villin | CCAAAGGCCTGAGTGAAATC (SEQ ID NO.: 11) | CCTGGAGCAGCTAGTGAACA (SEQ ID NO.: 12) |
| Lysozyme | ACAAGCTACAGCATCAGCGA (SEQ ID NO.: 13) | GTAATGATGGCAAAACCCCA (SEQ ID NO.: 14) |
| HoxA13 | GCACCTTGGTATAAGGCACG (SEQ ID NO.: 15) | CCTCTGGAAGTCCACTCTGC (SEQ ID NO.: 16) |

Example 11

Figure 15A:
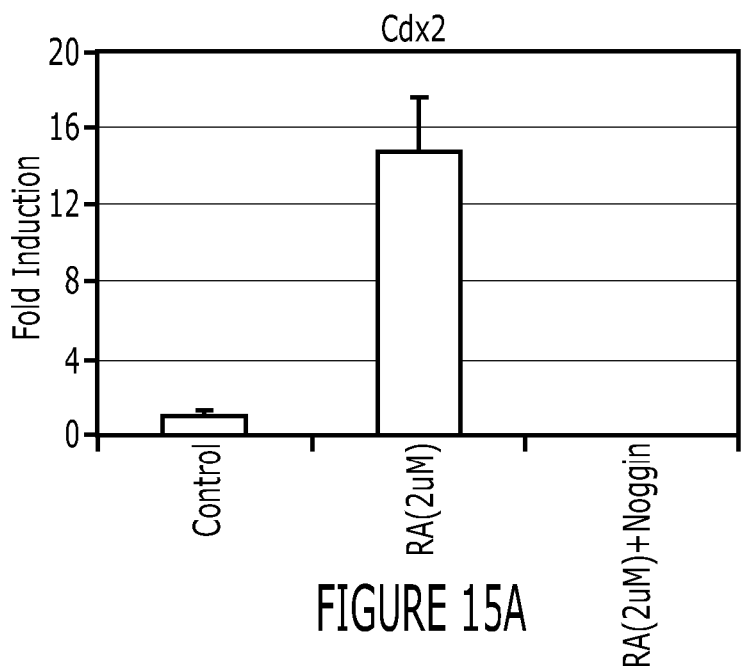
FIGS. 15A, 15C and 15D are bar charts that illustrate hindgut differentiation in a BMP dependent manner as a result of retinoic acid administration.
Figure 15B:
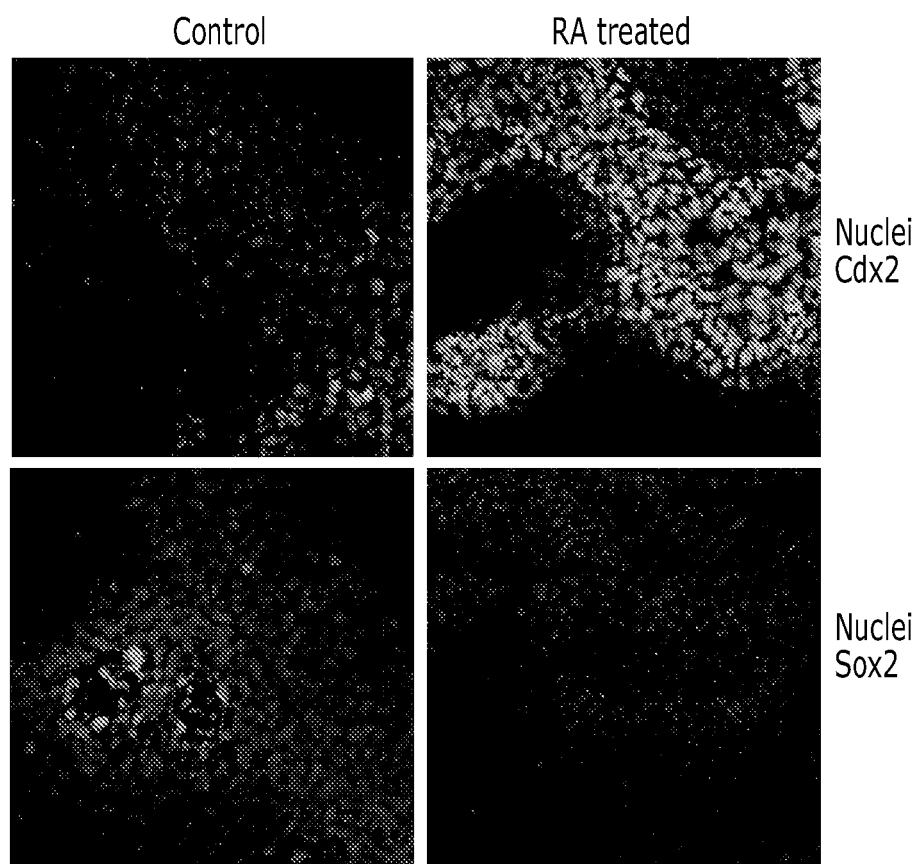
FIG. 15B is an immunofluorescent image illustrating the effects of Retinoic Acid and inhibition of BMP on differentiation of definitive endoderm into foregut and hindgut.
Figure 15C:
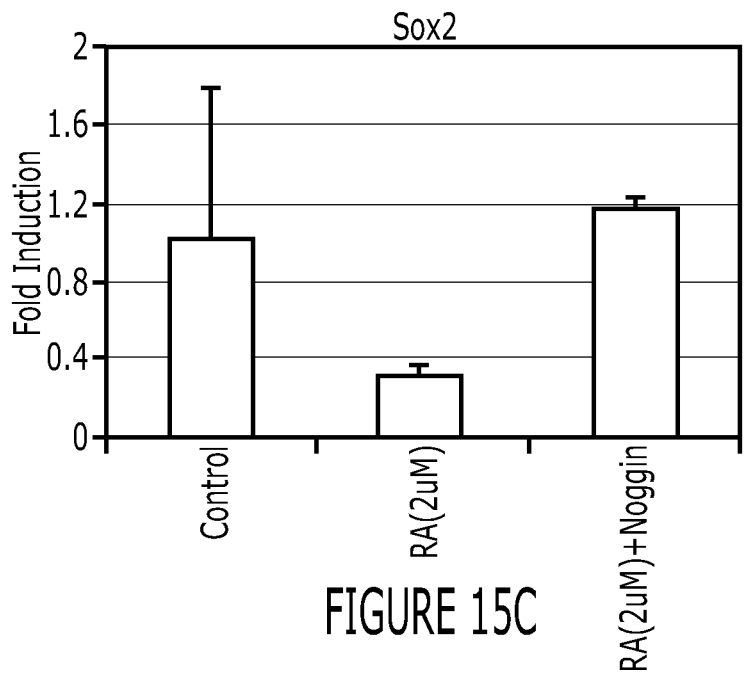
Figure 15D:
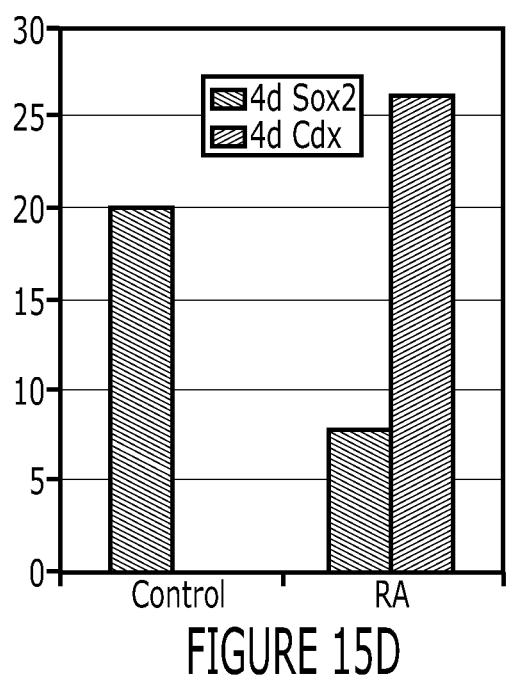
Figure 16C:
FIG. 16C includes immunofluorescent images of Noggin/EGF/Rspondid1-treated organoids that express CCK in the epithelium, thus indicating a proximal small bowel fate.
Figure 16C:

Regulation of Formation of Foregut and Hindgut from Human Embryonic and Induced Pluripotent Stem Cells Results and mechanisms for signaling network that regulates foregut, hindgut and intestinal development are shown in FIGS. 14-16. A summary of the pathways involved is shown in FIG. 14A.

Following definitive endoderm (DE) induction with activin (100 ng/ml) for 3 days, a 2-4 day treatment was performed with the indicated combination of factors: Wnt3a (500 ng/ml) and Fgf4 (500 ng/ml), Retinoic acid (RA) in a range of 0.2-20 µM the BMP antagonist Noggin (50 ng/ml), the WNT antagonist DU (1-500 ng/ml).

The Noggin completely abolishes the Wnt/Fgf-induced Cdx2 expression (FIG. 14B). Retinoic acid (2 µM) can posteriorize newly-formed definitive endoderm, especially in the first two days following DE induction. The Retinoic acid (RA)-induced posteriorization is also dependent on endogenous BMP signaling, as the addition of Noggin potently inhibits Cdx2 expression.

For investigating the impact of BMP signaling on intestinal regionalization after hindgut formation, hindgut spheroids were plated in matrigel and BMP or noggin were added to EGF/Rspondid1 containing media. Intestinal organoids were analyzed after 28 days.

It has been identified that, in addition to FGF and WNT signaling, BMP and RA signaling are capable of promoting a posterior/hindgut fate and repressing foregut fate. Additionally, BMP signaling regulates formation of distinct regional types of intestine. Inhibition of BMP with noggin after the hindgut stage promotes a proximal intestinal fate (duodenum/jejunum). Activation of BMP signaling after the hindgut stage promotes a more distal intestinal cell fate (cecum/colon).

FIGS. 14B-14D demonstrate the effects of FGF, WNT, and BMP signaling on differentiation of Definitive endoderm into foregut and hindgut. In particular, FIGS. 14B and 14D depict the activation of FGF/WNT/BMP signaling promotes posterior/hindgut fate as indicated by expression of Cdx2. Repression of BMP signaling with noggin suppresses hindgut fate and promotes foregut fate. Activation of FGF/WNT/BMP signaling represses foregut fate as indicated by expression of Sox2 (FIG. 14C). Repression of WNT signaling with DU promotes anterior gene expression (HHex and Cerberus) and represses posterior/hindgut fate (Cdx2) (FIG. 14D).

The effects of Retinoic Acid in promoting hindgut differentiation in a BMP dependent manner (FIGS. 15A-15D). Quantitative realtime PCR was used to compare the effects of Retinoic Acid and inhibition of BMP on differentiation of Definitive endoderm into foregut and hindgut (FIGS. 15A and 15B). Similar comparison was also performed by immunostaining (FIGS. 15C and 15D). Activation of RA signaling promotes posterior/hindgut fate as indicated by expression of Cdx2 and represses foregut fate as indicated by expression of Sox2. Immunostaining in FIG. 15C is quantified in FIG. 15D using an automated cell counting program.

FIGS. 16A through 16C demonstrate that BMP signaling regulates formation of proximal and distal intestine formation from human embryonic and induced pluripotent stem cells. FIG. 16A shows that BMP2 promotes a posterior fate for monolayers when added during 96-hour WNT/FGF (W/F) treatment as shown by decreased expression of GATA4 compared to W/F alone and by increased expression of HOXC9 (distal small bowel and proximal colon), HOXD13, and HOXA13 compared to W/F alone.

FIG. 16B shows that, after formation of hindgut sphereoids, addition of BMP2 to 3D cultures promotes patterning of developing intestinal organoids to a distal fate after 28 days compared to the Nog/EGF/Rspo1 cocktail without BMP2 as shown by decreased relative expression of PDX1 and increased expression of HOXD13 and CA1 (carbonic anhydrase-colonocyte marker).

FIG. 16C shows that Day 138 Noggin/EGF/Rspondid1 treated organoids express CCK in the epithelium by immunostaining thus indicating a proximal small bowel fate.

FIGS. 14A-14D depict formation of foregut and hindgut from human embryonic and induced pluripotent stem cells is regulated by WNT, FGF, BMP and Retinoic acid (RA) signaling. A) Summary of the signaling network that regulates hindgut and intestinal development. B-D) Effects of FGF, WNT, and BMP signaling on differentiation of definitive endoderm into foregut and hindgut. B) and D). Activation of FGF/WNT/BMP signaling promotes posterior/hindgut fate as indicated by expression of Cdx2. Repression of BMP signaling with noggin suppresses hindgut fate and promotes foregut fate. C) Activation of FGF/WNT/BMP signaling represses foregut fate as indicated by expression of Sox2. D) Repression of WNT signaling with DU promotes anterior gene expression (HHex and Cerberus) and represses posterior/hindgut fate (Cdx2).

FIGS. 15A-15D depict retinoic acid promotes hindgut differentiation in a BMP dependent manner. Comparing the effects of Retinoic Acid and inhibition of BMP on differentiation of Definitive endoderm into foregut and hindgut by quantitative realtime PCR A) and B) or by immunostaining C) and D). Activation of RA signaling promotes posterior/hindgut fate as indicated by expression of Cdx2 and represses foregut fate as indicated by expression of Sox2. Immunostaining in C is quantified in D using an automated cell counting program.

FIGS. 16A-16C depict BMP signaling regulates formation of proximal and distal intestine formation from human embryonic and induced pluripotent stem cells. A) BMP2 promotes a posterior fate for monolayers when added during 96-hour WNT/FGF (W/F) treatment as shown by decreased expression of GATA4 compared to W/F alone and by increased expression of HOXC9 (distal small bowel and proximal colon), HOXD13, and HOXA13 compared to W/F alone. B) After formation of hindgut sphereoids, addition of BMP2 to 3D cultures promotes patterning of developing intestinal organoids to a distal fate after 28 days compared to the Nog/EGF/Rspo1 cocktail without BMP2 as shown by decreased relative expression of PDX1 and increased expression of HOXD13 and CA1 (carbonic anhydrase-colonocyte marker). C) Day 138 Noggin/EGF/Rspondid1 treated organoids express CCK in the epithelium by immunostaining thus indicating a proximal small bowel fate.

The various methods and techniques described above provide a number of exemplary ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof. Many variations and alternative elements have been disclosed in embodiments of the present invention. Still further variations and alternate elements will be apparent to one of skill in the art.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

REFERENCES CITED

All references cited are incorporated herein by reference in their entireties and for all purposes to the same extent as if each individual publication or patent or patent application was specifically and individually indicated to be incorporated by reference in its entirety for all purposes.

What is claimed is:

1. An in vitro method of inducing formation of mammalian intestinal tissue, comprising the steps of:
   a) contacting mammalian definitive endoderm cells with 100 ng/ml of FGF4 or higher and 100 ng/ml or higher Wnt3a for at least 96 hours to obtain posterior definitive endoderm cells,
   b) culturing the posterior definitive endoderm cells of step (a) to obtain 3-dimensional spheroids,
   c) embedding the 3-dimensional spheroids of step (b) in a basement membrane-like matrix to obtain intestinal tissue; and
   d) maintaining said embedded intestinal tissue in a media comprising at least 50 ng/mL of EGF, wherein said maintaining produces a stable mammalian intestinal tissue.

2. The method of claim 1, wherein said definitive endoderm cell is contacted by Wnt3a during a first activation period and by FGF4 during a second activation period.

3. The method of claim 2, wherein said first activation period and said second activation period overlap.

4. The method of claim 2, wherein said first activation period and said second activation period do not overlap.

5. The method of claim 1, wherein the definitive endoderm cell is derived from a mouse or human pluripotent stem cell.

6. The method of claim 5, wherein said pluripotent stem cell is an embryonic stem cell or an induced pluripotent stem cell.

7. The method of claim 5, wherein said definitive endoderm cell is derived by contacting the pluripotent stem cell with one or more molecules selected from the group consisting of Activin, the BMP subgroups of the TGF-β superfamily of growth factors; Nodal, Activin A, Activin B, BMP4, Wnt3a, and combinations thereof.

8. The method of claim 5, wherein said pluripotent stem cell is a human pluripotent stem cell.

9. The method of claim 8, wherein said human pluripotent stem cell is selected from the group consisting of a human embryonic stem cell, a human embryonic germ cell, and an induced human pluripotent stem cell.

\* \* \* \* \*

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: PCR Primer

<400> SEQUENCE: 1
gatacctcac cgtggctgct                                                      20

<210> SEQ ID NO 2
<211> LENGTH: 21
<212> TYPE: DNA
<213> ORGANISM: Artificial Sequence
<220> FEATURE:
<223> OTHER INFORMATION: PCR Primer

<400> SEQUENCE: 2
agaggaaagg ggcagttgag t                                                    21

<210> SEQ ID NO 3
<211> LENGTH: 18
<212> TYPE: DNA
<213> ORGANISM: Artificial Sequence
<220> FEATURE:
<223> OTHER INFORMATION: PCR Primer

<400> SEQUENCE: 3
cgtccgcttg ttctcctc                                                        18

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
cctttcccat ggatgaagtc                                                      20
```

-continued

<210> SEQ ID NO 5
<211> LENGTH: 22
<212> TYPE: DNA
<213> ORGANISM: Artificial Sequence
<220> FEATURE:
<223> OTHER INFORMATION: PCR Primer

<400> SEQUENCE: 5
aacgccagta agtgacagag tc                                          22

<210> SEQ ID NO 6
<211> LENGTH: 21
<212> TYPE: DNA
<213> ORGANISM: Artificial Sequence
<220> FEATURE:
<223> OTHER INFORMATION: PCR Primer

<400> SEQUENCE: 6
aggtctcctt atcgtcagcc t                                           21

<210> SEQ ID NO 7
<211> LENGTH: 20
<212> TYPE: DNA
<213> ORGANISM: Artificial Sequence
<220> FEATURE:
<223> OTHER INFORMATION: PCR Primer

<400> SEQUENCE: 7
gggctctctg agaggcaggt                                             20

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
ggtgacggtg gggtttagca                                             20

<210> SEQ ID NO 9
<211> LENGTH: 19
<212> TYPE: DNA
<213> ORGANISM: Artificial Sequence
<220> FEATURE:
<223> OTHER INFORMATION: PCR Primer

<400> SEQUENCE: 9
gtacccgcac ttgcacaac                                              19

<210> SEQ ID NO 10
<211> LENGTH: 19
<212> TYPE: DNA
<213> ORGANISM: Artificial Sequence
<220> FEATURE:
<223> OTHER INFORMATION: PCR Primer

<400> SEQUENCE: 10
gtggtccttc ttgtgctgc                                              19

<210> SEQ ID NO 11
<211> LENGTH: 20
<212> TYPE: DNA
<213> ORGANISM: Artificial Sequence
<220> FEATURE:

```
<223> OTHER INFORMATION: PCR Primer

<400> SEQUENCE: 11
ccaaaggcct gagtgaaatc                                               20

<210> SEQ ID NO 12
<211> LENGTH: 20
<212> TYPE: DNA
<213> ORGANISM: Artificial Sequence
<220> FEATURE:
<223> OTHER INFORMATION: PCR Primer

<400> SEQUENCE: 12
cctggagcag ctagtgaaca                                               20

<210> SEQ ID NO 13
<211> LENGTH: 20
<212> TYPE: DNA
<213> ORGANISM: Artificial Sequence
<220> FEATURE:
<223> OTHER INFORMATION: PCR Primer

<400> SEQUENCE: 13
acaagctaca gcatcagcga                                               20

<210> SEQ ID NO 14
<211> LENGTH: 20
<212> TYPE: DNA
<213> ORGANISM: Artificial Sequence
<220> FEATURE:
<223> OTHER INFORMATION: PCR Primer

<400> SEQUENCE: 14
gtaatgatgg caaaacccca                                               20

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
gcaccttggt ataaggcacg                                               20

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
cctctggaag tccactctgc                                               20
```